United States Patent

Todo et al.

Patent Number: 5,935,952
Date of Patent: Aug. 10, 1999

[54] QUINOLONE- OR NAPHTHYLIDONE-CARBOXYLIC ACID DERIVATES OR THEIR SALTS

[75] Inventors: Yozo Todo, Toyama; Kazuya Hayashi, Uozu; Masahiro Tadahata, Imizu-Gun; Yasuo Watanabe; Hirokazu Narita, both of Toyama, all of Japan

[73] Assignee: Toyama Chemical Co., LTD., Tokyo, Japan

[21] Appl. No.: 08/776,711

[22] PCT Filed: Aug. 4, 1995

[86] PCT No.: PCT/JP95/01551

§ 371 Date: Feb. 12, 1997

§ 102(e) Date: Feb. 12, 1997

[87] PCT Pub. No.: WO96/05192

PCT Pub. Date: Feb. 22, 1996

[30] Foreign Application Priority Data

Aug. 12, 1994  [JP]  Japan ................................ 6-212083

[51] Int. Cl.[6] ............... A61K 31/37; A61K 31/535; C07D 215/56; C07D 498/06
[52] U.S. Cl. .................... 514/230.2; 514/224.5; 514/250; 514/299; 514/300; 514/312; 544/32; 544/101; 544/250; 546/123; 546/156
[58] Field of Search ................... 546/156, 123; 544/32, 101, 250; 514/299, 300, 224.5, 230.2, 250, 312

[56] References Cited

U.S. PATENT DOCUMENTS 4,563,459  1/1986  Grohe ........................... 514/254
4,945,160  7/1990  Kiely ............................ 540/481
5,026,856  6/1991  Yatsunami ..................... 546/156

FOREIGN PATENT DOCUMENTS 61-143365   7/1986   Japan .
1-319463   12/1989   Japan .

Primary Examiner—Evelyn Huang
Attorney, Agent, or Firm—Oblon, Spivak, McClelland, Maier & Neustadt, P.C.

[57] ABSTRACT

This invention relates to a novel quinolone- or naphthyridone-carboxylic acid derivative or its salt useful as an antibacterial agent, said derivative has a substituent represented by the following formula at the 7 position:

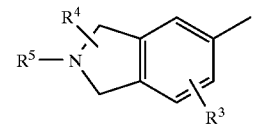

wherein preferably $R^3$ represents at least one member selected from the group consisting of a hydrogen atom, a halogen atom, a substituted or unsubstituted lower alkyl, lower alkoxy or lower alkylthio group, a nitro group, a cyano group, a protected or unprotected hydroxyl group and a protected or unprotected amino group; $R^4$ represents a hydrogen atom, a substituted or unsubstituted lower alkyl group, a lower alkylidene group and a group forming a cycloalkane ring together with the carbon atom to which $R^4$ is bonded; and $R^5$ represents a hydrogen atom or a substituted or unsubstituted lower alkyl or cycloalkyl group.

15 Claims, No Drawings

QUINOLONE- OR NAPHTHYLIDONE-CARBOXYLIC ACID DERIVATES OR THEIR SALTS

This application is the national phase of PCT/JP95/01551 filed Aug. 4, 1995, published as WO 96/05192 on Feb. 22, 1996.

TECHNICAL FIELD

This invention relates to a novel quinolone- or naphthylidone-carboxylic acid derivative represented by the general formula [1] or its salt which exhibits a strong antibacterial activity against Gram-positive bacteria and Gram-negative bacteria, particularly MRSA.

BACKGROUND ART

As a quinolone type synthetic antibacterial agent, Norfloxacin, Ciprofloxacin, Ofloxacin and the like have heretofore been widely used in clinic, but do not have a sufficient activity against Gram-positive bacteria, particularly MRSA. Therefore, it has been desired to develop synthetic antibacterial agents which are effective to these bacteria and have a broad antibacterial spectrum.

DISCLOSURE OF INVENTION

Under such circumstances, the present inventors have made extensive research to find that a quinolone- or naphthylidone-carboxylic acid derivative represented by the general formula [1] or its salt has an excellent antibacterial activity:

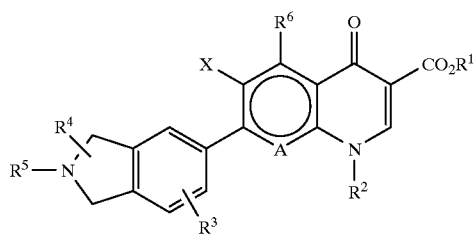

[1]

wherein $R^1$ represents a hydrogen atom or a carboxyl-protecting group; $R^2$ represents a substituted or unsubstituted alkyl, alkenyl, cycloalkyl, aryl or heterocyclic group; $R^3$ represents at least one group selected from the group consisting of a hydrogen atom, a halogen atom, a substituted or unsubstituted alkyl, alkenyl, cycloalkyl, aryl, alkoxy or alkylthio group, a nitro group, a cyano group, an acyl group, a protected or unprotected hydroxyl group, a protected or unprotected hydroxyalkyl group, a protected or unprotected amino group, a protected or unprotected alkylamino group, a dialkylamino group, a protected or unprotected aminoalkyl group, a protected or unprotected alkylaminoalkyl group and a dialkylaminoalkyl group; $R^4$ represents at least one group selected form the group consisting of a hydrogen atom, a halogen atom, a substituted or unsubstituted alkyl, alkenyl, cycloalkyl, aralkyl, aryl, alkoxy or alkylthio group, a protected or unprotected hydroxyl group, a protected or unprotected hydroxyalkyl group, a protected or unprotected amino group, a protected or unprotected alkylamino group, a dialkylamino group, a protected or unprotected aminoalkyl group, a protected or unprotected alkylaminoalkyl group, a dialkylaminoalkyl group, an alkylidene group, an oxo group, an imino group and a group forming a cycloalkane ring together with the carbon atom to which $R^4$ is bonded; $R^5$ represents a hydrogen atom, a substituted or unsubstituted alkyl, cycloalkyl, alkylsulfonyl, arylsulfonyl, acyl or aryl group, a protected or unprotected aminoalkyl group, a protected or unprotected alkylaminoalkyl group, a dialkylaminoalkyl group or a protected or unprotected hydroxyalkyl group; $R^6$ represents a hydrogen atom, a halogen atom, a substituted or unsubstituted alkyl, alkoxy or alkylthio group, a protected or unprotected hydroxyl group, a protected or unprotected amino group or a nitro group;

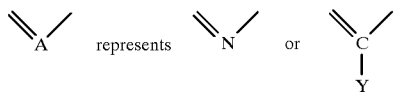

in which Y represents a hydrogen atom, a halogen atom, a substituted or unsubstituted alkyl, alkoxy or alkylthio group or a protected or unprotected hydroxyl group or forms a group represented by the following formula together with $R^2$:

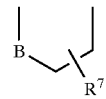

in which $R^7$ represents at least one group selected from the group consisting of a hydrogen atom, an alkyl group, a halogenoalkyl group, a protected or unprotected hydroxyalkyl group, an alkylidene group and a group forming a cycloalkane ring together with the carbon atom to which $R^7$ is bonded and B represents an oxygen atom, a sulfur atom or an imino group which may be substituted by an alkyl group; and X represents a hydrogen atom or a halogen atom, whereby this invention has been completed.

This invention is explained in detail below.

In the present specification, unless otherwise specified, the term "halogen atom" means a fluorine atom, a chlorine atom, a bromine atom or an iodine atom; the term "alkyl group" means a straight chain or branched chain $C_{1-10}$alkyl group such as methyl, ethyl, n-propyl, isopropyl, n-butyl, isobutyl, sec-butyl, tert-butyl, pentyl, hexyl, heptyl, octyl or the like; the term "lower alkyl group" means a straight chain or branched chain $C_{1-5}$alkyl group such as methyl, ethyl, n-propyl, isopropyl, n-butyl, isobutyl, sec-butyl, tert-butyl, pentyl or the like; the term "alkoxy group" means a straight chain or branched chain $C_{1-10}$alkoxy group such as methoxy, ethoxy, n-propoxy, isopropoxy, n-butoxy, isobutoxy, sec-butoxy, tert-butoxy, pentyloxy, hexyloxy, heptyloxy, octyloxy or the like; the term "lower alkoxy group" means a straight chain or branched chain $C_{1-5}$alkoxy group such as methoxy, ethoxy, n-propoxy, isopropoxy, n-butoxy, isobutoxy, sec-butoxy, tert-butoxy, pentyloxy or the like; the term "alkylthio group" means a straight chain or branched chain $C_{1-10}$alkylthio group such as methylthio, ethylthio, n-propylthio, isopropylthio, n-butylthio, isobutylthio, sec-butylthio, tert-butylthio, pentylthio, hexylthio, heptylthio, octylthio or the like; the term "lower alkylthio group" means a straight chain or branched chain $C_{1-5}$alkylthio group such as methylthio, ethylthio, n-propylthio, isopropylthio, n-butylthio, isobutylthio, sec-butylthio, tert-butylthio, pentylthio or the like; the term "acyl group" means a formyl group, a straight chain or branched chain $C_{2-5}$alkanoyl group such as acetyl, ethylcarbonyl or the like or an aroyl group such as benzoyl, naphthylcarbonyl or the like; the term "lower alkoxycarbonyl group" means a straight chain or branched chain $C_{1-5}$alkoxycarbonyl group such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, pentyloxycarbonyl or the like; the term "alkylamino group" means a straight chain or branched chain $C_{1-10}$alkylamino group such as methylamino, ethylamino, propylamino, butylamino, pentylamino, hexylamino, heptylamino, octylamino or the like; the term "lower alkylamino group" means a straight chain or branched chain $C_{1-5}$alkylamino group such as methylamino, ethylamino, propylamino or the like; the term "dialkylamino group" means a di-straight chain or branched chain $C_{1-10}$alkylamino group such as dimethylamino, diethylamino, methylethylamino, dipropylamino, dibutylamino, dipentylamino, dihexylamino, diheptylamino, dioctylamino or the like; the term "di-lower alkylamino group" means a di-straight chain or branched chain $C_{1-5}$alkylamino group such as dimethylamino, diethylamino, methylethylamino or the like; the term "aminoalkyl group" means an amino-straight chain or branched chain $C_{1-10}$alkyl group such as aminomethyl, aminoethyl, aminopropyl, aminobutyl, aminopentyl, aminohexyl, amino-heptyl, amino-octyl or the like; the term "amino-lower alkyl group" means an amino-straight chain or branched chain $C_{1-5}$alkyl group such as aminomethyl, aminoethyl, aminopropyl or the like; the term "alkylaminoalkyl group" means a straight chain or branched chain $C_{1-10}$alkylamino-straight chain or branched chain $C_{1-10}$alkyl group such as methylaminomethyl, methylaminoethyl, ethylaminomethyl, methylaminopropyl, propylaminoethyl, methylaminobutyl, butylaminoethyl, pentylaminomethyl, methylaminohexyl, heptylaminopropyl, butylaminooctyl or the like; the term "lower alkylamino-lower alkyl group" means a straight chain or branched chain $C_{1-5}$alkylamino-straight chain or branched chain $C_{1-5}$alkyl group such as methylaminomethyl, methylaminoethyl, ethylaminomethyl, methylaminopropyl, propylaminoethyl or the like; the term "dialkylaminoalkyl group" means a di-straight chain or branched chain $C_{1-10}$alkylamino-straight chain or branched chain $C_{1-10}$alkyl group such as dimethylaminomethyl, diethylaminomethyl, diethylaminopropyl, dimethylaminobutyl, dipropylaminomethyl, dibutylaminomethyl, diethylaminopentyl, dihexylaminomethyl, dipentylaminoheptyl, dioctylaminohexyl or the like; the term "di-lower alkylamino-lower alkyl group" means a distraight chain or branched chain $C_{1-5}$alkylamino-straight chain or branched chain $C_{1-5}$alkyl group such as dimethylaminomethyl, diethylaminomethyl, diethylaminoethyl, dimethylaminopropyl or the like; the term "hydroxyalkyl group" means a hydroxy-straight chain or branched chain $C_{1-10}$alkyl group such as hydroxymethyl, hydroxyethyl, hydroxypropyl, hydroxybutyl, hydroxypentyl, hydroxyhexyl, hydroxyheptyl, hydroxyoctyl or the like; the term "hydroxy-lower alkyl group" means a hydroxy-straight chain or branched chain $C_{1-5}$alkyl group such as hydroxymethyl, hydroxyethyl, hydroxypropyl or the like; the term "halogenoalkyl group" means a halogeno-straight chain or branched chain $C_{1-10}$alkyl group such as fluoromethyl, chloromethyl, bromomethyl, dichloromethyl, trifluoromethyl, trichloromethyl, chloroethyl, dichloroethyl, trichloroethyl, chloropropyl, chlorobutyl, chloropentyl, chlorohexyl, chloroheptyl, chlorooctyl or the like; the term "halogeno-lower alkyl group" means a halogeno-straight chain or branched chain $C_{1-5}$alkyl group such as fluoromethyl, chloromethyl, bromomethyl, dichloromethyl, trifluoromethyl, trichloromethyl, chloroethyl, dichloroethyl, trichloroethyl, chloropropyl or the like; the term "alkenyl group" means a straight chain or branched chain $C_{2-10}$alkenyl group such as vinyl, allyl, isopropenyl, butenyl, pentenyl, hexenyl, heptenyl, octenyl or the like; the term "lower alkenyl group" means a straight chain or branched chain $C_{2-5}$alkenyl group such as vinyl, allyl or the like; the term "alkylidene group" means a straight chain or branched chain $C_{1-10}$alkylidene group such as methylene, ethylidene, propylidene, isopropylidene, butylidene, hexylidene, octylidene or the like; the term "lower alkylidene group" means a straight chain or branched chain $C_{1-5}$alkylidene group such as methylene, ethylidene, propylidene, isopropylidene or the like; the term "cycloalkyl group" means a $C_{3-6}$cycloalkyl group such as cyclopropyl, cyclobutyl, cyclopentyl, cyclohexyl or the like; the term "cycloalkane ring" means a $C_{3-6}$cycloalkane ring such as cyclopropane, cyclobutane, cyclopentane, cyclohexane or the like; the term "alkylsulfonyl group" means a straight chain or branched chain $C_{1-10}$alkylsulfonyl group such as methylsulfonyl, ethylsulfonyl, n-propylsulfonyl, isopropylsulfonyl, n-butylsulfonyl, isobutylsulfonyl, sec-butylsulfonyl, tert-butylsulfonyl, pentylsulfonyl, hexylsulfonyl, heptylsulfonyl, octylsulfonyl or the like; the term "lower alkylsulfonyl group" means a straight chain or branched chain $C_{1-5}$alkylsulfonyl group such as methylsulfonyl, ethylsulfonyl, n-propylsulfonyl, isopropylsulfonyl, n-butylsulfonyl, isobutylsulfonyl, sec-butylsulfonyl, tert-butylsulfonyl, pentylsulfonyl or the like; the term "aryl group" means a phenyl or naphthyl group or the like; the term "arylsulfonyl group" means a phenylsulfonyl or naphthylsulfonyl group or the like; the term "aralkyl group" means a benzyl or phenethyl group or the like; and the term "heterocyclic group" means a 4-membered, 5-membered or 6-membered cyclic group containing at least one hetero atom selected from the group consisting of oxygen atom, nitrogen atom and sulfur atom as the hetero atom forming the ring or a condensed cyclic group thereof such as oxetanyl, thietanyl, azetidinyl, furyl, pyrrolyl, thienyl, oxazolyl, isoxazolyl, imidazolyl, thiazolyl, isothiazolyl, pyrrolidinyl, benzofuranyl, benzothiazolyl, pyridyl, quinolyl, pyrimidinyl or morpholinyl group.

The substituent of the substituted or unsubstituted lower alkyl, alkyl, lower alkenyl, alkenyl, cycloalkyl, aryl or heterocyclic group in $R^2$; the substituent of the substituted or unsubstituted lower alkyl, alkyl, lower alkenyl, alkenyl, cycloalkyl, aryl, lower alkoxy, alkoxy, lower alkylthio or alkylthio group in $R^3$; the substituent of the substituted or unsubstituted lower alkyl, alkyl, lower alkenyl, alkenyl, cycloalkyl, aralkyl, aryl, lower alkoxy, alkoxy, lower alkylthio or alkylthio group in $R^4$; the substituent of the substituted or unsubstituted lower alkyl, alkyl, cycloalkyl, lower alkylsulfonyl, alkylsulfonyl, arylsulfonyl, acyl or aryl group in $R^5$; the substituent of the substituted or unsubstituted lower alkyl, alkyl, lower alkoxy, alkoxy, lower alkylthio or alkylthio group in $R^6$; and the substituent of the substituted or unsubstituted lower alkyl, alkyl, lower alkoxy, alkoxy, lower alkylthio or alkylthio group in Y include halogen atoms, cyano group, protected or unprotected carboxyl groups, protected or unprotected hydroxyl groups, protected unprotected amino groups, lower alkyl groups, lower alkoxy groups, lower alkoxycarbonyl groups, aryl groups, cycloalkyl groups, lower alkenyl groups, halogeno-lower alkyl groups, protected or unprotected lower alkylamino groups and di-lower alkylamino groups, and may be substituted by at least one of these substituents.

The carboxyl-protecting group includes all conventional carboxyl-protecting groups and there are specifically mentioned lower alkyl groups such as methyl, ethyl, n-propyl, isopropyl, 1,1-dimethylpropyl, n-butyl, tert-butyl and the like; aryl groups such as phenyl, naphthyl and the like; ar-lower alkyl groups such as benzyl, diphenylmethyl, trityl, p-nitrobenzyl, p-methoxybenzyl, bis(p-methoxyphenyl) methyl and the like; acyl-lower alkyl groups such as acetylmethyl, benzoylmethyl, p-nitrobenzoylmethyl, p-bromobenzoylmethyl, p-methanesulfonylbenzoylmethyl and the like; oxygen-containing heterocyclic groups such as 2-tetrahydropyranyl, 2-tetrahydrofuranyl and the like; halogeno-lower alkyl groups such as 2,2,2-trichloroethyl and the like; lower alkylsilylalkyl groups such as 2-(trimethylsilyl)ethyl and the like; acyloxyalkyl groups such as acetoxymethyl, propionyloxymethyl, pivaloyloxymethyl and the like; nitrogen-containing heterocyclic lower alkyl groups such as phthalimidomethyl, succinimidomethyl and the like; cycloalkyl groups such as cyclohexyl and the like; lower alkoxy-lower alkyl groups such as methoxymethyl, methoxyethoxymethyl, 2-(trimethylsilyl) ethoxymethyl and the like; ar-lower alkoxy-lower alkyl groups such as benzyloxymethyl and the like; lower alkylthio-lower alkyl groups such as methylthiomethyl, 2-methylthioethyl and the like; arylthio-lower alkyl groups such as phenylthiomethyl and the like; lower alkenyl groups such as 1,1-dimethyl-2-propenyl, 3-methyl-3-butenyl, allyl and the like; and substituted silyl groups such as trimethylsilyl, triethylsilyl, triisopropylsilyl, diethylisopropylsilyl, tert-butyldimethylsilyl, tert-butyldiphenylsilyl, diphenylmethylsilyl, tert-butylmethoxyphenylsilyl and the like; etc.

Also, the protecting group of the protected amino, lower alkylamino, alkylamino, amino-lower alkyl, aminoalkyl, lower alkylamino-lower alkyl or alkylaminoalkyl group includes all conventional amino-protecting groups and there are specifically mentioned acyl groups such as trichloroethoxycarbonyl, tribromoethoxycarbonyl, benzyloxycarbonyl, p-nitrobenzylcarbonyl, o-bromobenzyloxycarbonyl, (mono-, di- or tri-) chloroacetyl, trifluoroacetyl, phenylacetyl, formyl, acetyl, benzoyl, tert-amyloxycarbonyl, tert-butoxycarbonyl, p-methoxybenzyloxycarbonyl, 3,4-dimethoxybenzyloxycarbonyl, 4-(phenylazo) benzyloxycarbonyl, 2-furfuryloxycarbonyl, diphenylmethoxycarbonyl, 1,1-dimethylpropoxycarbonyl, isopropoxycarbonyl, phthaloyl, succinyl, alanyl, leucyl, 1-adamantyloxycarbonyl, 8-quinolyloxycarbonyl and the like; ar-lower alkyl groups such as benzyl, diphenylmethyl, trityl and the like; arylthio groups such as 2-nitrophenylthio, 2,4-dinitrophenylthio and the like; alkyl- and aryl-sulfonyl groups such as methanesulfonyl, p-toluenesulfonyl and the like; di-lower alkylamino-lower alkylidene groups such as N,N-dimethylaminomethylene and the like; ar-lower alkylidene groups such as benzylidene, 2-hydroxybenzylidene, 2-hydroxy-5-chlorobenzylidene, 2-hydroxy-1-naphthylmethylene and the like; nitrogen-containing heterocyclic alkylidene groups such as 3-hydroxy-4-pyridylmethylene and the like; cycloalkylidene groups such as cyclohexylidene, 2-ethoxycarbonylcyclohexylidene, 2-ethoxycarbonylcyclopentylidene, 2-acetylcyclohexylidene, 3,3-dimethyl-5-oxycyclohexylidene and the like; diaryl- and diar-lower alkylphosphoryl groups such as diphenylphosphoryl, dibenzylphosphoryl and the like; oxygen-containing heterocyclic alkyl groups such as 5-methyl-2-oxo-2H-1,3-dioxol-4-yl-methyl and the like; substituted silyl groups such as trimethylsilyl and the like; etc.

Moreover, the protecting group of the protected hydroxyl, hydroxyl-lower alkyl or hydroxyalkyl group includes all conventional hydroxyl-protecting groups, and there are specifically mentioned acyl groups such as benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl) ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl and the like; lower alkyl groups such as methyl, tert-butyl, 2,2,2-trichloroethyl, 2-trimethylsilylethyl and the like; lower alkenyl groups such as allyl and the like; ar-lower alkyl groups such as benzyl, p-methoxybenzyl, 3,4-dimethoxybenzyl, diphenylmethyl, trityl and the like; oxygen-containing and sulfur-containing heterocyclic groups such as tetrahydrofuryl, tetrahydropyranyl, tetrahydrothiopyranyl and the like; lower alkoxy- and lower alkylthio-lower alkyl groups such as methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl and the like; alkyl- and arylsulfonyl groups such as methanesulfonyl, p-toluenesulfonyl and the like; substituted silyl groups such as trimethylsilyl, triethylsilyl, triisopropylsilyl, diethylisopropylsilyl, tert-butyldimethylsilyl, tert-butyldiphenylsilyl, diphenylmethylsilyl, tert-butylmethoxyphenylsilyl and the like; etc.

The salt of the compound represented by the general formula [1] includes usually known salts at basic groups such as amino group and the like and salts at acidic groups such as hydroxyl group, carboxyl group and the like. The salts at the basic groups include, for example, salts with mineral acids such as hydrochloric acid, hydrobromic acid, sulfuric acid and the like; salts with organic carboxylic acids such as tartaric acid, formic acid, citric acid, trichloroacetic acid, trifluoroacetic acid and the like; and salts with sulfonic acids such as methanesulfonic acid, benzenesulfonic acid, p-touenesulfonic acid, mesitylenesulfonic acid, naphthalenesulfonic acid and the like; and the salts at the acidic groups include, for example, salts with alkali metals such as sodium, potassium and the like; salts with alkaline earth metals such as calcium, magnesium and the like; ammonium salts; nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, N,N'-dibenzylethylenediamine and the like; etc. Among the salts represented by the general formula [1], pharmaceutically acceptable salts are preferable.

Among the compounds of this invention, preferable are compounds of the general formula [1] wherein $R^2$ represents a substituted or unsubstituted lower alkyl, lower alkenyl, cycloalkyl, aryl or heterocyclic group; $R^3$ represents at least one group selected from the group consisting of a hydrogen atom, a halogen atom, a substituted or unsubstituted lower alkyl, lower alkenyl, cycloalkyl, aryl, lower alkoxy or lower alkylthio group, a nitro group, a cyano group, an acyl group, a protected or unprotected hydroxyl group, a protected or unprotected hydroxy-lower alkyl group, a protected or unprotected amino group, a protected or unprotected lower alkylamino group, a di-lower alkylamino group, a protected or unprotected amino-lower alkyl group, a protected or unprotected lower alkylamino-lower alkyl group and a di-lower alkylamino-lower alkyl group; $R^4$ represents at least one group selected from the group consisting of a hydrogen atom, a halogen atom, a substituted or unsubstituted lower alkyl, lower alkenyl, cycloalkyl, aralkyl, aryl, lower alkoxy or lower alkylthio group, a protected or unprotected hydroxyl group, a protected or unprotected hydroxy-lower alkyl group, a protected or unprotected amino group, a protected or unprotected lower alkylamino group, a di-lower alkylamino group, a protected or unprotected amino-lower alkyl group, a protected or unprotected lower alkylamino-lower alkyl group, a di-lower alkylamino-lower alkyl group, a lower alkylidene group, an oxo group, an imino group and a group forming a cycloalkane ring together with the carbon atom to which $R^4$ is bonded; $R^5$ represents a hydrogen atom, a substituted or unsubstituted lower alkyl, cycloalkyl, lower alkylsulfonyl, arylsulfonyl, acyl or aryl group, a protected or unprotected amino-lower alkyl group, a protected or unprotected lower alkylamino-lower alkyl group, a di-lower alkylamino-lower alkyl group or a protected or unprotected hydroxy-lower alkyl group; $R^6$ represents a hydrogen atom, a halogen atom, a substituted or unsubstituted lower alkyl, lower alkoxy or lower alkylthio group, a protected or unprotected hydroxyl group, a protected or unprotected amino group or a nitro group;

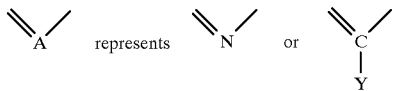

in which Y represents a hydrogen atom, a halogen atom, a substituted or unsubstituted lower alkyl, lower alkoxy or lower alkylthio group or a protected or unprotected hydroxyl group or forms a group represented by the following formula together with $R^2$:

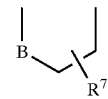

in which $R^7$ represents at least one group selected from the group consisting of a hydrogen atom, a lower alkyl group, a halogeno-lower alkyl group, a protected or unprotected hydroxy-lower alkyl group, a lower alkylidene group and a group forming a cycloalkane ring together with the carbon atom to which $R^7$ is bonded and B represents an oxygen atom, a sulfur atom or an imino group which may be substituted by a lower alkyl group and X represents a halogen atom. And more preferable are the compounds mentioned above provided that $R^3$ represents at least one group selected from the group consisting of a hydrogen atom, a halogen atom, a substituted or unsubstituted lower alkyl, lower alkoxy or lower alkylthio group, a nitro group, a cyano group, a protected or unprotected hydroxyl group and a protected or unprotected amino group. Particularly preferable are the compounds mentioned above provided that $R^4$ is at least one group selected from the group consisting of a hydrogen atom, a substituted or unsubstituted lower alkyl group, a lower alkylidene group and a group forming a cycloalkane ring together with the carbon atom to which $R^4$ is bonded. More particularly preferable are the compounds mentioned above provided that $R^5$ represents a hydrogen atom or a substituted or unsubstituted lower alkyl or cycloalkyl group.

Among the compounds of this invention, representative compounds thereof are as follows:

1-Cyclopropyl-6-fluoro-7-(isoindolin-5-yl)-8-methyl-1,4-dihydro-4-oxoquinoline-3-carboxylic acid
1-Ethyl-6-fluoro-7-(isoindolin-5-yl)-8-methyl-1,4-dihydro-4-oxoquinoline-3-carboxylic acid
1-(2,4-Difluorophenyl)-6-fluoro-7-(isoindolin-5-yl)-8-methyl-1,4-dihydro-4-oxoquinoline-3-carboxylic acid
6-Fluoro-1-(4-hydroxyphenyl)-7-(isoindolin-5-yl)-8-methyl-1,4-dihydro-4-oxoquinoline-3-carboxylic acid
6-Fluoro-1-(4-fluorophenyl)-7-(isoindolin-5-yl)-8-methyl-1,4-dihydro-4-oxoquinoline-3-carboxylic acid
6-Fluoro-1-[(1R,2S)-2-fluorocyclopropyl]-7-(isoindolin-5-yl)-8-methyl-1,4-dihydro-4-oxoquinoline-3-carboxylic acid
1-Cyclopropyl-6-fluoro-8-methyl-7-(2-methylisoindolin-5-yl)-1,4-dihydro-4-oxoquinoline-3-carboxylic acid
1-Ethyl-6-fluoro-8-methyl-7-(2-methylisoindolin-5-yl)-1,4-dihydro-4-oxoquinoline-3-carboxylic acid
1-(2,4-Difluorophenyl)-6-fluoro-8-methyl-7-(2-methylisoindolin-5-yl)-1,4-dihydro-4-oxoquinoline-3-carboxylic acid
6-Fluoro-1-(4-hydroxyphenyl)-8-methyl-7-(2-methylisoindolin-5-yl)-1,4-dihydro-4-oxoquinoline-3-carboxylic acid
6-Fluoro-1-(4-fluorophenyl)-8-methyl-7-(2-methylisoindolin-5-yl)-1,4-dihydro-4-oxoquinoline-3-carboxylic acid
6-Fluoro-1-[(1R,2S)-2-fluorocyclopropyl]-8-methyl-7-(2-methylisoindolin-5-yl)-1,4-dihydro-4-oxoquinoline-3-carboxylic acid
1-Cyclopropyl-6-fluoro-7-(isoindolin-5-yl)-1,4-dihydro-4-oxoquinoline-3-carboxylic acid
1-Ethyl-6-fluoro-7-(isoindolin-5-yl)-1,4-dihydro-4-oxoquinoline-3-carboxylic acid
1-(2,4-Difluorophenyl)-6-fluoro-7-(isoindolin-5-yl)-1,4-dihydro-4-oxoquinoline-3-carboxylic acid 6-Fluoro-1-(4-hydroxyphenyl)-7-(isoindolin-5-yl)-1,4-dihydro-4-oxoquinoline-3-carboxylic acid 6-Fluoro-1-(4-fluorophenyl)-7-(isoindolin-5-yl)-1,4-dihydro-4-oxoquinoline-3-carboxylic acid 6-Fluoro-1-[(1R,2S)-2-fluorocyclopropyl]-7-(isoindolin-5-yl)-1,4-dihydro-4-oxoquinoline-3-carboxylic acid 1-Cyclopropyl-6-fluoro-7-(2-methylisoindolin-5-yl)-1,4-dihydro-4-oxoquinoline-3-carboxylic acid 1-Ethyl-6-fluoro-7-(2-methylisoindolin-5-yl)-1,4-dihydro-4-oxoquinoline-3-carboxylic acid 1-(2,4-Difluorophenyl)-6-fluoro-7-(2-methylisoindolin-5-yl)-1,4-dihydro-4-oxoquinoline-3-carboxylic acid 6-Fluoro-1-(4-hydroxyphenyl)-7-(2-methylisoindolin-5-yl)-1,4-dihydro-4-oxoquinoline-3-carboxylic acid 6-Fluoro-1-(4-fluorophenyl)-7-(2-methylisoindolin-5-yl)-1,4-dihydro-4-oxoquinoline-3-carboxylic acid 6-Fluoro-1-[(1R,2S)-2-fluorocyclopropyl]-7-(2-methylisoindolin-5-yl)-1,4-dihydro-4-oxoquinoline-3-carboxylic acid 1-Cyclopropyl-6-fluoro-7-(isoindolin-5-yl)-8-methoxy-1,4-dihydro-4-oxoquinoline-3-carboxylic acid 1-Ethyl-6-fluoro-7-(isoindolin-5-yl)-8-methoxy-1,4-dihydro-4-oxoquinoline-3-carboxylic acid 1-(2,4-Difluorophenyl)-6-fluoro-7-(isoindolin-5-yl)-8-methoxy-1,4-dihydro-4-oxoquinoline-3-carboxylic acid 6-Fluoro-1-(4-hydroxyphenyl)-7-(isoindolin-5-yl)-8-methoxy-1,4-dihydro-4-oxoquinoline-3-carboxylic acid 6-Fluoro-1-(4-fluorophenyl)-7-(isoindolin-5-yl)-8-methoxy-1,4-dihydro-4-oxoquinoline-3-carboxylic acid 6-Fluoro-1-[(1R,2S)-2-fluorocyclopropyl]-7-(isoindolin-5-yl)-8-methoxy-1,4-dihydro-4-oxoquinoline-3-carboxylic acid 1-Cyclopropyl-6-fluoro-8-methoxy-7-(2-methylisoindolin-5-yl)-1,4-dihydro-4-oxoquinoline-3-carboxylic acid 1-Ethyl-6-fluoro-8-methoxy-7-(2-methylisoindolin-5-yl)-1,4-dihydro-4-oxoquinoline-3-carboxylic acid 1-(2,4-Difluorophenyl)-6-fluoro-8-methoxy-7-(2-methylisoindolin-5-yl)-1,4-dihydro-4-oxoquinoline-3-carboxylic acid 6-Fluoro-1-(4-hydroxyphenyl)-8-methoxy-7-(2-methylisoindolin-5-yl)-1,4-dihydro-4-oxoquinoline-3-carboxylic acid 6-Fluoro-1-(4-fluorophenyl)-8-methoxy-7-(2-methylisoindolin-5-yl)-1,4-dihydro-4-oxoquinoline-3-carboxylic acid 6-Fluoro-1-[(1R,2S)-2-fluorocyclopropyl]-8-methoxy-7-(2-methylisoindolin-5-yl)-1,4-dihydro-4-oxoquinoline-3-carboxylic acid 8-Chloro-1-cyclopropyl-6-fluoro-7-(isoindolin-5-yl)-1,4-dihydro-4-oxoquinoline-3-carboxylic acid 8-Chloro-1-ethyl-6-fluoro-7-(isoindolin-5-yl)-1,4-dihydro-4-oxoquinoline-3-carboxylic acid 8-Chloro-1-(2,4-difluorophenyl)-6-fluoro-7-(isoindolin-5-yl)-1,4-dihydro-4-oxoquinoline-3-carboxylic acid 8-Chloro-6-fluoro-1-(4-hydroxyphenyl)-7-(isoindolin-5-yl)-1,4-dihydro-4-oxoquinoline-3-carboxylic acid 8-Chloro-6-fluoro-1-(4-fluorophenyl)-7-(isoindolin-5-yl)-1,4-dihydro-4-oxoquinoline-3-carboxylic acid 8-Chloro-6-fluoro-1-[(1R,2S)-2-fluorocyclopropyl]-7-(isoindolin-5-yl)-1,4-dihydro-4-oxoquinoline-3-carboxylic acid 8-Chloro-1-cyclopropyl-6-fluoro-7-(2-methylisoindolin-5-yl)-1,4-dihydro-4-oxoquinoline-3-carboxylic acid 8-Chloro-1-ethyl-6-fluoro-7-(2-methylisoindolin-5-yl)-1,4-dihydro-4-oxoquinoline-3-carboxylic acid 8-Chloro-1-(2,4-difluorophenyl)-6-fluoro-7-(2-methylisoindolin-5-yl)-1,4-dihydro-4-oxoquinoline-3-carboxylic acid 8-Chloro-6-fluoro-1-(4-hydroxyphenyl)-7-(2-methylisoindolin-5-yl)-1,4-dihydro-4-oxoquinoline-3-carboxylic acid 8-Chloro-6-fluoro-1-(4-fluorophenyl)-7-(2-methylisoindolin-5-yl)-1,4-dihydro-4-oxoquinoline-3-carboxylic acid 8-Chloro-6-fluoro-1-[(1R,2S)-2-fluorocyclopropyl]-7-(2-methylisoindolin-5-yl)-1,4-dihydro-4-oxoquinoline-3-carboxylic acid 1-Cyclopropyl-6,8-difluoro-7-(isoindolin-5-yl)-1,4-dihydro- 4-oxoquinoline-3-carboxylic acid 1-Ethyl-6,8-difluoro-7-(isoindolin-5-yl)-1,4-dihydro-4-oxoquinoline-3-carboxylic acid 6,8-Difluoro-1-(2,4-difluorophenyl)-7-(isoindolin-5-yl)-1,4-dihydro-4-oxoquinoline-3-carboxylic acid 6,8-Difluoro-1-(4-hydroxyphenyl)-7-(isoindolin-5-yl)-1,4-dihydro-4-oxoquinoline-3-carboxylic acid 6,8-Difluoro-1-(4-fluorophenyl)-7-(isoindolin-5-yl)-1,4-dihydro-4-oxoquinoline-3-carboxylic acid 6,8-Difluoro-1-[(1R,2S)-2-fluorocyclopropyl]-7-(isoindolin-5-yl)-1,4-dihydro-4-oxoquinoline-3-carboxylic acid 1-Cyclopropyl-6,8-difluoro-7-(2-methylisoindolin-5-yl)-1,4-dihydro-4-oxoquinoline-3-carboxylic acid 1-Ethyl-6,8-difluoro-7-(2-methylisoindolin-5-yl)-1,4-dihydro-4-oxoquinoline-3-carboxylic acid 6,8-Difluoro-1-(2,4-difluorophenyl)-7-(2-methylisoindolin-5-yl)-1,4-dihydro-4-oxoquinoline-3-carboxylic acid 6,8-Difluoro-1-(4-hydroxyphenyl)-7-(2-methylisoindolin-5-yl)-1,4-dihydro-4-oxoquinoline-3-carboxylic acid 6,8-Difluoro-1-(4-fluorophenyl)-7-(2-methylisoindolin-5-yl)-1,4-dihydro-4-oxoquinoline-3-carboxylic acid 6,8-Difluoro-1-[(1R,2S)-2-fluorocyclopropyl]-7-(2-methylisoindolin-5-yl)-1,4-dihydro-4-oxoquinoline-3-carboxylic acid 1-Cyclopropyl-6-fluoro-7-(isoindolin-5-yl)-1,4-dihydro-4-oxo-1,8-naphthyridine-3-carboxylic acid 1-Ethyl-6-fluoro-7-(isoindolin-5-yl)-1,4-dihydro-4-oxo-1,8-naphthyridine-3-carboxylic acid 1-(2,4-Difluorophenyl)-6-fluoro-7-(isoindolin-5-yl)-1,4-dihydro-4-oxo-1,8-naphthyridine-3-carboxylic acid 6-Fluoro-1-(4-hydroxyphenyl)-7-(isoindolin-5-yl)-1,4-dihydro-4-oxo-1,8-naphthyridine-3-carboxylic acid 6-Fluoro-1-(4-fluorophenyl)-7-(isoindolin-5-yl)-1,4-dihydro-4-oxo-1,8-naphthyridine-3-carboxylic acid 6-Fluoro-1-[(1R,2S)-2-fluorocyclopropyl]-7-(isoindolin-5-yl)-1,4-dihydro-4-oxo-1,8-naphthyridine-3-carboxylic acid 1-Cyclopropyl-6-fluoro-7-(2-methylisoindolin-5-yl)-1,4-dihydro-4-oxo-1,8-naphthyridine-3-carboxylic acid 1-Ethyl-6-fluoro-7-(2-methylisoindolin-5-yl)-1,4-dihydro-4-oxo-1,8-naphthyridine-3-carboxylic acid 1-(2,4-Difluorophenyl)-6-fluoro-7-(2-methylisoindolin-5-yl)-1,4-dihydro-4-oxo-1,8-naphthyridine-3-carboxylic acid 6-Fluoro-1-(4-hydroxyphenyl)-7-(2-methylisoindolin-5-yl)-1,4-dihydro-4-oxo-1,8-naphthyridine-3-carboxylic acid 6-Fluoro-1-(4-fluorophenyl)-7-(2-methylisoindolin-5-yl)-1,4-dihydro-4-oxo-1,8-naphthyridine-3-carboxylic acid 6-Fluoro-1-[(1R,2S)-2-fluorocyclopropyl]-7-(2-methylisoindolin-5-yl)-1,4-dihydro-4-oxo-1,8-naphthyridine-3-carboxylic acid 9-Fluoro-10-(isoindolin-5-yl)-3-methyl-7-oxo-2,3-dihydro-7H-pyrido[1,2,3-de][1,4]benzoxazine-6-carboxylic acid (S)-9-Fluoro-10-(isoindolin-5-yl)-3-methyl-7-oxo-2,3-dihydro-7H-pyrido[1,2,3-de][1,4]benzoxazine-6-carboxylic acid 9-Fluoro-3-methyl-10-(2-methylisoindolin-5-yl)-7-oxo-2,3-dihydro-7H-pyrido[1,2,3-de][1,4]benzoxazine-6-carboxylic acid (S)-9-Fluoro-3-methyl-10-(2-methylisoindolin-5-yl)-7-oxo-2,3-dihydro-7H-pyrido[1,2,3-de][1,4]benzoxazine-6-carboxylic acid 1-Cyclopropyl-5,6,8-trifluoro-7-(isoindolin-5-yl)-1,4-dihydro-4-oxoquinoline-3-carboxylic acid 1-Cyclopropyl-5,6,8-trifluoro-7-(2-methylisoindolin-5-yl)-1,4-dihydro-4-oxoquinoline-3-carboxylic acid
5-Amino-1-cyclopropyl-6,8-difluoro-7-(isoindolin-5-yl)-1,4-dihydro-4-oxoquinoline-3-carboxylic acid.
5-Amino-1-cyclopropyl-6,8-difluoro-7-(2-methylisoindolin-5-yl)-1,4-dihydro-4-oxoquinoline-3-carboxylic acid
1-Cyclopropyl-6-fluoro-7-(7-fluoroisoindolin-5-yl)-1,4-dihydro-4-oxoquinoline-3-carboxylic acid
1-Cyclopropyl-6-fluoro-7-(7-methylisoindolin-5-yl)-1,4-dihydro-4-oxoquinoline-3-carboxylic acid
1-Cyclopropyl-6-fluoro-7-(4,6,7-trifluoroisoindolin-5-yl)-1,4-dihydro-4-oxoquinoline-3-carboxylic acid
1-Cyclopropyl-6-fluoro-7-(3-methylisoindolin-5-yl)-1,4-dihydro-4-oxoquinoline-3-carboxylic acid
1-Cyclopropyl-7-(1,3-dimethylisoindolin-5-yl)-6-fluoro-1,4-dihydro-4-oxoquinoline-3-carboxylic acid
1-Cyclopropyl-6-fluoro-7-(1-methylisoindolin-5-yl)-1,4-dihydro-4-oxoquinoline-3-carboxylic acid
1-Cyclopropyl-7-(1,1-dimethylisoindolin-5-yl)-6-fluoro-1,4-dihydro-4-oxoquinoline-3-carboxylic acid
1-Cyclopropyl-7-(3,3-dimethylisoindolin-5-yl)-6-fluoro-1,4-dihydro-4-oxoquinoline-3-carboxylic acid
1-Cyclopropyl-6-fluoro-8-fluoromethoxy-7-(isoindolin-5-yl)-1,4-dihydro-4-oxoquinoline-3-carboxylic acid
1-Ethyl-6-fluoro-8-fluoromethoxy-7-(isoindolin-5-yl)-1,4-dihydro-4-oxoquinoline-3-carboxylic acid
1-(2,4-Difluorophenyl)-6-fluoro-8-fluoromethoxy-7-(isoindolin-5-yl)-1,4-dihydro-4-oxoquinoline-3-carboxylic acid
6-Fluoro-8-fluoromethoxy-1-(4-hydroxyphenyl)-7-(isoindolin-5-yl)-1,4-dihydro-4-oxoquinoline-3-carboxylic acid
6-Fluoro-8-fluoromethoxy-1-(4-fluorophenyl)-7-(isoindolin-5-yl)-1,4-dihydro-4-oxoquinoline-3-carboxylic acid
6-Fluoro-1-[(1R,2S)-2-fluorocyclopropyl]-8-fluoromethoxy-7-(isoindolin-5-yl)-1,4-dihydro-4-oxoquinoline-3-carboxylic acid
1-Cyclopropyl-6-fluoro-8-fluoromethoxy-7-(2-methylisoindolin-5-yl)-1,4-dihydro-4-oxoquinoline-3-carboxylic acid
1-Ethyl-6-fluoro-8-fluoromethoxy-7-(2-methylisoindolin-5-yl)-1,4-dihydro-4-oxoquinoline-3-carboxylic acid
1-(2,4-Difluorophenyl)-6-fluoro-8-fluoromethoxy-7-(2-methylisoindolin-5-yl)-1,4-dihydro-4-oxoquinoline-3-carboxylic acid
6-Fluoro-8-fluoromethoxy-1-(4-hydroxyphenyl)-7-(2-methylisoindolin-5-yl)-1,4-dihydro-4-oxoquinoline-3-carboxylic acid
6-Fluoro-8-fluoromethoxy-1-(4-fluorophenyl)-7-(2-methylisoindolin-5-yl)-1,4-dihydro-4-oxoquinoline-3-carboxylic acid
6-Fluoro-1-[(1R,2S)-2-fluorocyclopropyl]-8-fluoromethoxy-7-(2-methylisoiodolin-5-yl)-1,4-dihydro-4-oxoquinoline-3-carboxylic acid
1-Cyclopropyl-8-difluoromethoxy-6-fluoro-7-(isoindolin-5-yl)-1,4-dihydro-4-oxoquinoline-3-carboxylic acid
8-Difluoromethoxy-1-ethyl-6-fluoro-7-(isoindolin-5-yl)-1,4-dihydro-4-oxoquinoline-3-carboxylic acid
8-Difluoromethoxy-1-(2,4-difluorophenyl)-6-fluoro-7-(isoindolin-5-yl)-1,4-dihydro-4-oxoquinoline-3-carboxylic acid
8-Difluoromethoxy-6-fluoro-1-(4-hydroxyphenyl)-7-(isoindolin-5-yl)-1,4-dihydro-4-oxoquinoline-3-carboxylic acid
8-Difluoromethoxy-6-fluoro-1-(4-fluorophenyl)-7-(isoindolin-5-yl)-1,4-dihydro-4-oxoquinoline-3-carboxylic acid
8-Difluoromethoxy-6-fluoro-1-[(1R,2S)-2-fluorocyclopropyl]-7-(isoindolin-5-yl)-1,4-dihydro-4-oxoquinoline-3-carboxylic acid
1-Cyclopropyl-8-difluoromethoxy-6-fluoro-7-(2-methylisoindolin-5-yl)-1,4-dihydro-4-oxoquinoline-3-carboxylic acid
8-Difluoromethoxy-1-ethyl-6-fluoro-7-(2-methylisoindolin-5-yl)-1,4-dihydro-4-oxoquinoline-3-carboxylic acid
8-Difluoromethoxy-1-(2,4-difluorophenyl)-6-fluoro-7-(2-methylisoindolin-5-yl)-1,4-dihydro-4-oxoquinoline-3-carboxylic acid
8-Difluoromethoxy-6-fluoro-1-(4-hydroxyphenyl)-7-(2-methylisoindolin-5-yl)-1,4-dihydro-4-oxoquinoline-3-carboxylic acid
8-Difluoromethoxy-6-fluoro-1-(4-fluorophenyl)-7-(2-methylisoindolin-5-yl)-1,4-dihydro-4-oxoquinoline-3-carboxylic acid
8-Difluoromethoxy-6-fluoro-1-[(1R,2S)-2-fluorocyclopropyl]-7-(2-methylisoindolin-5-yl)-1,4-dihydro-4-oxoquinoline-3-carboxylic acid
1-Cyclopropyl-6-fluoro-8-hydroxy-7-(isoindolin-5-yl)-1,4-dihydro-4-oxoquinoline-3-carboxylic acid
1-Ethyl-6-fluoro-8-hydroxy-7-(isoindolin-5-yl)-1,4-dihydro-4-oxoquinoline-3-carboxylic acid
1-(2,4-Difluorophenyl)-6-fluoro-8-hydroxy-7-(isoindolin-5-yl)-1,4-dihydro-4-oxoquinoline-3-carboxylic acid
6-Fluoro-8-hydroxy-1-(4-hydroxyphenyl)-7-(isoindolin-5-yl)-1,4-dihydro-4-oxoquinoline-3-carboxylic acid
6-Fluoro-1-(4-fluorophenyl)-8-hydroxy-7-(isoindolin-5-yl)-1,4-dihydro-4-oxoquinoline-3-carboxylic acid
6-Fluoro-1-[(1R,2S)-2-fluorocyclopropyl]-8-hydroxy-7-(isoindolin-5-yl)-1,4-dihydro-4-oxoquinoline-3-carboxylic acid
6-Fluoro-1-(2-fluoroethyl)-7-(isoindolin-5-yl)-8-methyl-1,4-dihydro-4-oxoquinoline-3-carboxylic acid
6-Fluoro-1-(2-fluoroethyl)-8-methyl-7-(2-methylisoindolin-5-yl)-1,4-dihydro-4-oxoquinoline-3-carboxylic acid
6-Fluoro-1-(2-fluoroethyl)-7-(isoindolin-5-yl)-1,4-dihydro-4-oxoquinoline-3-carboxylic acid
6-Fluoro-1-(2-fluoroethyl)-7-(2-methylisoindolin-5-yl)-1,4-dihydro-4-oxoquinoline-3-carboxylic acid
6-Fluoro-1-(2-fluoroethyl)-7-(isoindolin-5-yl)-8-methoxy-1,4-dihydro-4-oxoquinoline-3-carboxylic acid
6-Fluoro-1-(2-fluoroethyl)-7-(2-methylisoindolin-5-yl)-8-methoxy-1,4-dihydro-4-oxoquinoline-3-carboxylic acid
8-Chloro-6-fluoro-1-(2-fluoroethyl)-7-(isoindolin-5-yl)-1,4-dihydro-4-oxoquinoline-3-carboxylic acid
8-Chloro-6-fluoro-1-(2-fluoroethyl)-7-(2-methylisoindolin-5-yl)-1,4-dihydro-4-oxoquinoline-3-carboxylic acid
6,8-Difluoro-1-(2-fluoroethyl)-7-(isoindolin-5-yl)-1,4-dihydro-4-oxoquinoline-3-carboxylic acid
6,8-Difluoro-1-(2-fluoroethyl)-7-(2-methylisoindolin-5-yl)-1,4-dihydro-4-oxoquinoline-3-carboxylic acid
6-Fluoro-1-(2-fluoroethyl)-7-(isoindolin-5-yl)-1,4-dihydro-4-oxo-1,8-naphthyridine-3-carboxylic acid
6-Fluoro-1-(2-fluoroethyl)-7-(2-methylisoindolin-5-yl)-1,4-dihydro-4-oxo-1,8-naphthyridine-3-carboxylic acid
6-Fluoro-7-(isoindolin-5-yl)-8-methyl-1-(oxetan-3-yl)-1,4-dihydro-4-oxoquinoline-3-carboxylic acid
6-Fluoro-7-(isoindolin-5-yl)-1-(oxetan-3-yl)-1,4-dihydro-4-oxoquinoline-3-carboxylic acid
6-Fluoro-7-(isoindolin-5-yl)-8-methoxy-1-(oxetan-3-yl)-1,4-dihydro-4-oxoquinoline-3-carboxylic acid
8-Chloro-6-fluoro-7-(isoindolin-5-yl)-1-(oxetan-3-yl)-1,4-dihydro-4-oxoquinoline-3-carboxylic acid
6,8-Difluoro-7-(isoindolin-5-yl)-1-(oxetan-3-yl)-1,4-dihydro-4-oxoquinoline-3-carboxylic acid
6-Fluoro-7-(isoindolin-5-yl)-1-(oxetan-3-yl)-1,4-dihydro-4-oxo-1,8-naphthyridine-3-carboxylic acid
6-Fluoro-7-(isoindolin-5-yl)-1-(isoxazol-3-yl)-8-methyl-1,4-dihydro-4-oxoquinoline-3-carboxylic acid
6-fluoro-7-(isoindolin-5-yl)-1-(isoxazol-3-yl)-1,4-dihydro-4-oxoquinoline-3-carboxylic acid
6-Fluoro-7-(isoindolin-5-yl)-1-(isoxazol-3-yl)-8-methoxy-1,4-dihydro-4-oxoquinoline-3-carboxylic acid 8-Chloro-6-fluoro-7-(isoindolin-5-yl)-1-(isoxazol-3-yl)-1,4-dihydro-4-oxoquinoline-3-carboxylic acid 6,8-Difluoro-7-(isoindolin-5-yl)-1-(isoxazol-3-yl)-1,4-dihydro-4-oxoquinoline-3-carboxylic acid 6-Fluoro-7-(isoindolin-5-yl)-1-(isoxazol-3-yl)-1,4-dihydro-4-oxo-1,8-naphthyridine-3-carboxylic acid 1-Cyclopropyl-6-fluoro-8-methoxy-7-(3-methylisoindolin-5-yl)-1,4-dihydro-4-oxoquinoline-3-carboxylic acid 1-Cyclopropyl-7-(1,3-dimethylisoindolin-5-yl)-6-fluoro-8-methoxy-1,4-dihydro-4-oxoquinoline-3-carboxylic acid 1-Cyclopropyl-6-fluoro-8-methoxy-7-(1-methylisoindolin-5-yl)-1,4-dihydro-4-oxoquinoline-3-carboxylic acid 1-Cyclopropyl-6-fluoro-8-methoxy-7-[spiro[isoindolin-1,1'-cyclopropan]-5-yl]-1,4-dihydro-4-oxoquinoline-3-carboxylic acid 1-Cyclopropyl-6-fluoro-7-(1-iminoisoindolin-5-yl)-8-methoxy-1,4-dihydro-4-oxoquinoline-3-carboxylic acid 1-Cyclopropyl-7-(4,7-difluoroisoindolin-5-yl)-6-fluoro-8-methoxy-1,4-dihydro-4-oxoquinoline-3-carboxylic acid 5-Amino-1-cyclopropyl-6-fluoro-7-(isoindolin-5-yl)-8-methoxy-1,4-dihydro-4-oxoquinoline-3-carboxylic acid 1-Cyclopropyl-6-fluoro-7-(4-fluoroisoindolin-5-yl)-8-methoxy-1,4-dihydro-4-oxoquinoline-3-carboxylic acid 1-Cyclopropyl-8-difluoromethoxy-6-fluoro-7-(3-methylisoindolin-5-yl)-1,4-dihydro-4-oxoquinoline-3-carboxylic acid 1-Cyclopropyl-8-difluoromethoxy-7-(1,3-dimethylisoindolin-5-yl)-6-fluoro-1,4-dihydro-4-oxoquinoline-3-carboxylic acid 1-Cyclopropyl-8-difluoromethoxy-6-fluoro-7-(1-methylisoindolin-5-yl)-1,4-dihydro-4-oxoquinoline-3-carboxylic acid 1-Cyclopropyl-8-difluoromethoxy-6-fluoro-7-[spiro[isoindolin-1,1'-cyclopropan]-5-yl]-1,4-dihydro-4-oxoquinoline-3-carboxylic acid 1-Cyclopropyl-8-difluoromethoxy-6-fluoro-7-(1-iminoisoindolin-5-yl)-1,4-dihydro-4-oxoquinoline-3-carboxylic acid 1-Cyclopropyl-7-(4,7-difluoroisoindolin-5-yl)-8-difluoromethoxy-6-fluoro-1,4-dihydro-4-oxoquinoline-3-carboxylic acid 5-Amino-1-cyclopropyl-8-difluoromethoxy-6-fluoro-7-(isoindolin-5-yl)-1,4-dihydro-4-oxoquinoline-3-carboxylic acid 1-Cyclopropyl-8-difluoromethoxy-6-fluoro-7-(4-fluoroisoindolin-5-yl)-1,4-dihydro-4-oxoquinoline-3-carboxylic acid 1-Cyclopropyl-6-fluoro-7-(4-fluoroisoindolin-5-yl)-1,4-dihydro-4-oxoquinoline-3-carboxylic acid 1-Cyclopropyl-7-(4,7-difluoroisoindolin-5-yl)-6-fluoro-1,4-dihydro-4-oxoquinoline-3-carboxylic acid 1-Cyclopropyl-6-fluoro-8-fluoromethyl-7-(isoindolin-5-yl)-1,4-dihydro-4-oxoquinoline-3-carboxylic acid 1-Cyclopropyl-6-fluoro-8-fluoromethyl-7-(2-methylisoindolin-5-yl)-1,4-dihydro-4-oxoquinoline-3-carboxylic acid 1-Cyclopropyl-7-(1,3-dimethylisoindolin-5-yl)-6-fluoro-8-fluoromethyl-1,4-dihydro-4-oxoquinoline-3-carboxylic acid 1-Cyclopropyl-8-difluoromethyl-6-fluoro-7-(isoindolin-5-yl)-1,4-dihydro-4-oxoquinoline-3-carboxylic acid 1-Cyclopropyl-8-difluoromethyl-6-fluoro-7-(2-methylisoindolin-5-yl)-1,4-dihydro-4-oxoquinoline-3-carboxylic acid 1-Cyclopropyl-8-difluoromethyl-7-(1,3-dimethylisoindolin-5-yl)-6-fluoro-1,4-dihydro-4-oxoquinoline-3-carboxylic acid 1-Cyclopropyl-6-fluoro-7-(isoindolin-5-yl)-8-trifluoromethyl-1,4-dihydro-4-oxoquinoline-3-carboxylic acid 1-Cyclopropyl-6-fluoro-7-(2-methylisoindolin-5-yl)-8-trifluoromethyl-1,4-dihydro-4-oxoquinoline-3-carboxylic acid 1-Cyclopropyl-7-(1,3-dimethylisoindolin-5-yl)-6-fluoro-8-trifluoromethyl-1,4-dihydro-4-oxoquinoline-3-carboxylic acid 1-Cyclopropyl-6-fluoro-7-(isoindolin-5-yl)-5,8-dimethyl-1,4-dihydro-4-oxoquinoline-3-carboxylic acid 1-Cyclopropyl-6-fluoro-5,8-dimethyl-7-(2-methylisoindolin-5-yl)-1,4-dihydro-4-oxoquinoline-3-carboxylic acid 1-Cyclopropyl-6-fluoro-5,8-dimethyl-7-(1,3-dimethylisoindolin-5-yl)-1,4-dihydro-4-oxoquinoline-3-carboxylic acid 8-Chloro-1-cyclopropyl-7-(isoindolin-5-yl)-1,4-dihydro-4-oxoquinoline-3-carboxylic acid 1-cyclopropyl-8-fluoro-7-(isoindolin-5-yl)-1,4-dihydro-4-oxoquinoline-3-carboxylic acid 1-cyclopropyl-7-(isoindoline-5-yl)-8-methyl-1,4-dihydro-4-oxoquinoline-3-carboxylic acid.

When the compound of the general formula [1] or its salt has isomers (for example, optical isomers, geometrical isomers, tautomers and the like), this invention includes these isomers, and also the compound or its salt may be in the form of a solvate or hydrate and in the various crystal forms.

Processes for producing the compound of this invention are explained below.

The compound of this invention can be synthesized according to, for example, the following production processes.

[Production Process 1]

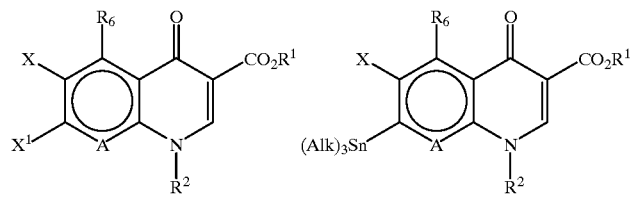

[2] or its salt

[4] or its salt

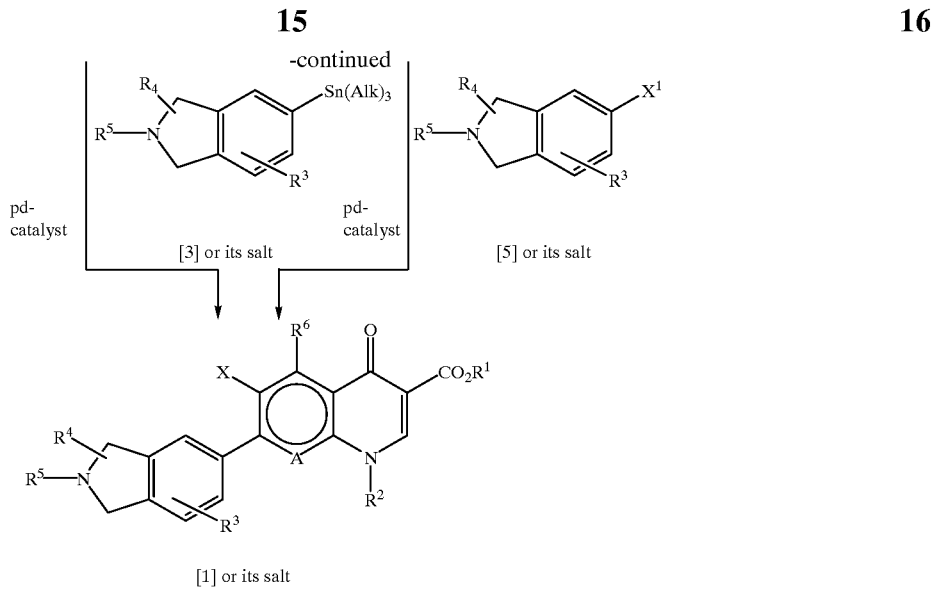

[1] or its salt

In the above general formulas [1], [2], [3], [4] and [5], R¹, R², R³, R⁴, R⁵, R⁶,

and X are as defined above; X¹ represents a chlorine atom, a bromine atom or an iodine atom; and Alk represents a straight chain or branched chain alkyl group having 1 to 6 carbon atoms.

The salts of the compounds of the general formulas [2], [3], [4] and [5] include the same salts as mentioned as to the compound of the general formula [1].

The compound of the general formula [1] or its salt can be obtained by subjecting to coupling reaction with a compound of the general formula [2] or its salt and an organotin compound of the general formula [3] or its salt or an organotin compound of the general formula [4] or its salt and a compound of the general formula [5] or its salt in the presence or absence of a silver oxide using a palladium complex catalyst. A solvent used in this reaction may be any solvent as far as it does not adversely affect the reaction. As the solvent, there are mentioned, for example, aromatic hydrocarbons such as benzene, toluene, xylene and the like; ethers such as dioxane, tetrahydrofuran, anisole, diethylene glycol diethyl ether, dimethyl Cellosolve and the like; nitrites such as acetonitrile and the like; amides such as N,N-dimethylformamide, N,N-dimethylacetamide and the like; sulfoxides such as dimethylsulfoxide and the like, and these solvents may be used alone or in admixture of two or more.

The palladium complex catalyst used in this reaction includes, for example, $PdCl_2(PPh_3)_2$, $Pd(PPh_3)_4$, $PdCl_2[P(O\text{-tolyl})_3]_2$, $PdCl_2 + 2P(OEt)_3$ and $PdCl_2(PhCN)_2$ in which Ph represents a phenyl group.

The amount of the organotin compound of the general formula [3] or its salt used is at least one mole, preferably 1.0 to 2.0 moles, per mole of the compound of the general formula [2] or its salt, and the amount of the compound of the general formula [5] or its salt used is at least one mole, preferably 1.0 to 5.0 moles, per mole of the organotin compound of the general formula [4] or its salt.

This coupling reaction may usually be effected at a temperature of 50 to 170° C. for a period of one minute to 24 hours under an atmosphere of an inert gas (for example, argon, nitrogen).

The thus obtained compound of the general formula [1] or its salt can be converted into another compound of the general formula [1] or its salt by subjecting the former to a reaction known per se such as oxidation, reduction, rearrangement, substitution, halogenation, dehydration, hydrolysis or the like or to an appropriate combination of these reactions.

If the compounds of the general formulas [2], [3], [4] and [5] or their salts to be used in the above-mentioned production processes have isomers (for example, optical isomers, geometrical isomers, tautomers or the like), these isomers may be substituted therefor. Also, the above compounds or their salts may be used in the form of a solvate or hydrate or in various crystal forms.

When the compounds of the general formulas [1], [2], [3], [4] and [5] or their salts have an amino, hydroxyl or carboxyl group, it is possible to previously protect the group with a conventional protecting group and remove the protecting group, after the reaction, in a manner known per se.

Next, processes for producing the compounds of the general formulas [2], [3], [4] and [5] or their salts which are the starting materials for producing the compound of this invention are explained below. The organotin compounds of the general formulas [3] and [4] or their salts are novel compounds.

First of all, the compound of the general formula [2] or its salt and the organotin compound of the general formula [4] or its salt can be synthesized according to, for example, the following production processes.

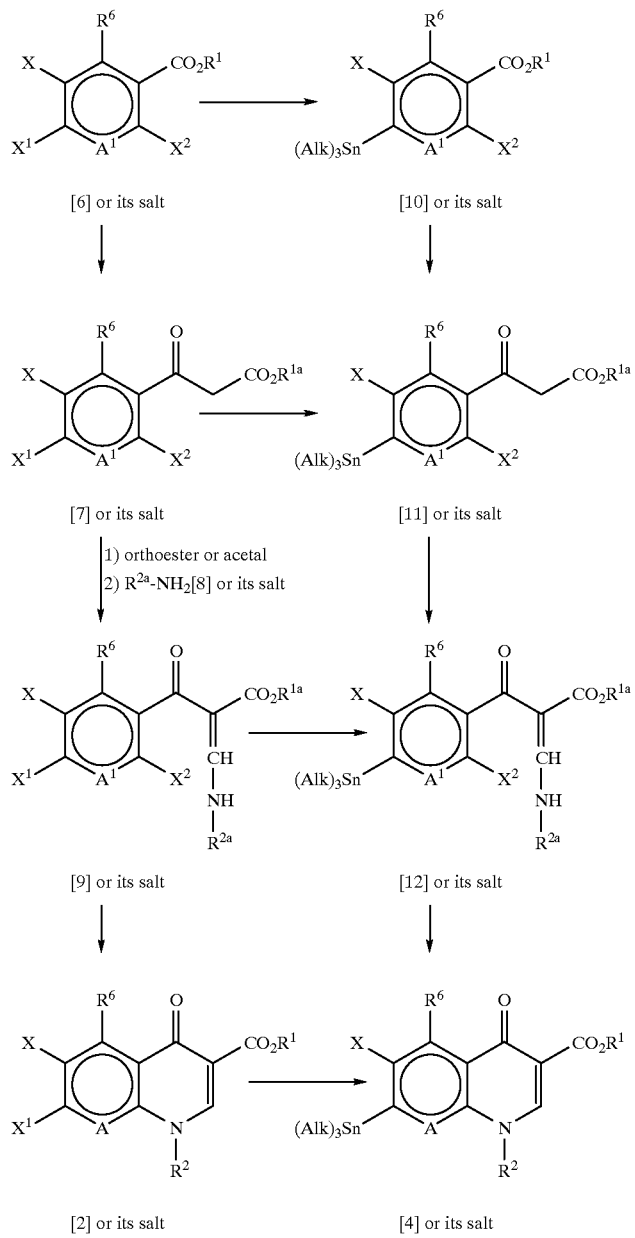

[6] or its salt
[10] or its salt
[7] or its salt
[11] or its salt 1) orthoester or acetal
2) $R^{2a}$-$NH_2$[8] or its salt

[9] or its salt
[12] or its salt
[2] or its salt
[4] or its salt

In the above general formulas [2], [4], [6], [7], [8], [9], [10], [11] and [12], $R^1$, $R^2$, $R^6$,

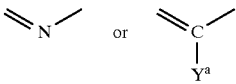

and Alk have the same meanings as mentioned above; $R^{1a}$ represents the same carboxyl-protecting group as $R^1$; $R^{2a}$ represents the same substituted or unsubstituted alkyl, alkenyl, cycloalkyl, aryl or heterocyclic group as $R^2$;

$$\underset{A^1}{\diagdown\mkern-14mu\diagup}$$

is a group represented by the formula:

$$\underset{N}{\diagdown\mkern-14mu\diagup} \quad \text{or} \quad \underset{\underset{Y^a}{|}}{C}\diagdown\mkern-14mu\diagup$$

in which $Y^a$ represents a hydrogen atom, a halogen atom, a substituted or unsubstituted alkyl, alkoxy or alkylthio group or a protected or unprotected hydroxyl group; and $X^2$ represents a halogen atom.

The salts of the compounds of the general formulas [6], [7], [8], [9], [10], [11] and [12] include the same salts as explained as to the compound of the general formula [1].

Each step is explained below.

(1) The compound of the general formula [7] or its salt or the compound of the general formula [11] or its salt can usually be obtained by subjecting a compound of the general formula [6] or its salt or a compound of the general formula [10] or its salt, respectively, to keto-esterification known in the art.

(a) For example, according to the method described in Angewant Chemie, International Edition in English, vol 18, page 72 (1979), the carboxyl group of the compound of the general formula [6] or its salt or the carboxyl group of the compound of the general formula [10] or its salt is reacted with, for example, N,N'-carbonyl diimidazole to convert the compound to an active acid amide, and thereafter, the active acid amide is reacted with a magnesium salt of a malonic acid monoester to obtain the compound of the general formula [7] or its salt or the compound of the general formula [11] or its salt, respectively. The solvent used in the reaction of the active acid amide with the magnesium salt of malonic acid monoester may be any solvent as far as it does not adversely affect the reaction and includes, for example, aromatic hydrocarbons such as benzene, toluene, xylene and the like; ethers such as dioxane, tetrahydrofuran, diethyl ether and the like; halogenated hydrocarbons such as methylene chloride, chloroform, dichloroethane and the like; and amides such as N,N-dimethylformamide, N,N-dimethylacetamide and the like. These solvents may be used alone or in admixture of two or more. The amount of each of the N,N'-carbonyl diimidazole and the magnesium salt of malonic acid monoester used is at least one mole respectively, preferably one to two moles, per mole of the compound of the general formula [6] or [10] or its salt. These reactions may be usually carried out at a temperature of 0–100° C., preferably 10–80° C., for a period of 5 minutes to 30 hours.

(b) As another method, the carboxyl group of the compound of the general formula [6] or its salt or the carboxyl group of the compound of the general formula [10] or its salt is reacted with a halogenating agent such as thionyl chloride to be converted to an acid halide, and thereafter, the acid halide is reacted with a metal salt of malonic diester such as sodium or ethoxymagnesium salt of malonic diester or the like, after which the reaction mixture is subjected to partial removal of the carboxyl-protecting group using p-toluenesulfonic acid or trifluoroacetic acid in a hydrous solvent and decarboxylation, whereby a compound of the general formula [7] or its salt or the compound of the general formula [11] or its salt can be obtained, respectively. The solvent used in the reaction of the acid halide with the metal salt of malonic diester may be any solvent as far as it does not adversely affect the reaction, and includes specifically the same solvents as mentioned in (1) (a) above. The amount of the metal salt of malonic acid diester used is at least one mole, preferably one to three moles, per mole of the compound of the general formula [6] or [10] or its salt. This reaction may be usually carried out at a temperature of −50–100° C., for a period of 5 minutes to 30 hours.

(2) (a) The compound of the general formula [9] or its salt or the compound of the general formula [12] or its salt can be obtained, respectively, by reacting a compound of the general formula [7] or its salt or a compound of the general formula [11] or its salt with an orthoester such as methyl orthoformate, ethyl orthoformate or the like in acetic anhydride and then with a compound of the general formula [8] or its salt. The solvent used in these reactions may be any solvent as far as it does not adversely affect the reaction and includes, for example, aromatic hydrocarbons such as benzene, toluene, xylene and the like; ethers such as dioxane, tetrahydrofuran, anisole, diethylene glycol diethyl ether, dimethyl Cellosolve and the like; alcohols such as methanol, ethanol, propanol and the like; halogenated hydrocarbons such as methylene chloride, chloroform, dichloroethane and the like; amides such as N,N-dimethylformamide, N,N-dimethylacetamide and the like; sulfoxides such as dimethyl sulfoxide and the like; etc. These solvents may be used alone or in ad-mixture of two or more. The amount of the orthoester used is at least one mole respectively, preferably one to ten moles, per mole of the compound of the general formula [7] or [11] or its salt. These reactions may be usually carried out at a temperature of 0–150° C., preferably 50–150° C., for a period of 20 minutes to 50 hours.

In the subsequent reaction with the compound of the general formula [8] or its salt, the compound of the general formula [8] or its salt may be used in an amount of at least one mole per mole of the compound of the general formula [7] or [11] or its salt, and these reactions may be usually carried out at a temperature of 0–100° C., preferably 10–60° C., for a period of 20 minutes to 30 hours.

(b) As another method, the compound of the general formula [7] or its salt or the compound of the general formula [11] or its salt is reacted with an acetal such as N,N-dimethylformamide dimethyl acetal, N,N-dimethylformamide diethyl acetal or the like in the presence or absence of an acid anhydride such as acetic anhydride or the like and then with a compound of the general formula [8] or its salt to be converted to a compound of the general formula [9] or its salt or a compound of the general formula [12] or its salt, respectively. The solvent used in the above reactions may be any solvent as far as it does not adversely affect the reaction, and includes specifically the same solvents as mentioned in (2) (a) above. The amount of the acetal used is at least one mole, preferably about one to five moles, per mole of the compound of the general formula [7] or [11] or its salt. The reaction with the acetal may be usually carried out at a temperature of 0–100° C., preferably 20–85° C., for a period of 20 minutes to 50 hours.

In the subsequent reaction with the compound of the general formula [8] or its salt, the amount of the compound of the general formula [8] or its salt used is at least one mole per mole of the compound of the general formula [7] or [11] or its salt, and these reactions may be usually carried out at a temperature of 0–100° C., preferably 10–60° C., for a period of 20 minutes to 30 hours.

(3) The compound of the general formula [2] or its salt or the compound of the general formula [4] or its salt can be obtained by subjecting the compound of the general formula [9] or its salt or the compound of the general formula [12] or its salt, respectively, to ring-closure reaction in the presence or absence of a fluoride salt or a base. The solvent used in these reactions may be any solvent as far as it does not adversely affect the reaction, and includes, for example, amides such as N,N-dimethylformamide, N,N-dimethylacetamide and the like; ethers such as dioxane, anisole, diethylene glycol dimethyl ether, dimethyl Cellosolve and the like; sulfoxides such as dimethyl sulfoxide and the like; etc. These solvents may be used alone or in admixture of two or more. The fluoride salt which is used as desired includes, for example, sodium fluoride, potassium fluoride and the like, and the base which is used as desired includes, for example, sodium hydrogen-carbonate, potassium carbonate, potassium tert-butoxide, sodium hydride and the like. The amount of the fluoride salt or base used is at least one mole respectively, preferably 1.0–3.0 moles, per mole of the compound of the general formula [9] or [12] or its salt. These reactions may be usually carried out at a temperature of 0–180° C. for a period of 5 minutes to 30 hours.

Incidentally, the compound of the general formula [2] or [4] in which

is a group represented by the formula:

in which Y' forms a group represented by the following formula together with $R^2$:

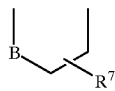

in which B and $R^7$ have the same meanings as mentioned above can be specifically prepared according to the method stated in Japanese Patent Application Kokai No. 2-85,255 or the like.

The aryltin compound of the general formula [10] or its salt, the aryltin compound of the general formula [11] or its salt or the aryltin compound of the general formula [4] or its salt can be obtained by reacting the halogenated aryl compound of the general formula [6] or its salt, the halogenated aryl compound of the general formula [7] or its salt or the halogenated aryl compound of the general formula [2] or its salt, respectively, with a hexaalkyldistannane using a palladium complex catalyst according to the method stated in, for example, Bulletin of the Chemical Society of Japan, vol 56, pages 3855–3856 (1983). The solvent and palladium complex catalyst used may be those which do not adversely affect the reaction and are not particularly limited. Specific examples thereof are the same as mentioned in the Production Process 1 above. The amount of the hexaalkyldistannane used is at least one mole, preferably 1.0–3.0 moles, per mole of the halogenated aryl compound of the general formula [6], [7] or [2] or its salt. This reaction may be usually carried out at a temperature of 40–160° C. for a period of 1–72 hours.

In the production route, when the compound of the general formula [2], [4], [6], [7], [8], [9], [10], [11] or [12] or its salt has an amino, hydroxyl or carboxyl group, it is possible to previously protect this group with a conventional protecting group and remove the protecting group, after completion of the reaction, in a manner known per se.

When the compound of the general formula [2], [4], [6], [7], [8], [9], [10], [11] or [12] or its salt used in the above-mentioned production processes has isomers (for example, optical isomers, geometrical isomers, tautomers or the like), these isomers may be substituted therefor. Also, the above compound or its salt may be used in the form of a solvate or hydrate or in the desired crystal form. After completion of the reaction, the reaction mixture may be used as it is without isolating the objective compound in the subsequent reaction.

The compound of the general formula [6] or its salt and the compound of the general formula [2] or its salt which are one of the starting materials for producing the compound of this invention can be synthesized from a known compound by converting it to a compound having the desired $X^1$ by the method stated in, for example, Japanese Patent Application Kokai No. 1-100,166, namely utilizing the Sandmeyer reaction.

Subsequently, the organotin compound of the general formula [3] or its salt can be synthesized according to, for example, the following synthesis method:

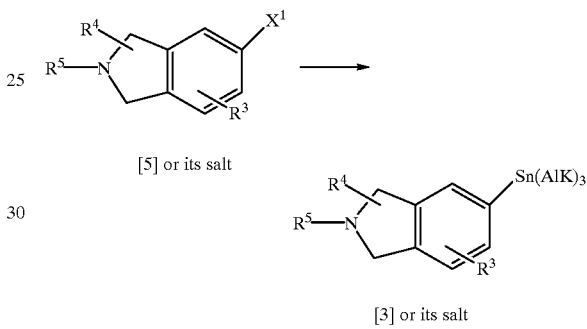

wherein $R^3$, $R^4$, $R^5$, $X^1$ and Alk have the same meanings as mentioned above.

The compound of the general formula [3] or its salt can be obtained by reacting a compound of the general formula [5] or its salt with a hexaalkyldistannane using a palladium complex catalyst according to the above-mentioned method.

In the above-mentioned production processes, when the compound of the general formula [3] or [5] or its salt has isomers (for example, optical isomers, geometrical isomers, tautomers or the like), these isomers may be substituted therefor and also the above compound or its salt may be used in the form of a solvate or hydrate or in the various crystal forms.

When the compound of the general formula [3] or [5] or its salt has an amino or hydroxyl group, it is possible to previously protect this group with a conventional protecting group and remove the protecting group, after completion of the reaction, in a manner known per se.

The isoindoline halide compound represented by the general formula [5] or its salt which is one of the starting materials for producing the compound of this invention can be synthesized by the following synthesis methods according to, for example, the method of Organic Synthesis, vol. 5, pages 1064–1066, the method stated in Japanese Patent Application Kokai No. 63-179,872, Japanese Patent Application Kokai No. 2-62,875 or Japanese Patent Application Kokai No. 3-52,888 or Arzniem.Forsh./Drug Res. 30(II), 1487–1493 (1980) or the like method.

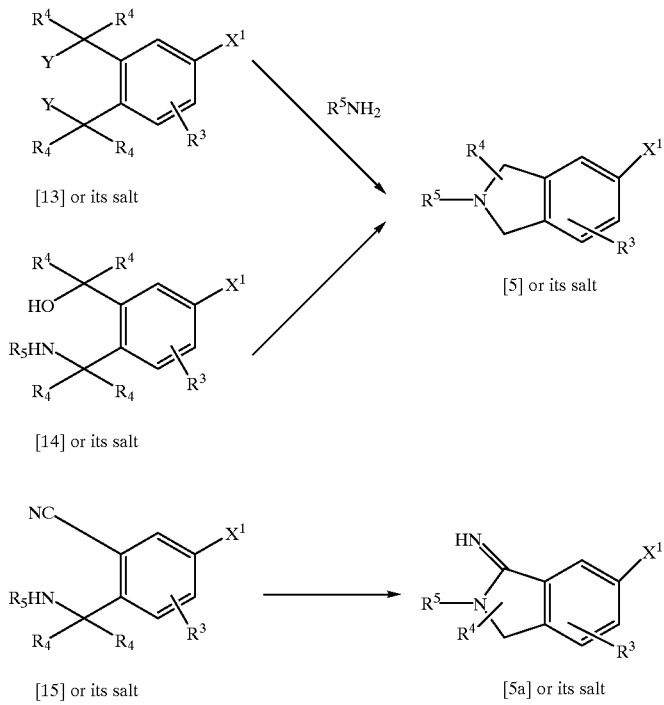

[13] or its salt

[14] or its salt

[15] or its salt

[5] or its salt

[5a] or its salt wherein $R^3$, $R^4$, $R^5$ and $X^1$ have the same meanings as mentioned above and Y represents a removing group.

The salts of the compounds of the general formulas [13], [14], [15] and [5a] include the same salts as mentioned as to the compound of the general formula [1]. The removing group for Y includes halogen atoms such as a chlorine atom, a bromine atom and the like.

The compound of the general formula [5] or its salt can be obtained by reacting a compound of the general formula [13] or its salt with $R^5NH_2$ or by subjecting a compound of the general formula [14] or its salt to dehydration reaction. On the other hand, the compound of the general formula [5a] or its salt, which has an imino group, can be obtained by subjecting a compound of the general formula [15] or its salt to ring-closure reaction. Furthermore, a compound of the general formula [13], [14] or [15] or its salt and an organotin compound derived from the compound of the general formula [13], [14] or [15] or its salt is subjected to coupling reaction with a compound of the general formula [4] or [2] or its salt according to the same method as mentioned in the Production Process 1 above, and the compound obtained is subjected to isoindoline ring formation reaction according to the same method as mentioned above to obtain the compound of the general formula [1] or its salt.

In the production processes mentioned above, when the compound of the general formula [13], [14], [15] or [5a] or its salt has isomers (optical isomers, geometrical isomers, tautomers or the like), these isomers may be substituted therefor, and the compound or its salt may be used in the form of a solvate or hydrate or in the various crystal forms.

When the compound of the general formula [13], [14], [15] or [5a] or its salt has an amino or hydroxyl group, it is possible to previously protect this group with a conventional protecting group and remove the protecting group, after the reaction, in a manner known per se.

The compound of the general formula [1] or its salt can also be produced by another production process as shown below.

[Production Process 2]

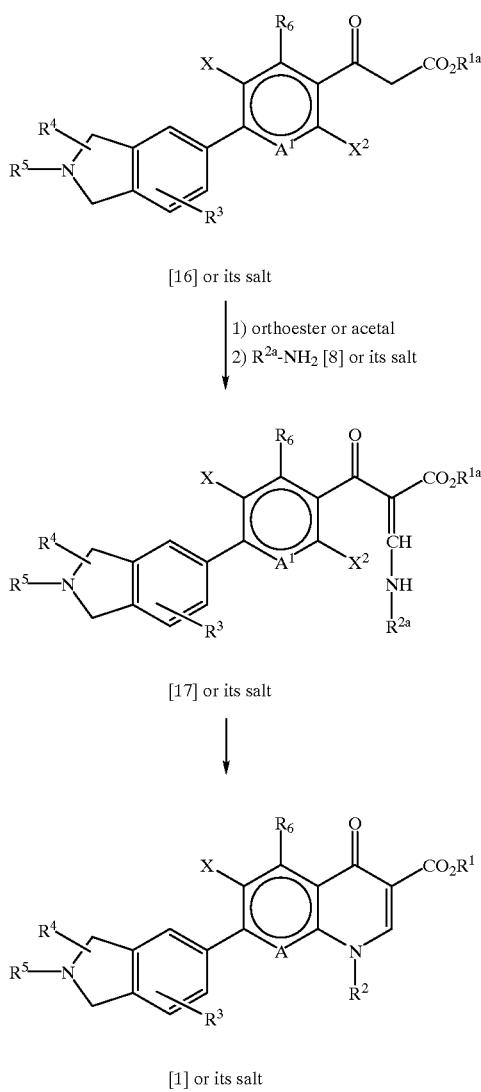

[16] or its salt 1) orthoester or acetal
2) $R^{2a}-NH_2$ [8] or its salt

[17] or its salt

[1] or its salt wherein $R^1$, $R^{1a}$, $R^2$, $R^{2a}$, $R^3$, $R^4$, $R^5$, $R^6$,

X and $X^2$ have the same meanings as mentioned above.

The salts of the compound of the general formula [16] or [17] includes the same salts as mentioned as to the compound of the general formula [1].

The compound of the general formula [1] or its salt can be obtained from the compound of the general formula [16] or its salt according to the above-mentioned method (the synthesis of the general formula [2] or [4] or its salt from the compound of the general formula [7] or [11] or its salt). That is to say, the compound of the general formula [1] or its salt can be obtained by reacting the compound of the general formula [16] or its salt with an orthoester or an acetal in the presence or absence of an acid anhydride such as acetic anhydride, then with the compound of the general formula [8] or its salt to produce a compound of the general formula [17] or its salt and subsequently subjecting the compound of the general formula [17] or its salt to ring-closure reaction in the presence or absence of a fluoride salt or a base.

The compound of the general formula [1] or its salt thus obtained can be converted to another compound of the general formula [1] or its salt by subjecting the former to a reaction known per se such as oxidation, reduction, rearrangement, substitution, halogenation, dehydration, hydrolysis or the like or to an appropriate combination of these reactions.

In the production processes mentioned above, hen the compound of the general formula [8], [16] or [17] or its salt has isomers (optical isomers, geometrical isomers, tautomers or the like), these isomers may be substituted therefor, and the compound or its salt may be used in the form of a solvate or hydrate or in the desired crystal form.

When the compound of the general formula [8], [16], [17] or [1] or its salt has an amino, hydroxyl or carboxyl group, it is possible to previously protect the group with a conventional protecting group and remove the protecting group, after completion of the reaction, in a manner known per se. After completion of the reaction, the reaction mixture may be used as it is in the subsequent reaction without isolating the objective compound.

Next, the compound of the general formula [16] or its salt which is one of the starting materials for producing the compound of this invention is explained. The compound of the general formula [16] or its salt is novel and can be synthesized according to, for example, the following production processes.

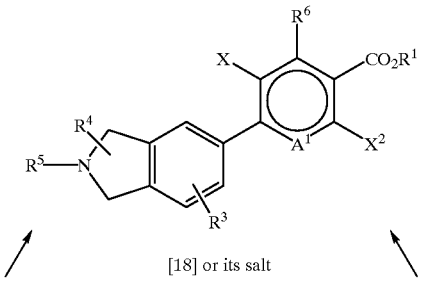

[18] or its salt

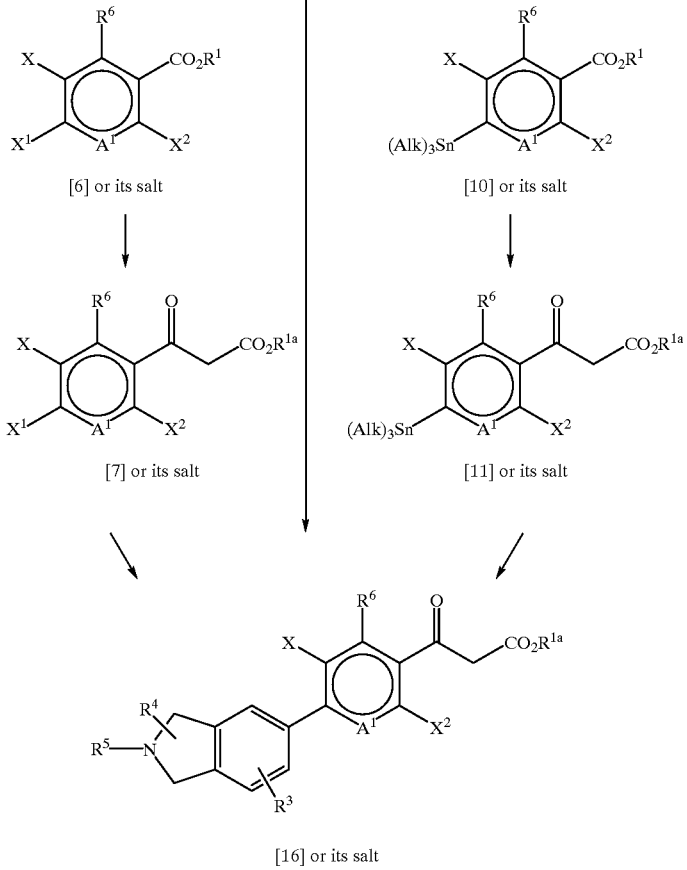

[16] or its salt

In the above formulas [6], [7], [10], [11], [16] and [18], $R^1$, $R^{1a}$, $R^3$, $R^4$, $R^5$, $R^6$,

$X$, $X^1$, $X^2$ and Alk have the same meanings as mentioned above.

The salt of the compound of the general formula [18] include the same salts as mentioned as to the compound of the general formula [1].

The compound of the general formula [16] or its salt can be produced from the compound of the general formula [7] or [11] or its salt according to the same method as mentioned in the Production Process 1 above or can also be produced by subjecting the compound of the general formula [18] or its salt to ketoesterification reaction according to the above-mentioned method.

The compound of the general formula [7] or its salt or the compound of the general formula [11] or its salt can be obtained by subjecting the compound of the general formula [6] or its salt or the compound of the general formula [10] or its salt, respectively, to ketoesterification reaction according to the above-mentioned method. On the other hand, the compound of the general formula [18] or its salt can be produced from the compound of the general formula [6] or [10] or its salt according to the same method as mentioned in the Production Process 1 above.

When the compound of the general formula [6], [7], [10], [11], [16] or [18] or its salt has an amino, hydroxyl or carboxyl group, it is possible to previously protect the group with a conventional protecting group and remove the protecting group, after the reaction, in a manner known per se.

In the above-mentioned production processes, when the compound of the general formula [6], [7], [10], [11], [16] or [18] or its salt has isomers (optical isomers, geometrical isomers, tautomers or the like), these isomers may be substituted therefor, and the compound or its salt may be used in the form of a solvate or hydrate or in the desired crystal form. After completion of the reaction, the reaction mixture may be used as it is in the subsequent reaction without isolating the objective compound.

The compound of the general formula [1] or its salt thus obtained can be isolated and purified according to a conventional method such as extraction, crystallization, column chromatography or the like.

When the compound of this invention is used as a drug or medicine, the compound may be mixed with a preparation adjuvant such as an excipient, a carrier or a diluent which is used in conventional pharmaceutical preparations and can be orally or parenterally administered in the form of a tablet, capsule, powder, syrup, granule, pill, dispersion, emulsion, solution, suppository, ointment, injection or the like. The administration route, dosage and number of administrations can be appropriately varied depending upon the age, weight and symptom of a patient. Usually, it is sufficient to administer the compound to an adult by an oral or parenteral administration (for example, by injection, drip infusion, intrarectal administration or the like) in a proportion of 0.1–100 mg/kg/day in one to several portions.

Next, the pharmacological activities of representative compounds of this invention are explained.

Antibacterial activity

Test method

According to the standard method of Japan Society of Chemotherapy [CHEMOTHERAPY, vol. 29, No. 1, pages 76–79 (1981)], a loop of a bacterial solution obtained by culturing in Mueller Hinton broth (manufactured by Difco] at 37° C. for 20 hours and adjusted to a concentration of $10^6$ cells/plate ($10^8$ cells/ml) was inoculated onto a Mueller Hinton agar medium (manufactured by Difco) containing the test compound and cultured at 37° C. for 20 hours, and thereafter, the growth of the bacterial was observed to determine the minimum concentration at which the growth of the bacteria was inhibited, which concentration is indicated as MIC ($\mu$g/ml).

The test results are shown in Table 1.

Incidentally, the asterisks in Table 1 have the following meanings:

*: β-lactamase-producing bacteria

**: MRSA (methicillin-resistant S. aureus)

Test Compound A: 1-cyclopropyl-6-fluoro-7-(isoindolin-5-yl)-8-methyl-1,4-dihydro-4-oxoquinoline-3-carboxylic acid.

Control Compound B: 1-cyclopropyl-6-fluoro-7-(1-piperazinyl)-1,4-dihydro-4-oxoquinoline-3-carboxylic acid (Ciprofloxacin).

TABLE 1

|  | MIC ($\mu$g/ml) | |
| --- | --- | --- |
|  | A | B |
| S. aureus FDA 209P | ≦0.05 | 0.2 |
| S. aureus F-137* | ≦0.05 | 0.39 |
| S. aureus F-597** | ≦0.05 | 6.25 |
| E. coli NIHJ JC-2 | ≦0.05 | ≦0.05 |

From the above results, it can be understood that the compound of this invention exhibits excellent antibacterial activity.

Best Mode for Carrying Out the Invention

This invention is explained in more detail below referring to Reference Examples and Examples; however, this invention should not be construed to be limited thereto.

Incidentally, the mixing ratio in the eluent is by volume unless otherwise specified. The carrier used in the column chromatography was Silica gel 60, No. 7734 (manufactured by MERCK & CO., INC.). Also, in the Reference Examples and the Examples, the term "$d_1$-TFA" means a trifluoroacetic acid-$d_1$ and "$d_6$-DMSO" means a dimethylsulfoxide-$d_6$.

Reference Example 1

In 30 ml of toluene was dissolved 3.04 g of ethyl 3-bromo-2,4,5-trifluorobenzoate, and to the solution were added 5.11 g of tributylvinyltin and 0.25 g of tetrakis (triphenylphosphine) palladium (0), after which the resulting mixture was heated under reflux for two hours under a nitrogen atmosphere. The reaction mixture was concentrated under reduced pressure, and the residue obtained was purified by a column chromatography (eluent: n-hexane:ethyl acetate=100:1), to obtain a colorless, oily ethyl 2,4,5-trifluoro-3-vinylbenzoate. The oily product thus obtained was dissolved in a mixed solvent of 62 ml of methanol and 12 ml of methylene chloride, and thereafter, at −50° C., an ozone gas was blown thereinto for three hours and subsequently a nitrogen gas was blown thereinto for 30 minutes. The temperature of this solution was elevated to −20° C., and thereafter, 0.81 g of sodium borohydride was added thereto, after which the resulting mixture was stirred at room temperature for 12 hours. The reaction mixture was added to a mixed solvent of 400 ml of ethyl acetate and 600 ml of ice water and the pH was adjusted to 1 with 6N hydrochloric acid, after which the organic layer formed was separated, washed with a saturated saline solution and then dried over anhydrous magnesium sulfate. The solvent was then removed by distillation under reduced pressure. The residue thus obtained was purified by a column chromatography (eluent: n-hexane:ethyl acetate=4:1), to obtain 1.70 g of a colorless, oily ethyl 3-hydroxymethyl-2,4,5-trifluorobenzoate.

IR (neat) cm$^{-1}$: $\nu_{C=O}$ 1720

NMR (CDCl$_3$) δ values: 1.38 (3H, t, J=6.8 Hz), 2.60 (1H, t, J=5.0 Hz), 4.39 (2H, q, J=6.8 Hz), 4.65–4.95 (2H, m), 7.40–8.00 (1H, m)

Reference Example 2

(1) In 308 ml of dimethyl sulfoxide was dissolved 61.7 g of ethyl 2,4,5-trifluoro-3-methylbenzoate, and 42.3 g of sodium azide was added to the solution, after which the resulting mixture was stirred at 55° C. for 14 hours. The reaction mixture was cooled to room temperature and thereafter added to a mixed solvent of 500 ml of ethyl acetate and 1200 ml of water. The organic layer formed was separated, washed with water and then dried over anhydrous magnesium sulfate. The solvent was then removed by distillation under reduced pressure to obtain 65.3 g of pale yellow, oily ethyl 4-azido-2,5-difluoro-3-methylbenzoate.

(2) In 60 ml of methanol was suspended 14.2 g of stannous chloride, and to this suspension was dropwise added a solution of 10.0 g of ethyl 4-azido-2,5-difluoro-3-methylbenzoate in 20 ml of methanol at room temperature over one hour, after which the resulting mixture was stirred at the same temperature for 30 minutes. The methanol was removed by distillation under reduced pressure, and to the residue obtained were added 300 ml of diethyl ether and 100 ml of water, after which the pH was adjusted to 12.5 with 2N aqueous sodium hydroxide solution. The organic layer formed was separated, washed with water and then dried over anhydrous magnesium sulfate. The solvent was then removed by distillation under reduced pressure to obtain 8.91 g of yellow, oily ethyl 4-amino-2,5-difluoro-3-methylbenzoate.

(3) In 50 ml of ethanol was dissolved 8.91 g of ethyl 4-amino-2,5-difluoro-3-methylbenzoate, and 50 ml of 2N aqueous sodium hydroxide solution was added to the solution, after which the resulting mixture was stirred at room temperature for three hours. To the reaction mixture was added 50 ml of 2N hydrochloric acid, and the resulting crystals were collected by filtration, to obtain 5.45 g of colorless, crystalline 4-amino-2,5-difluoro-3-methylbenzoic acid.

IR (KBr) cm$^{-1}$: $\nu_{C=O}$ 1701, 1636

NMR (d$_1$-TFA) δ value: 2.50 (3H, s), 7.86 (1H, dd, J=5.4 Hz, J=9.3 Hz)

Reference Example 3

(1) In 66 ml of dimethyl sulfoxide was dissolved 13.2 g of ethyl 3-difluoromethoxy-2,4,5-trifluorobenzoate, and to this solution was added 7.3 g of sodium azide, after which the resulting mixture was stirred at room temperature for five hours. The reaction mixture was added to a mixed solvent of 150 ml of ethyl acetate and 150 ml of ice water and the pH was adjusted to 2 with 6N hydrochloric acid, after which the organic layer formed was separated, then washed successively with water and a saturated saline solution, and thereafter dried over anhydrous magnesium sulfate. The solvent was then removed by distillation under reduced pressure. The residue obtained was purified by a column chromatography (eluent: n-hexane:ethyl acetate=10:1), to obtain 13.9 g of colorless, oily ethyl 4-azido-2,5-difluoro-3-difluorome-thoxybenzoate.

(2) In 210 ml of ethanol and 70 ml of ethyl acetate was dissolved 13.8 g of ethyl 4-azido-2,5-difluoro-3-difluoromethoxybenzoate, and 1.38 g of 5% palladium-carbon was added to the solution, after which the resulting mixture was stirred at 50° C. for six hours under a hydrogen stream. The reaction mixture was filtered, and the filtrate obtained was concentrated under reduced pressure, to obtain 12.3 g of colorless, crystalline ethyl 4-amino-2,5-difluoro-3-difluoromethoxybenzoate.

(3) In 61 ml of ethanol was suspended 12.3 g of ethyl 4-amino-2,5-difluoro-3-difluoromethoxybenzoate, and 31 ml of 2N aqueous sodium hydroxide solution was added to the suspension, after which the resulting mixture was stirred at 40° C. for one hour. To the reaction mixture was added 35 ml of 2N hydrochloric acid and the precipitate formed was collected by filtration, to obtain 10.6 g of colorless, crystalline 4-amino-2,5-difluoro-3-difluoromethoxybenzoic acid.

IR (KBr) cm$^{-1}$: $\nu_{C=O}$ 1703, 1636

NMR (CDCl$_3$—CD$_3$OD) δ value: 6.62 (1H, t, J=74 Hz), 7.49 (1H, dd, J=6.3 Hz, J=11.7 Hz)

In the same manner, the following compounds were obtained.

4-Amino-2,5-difluoro-3-fluoromethoxybenzoic acid

IR (KBr) cm$^{-1}$: $\nu_{C=O}$ 1705, 1637

NMR (d$_6$-DMSO) δ value: 5.60 (1H, d, J=54 Hz), 6.05 (2H, brs), 7.32 (1H, dd, J=6.1 Hz, J=11.7 Hz)

4-Amino-2,5-difluoro-3-hydroxymethylbenzoic acid

IR (KBr) cm$^{-1}$: $\nu_{C=O}$ 1717, 1639

NMR (CDCl$_3$—CD$_3$OD) δ value: 4.72 (2H, d, J=2.0 Hz), 7.48 (1H, dd, J=6.8 Hz, J=11.7 Hz)

Reference Example 4

In 658 ml of 4.7% hydrobromic acid was suspended 26.3 g of 4-amino-2,5-difluoro-3-methylbenzoic acid, and 161 g of cupric bromide was added to the suspension. To this suspension was dropwise added a solution of 16.5 g of sodium nitrite in 165 ml of water over one hour with ice-cooling, and the resulting mixture was stirred for one hour at the same temperature and then at room temperature for two hours. To the reaction mixture was added 700 ml of toluene and the organic layer formed was separated, washed with 100 ml of conc. hydrochloric acid and then dried over anhydrous magnesium sulfate. The solvent was then removed by distillation under reduced pressure. To the residue obtained was added n-hexane and the resulting crystals were collected by filtration to obtain 29.5 g of colorless, crystalline 4-bromo-2,5-difluoro-3-methylbenzoic acid.

IR (KBr) cm$^{-1}$: $\nu_{C=O}$ 1699

NMR (CDCl$_3$) δ value: 2.41 (3H, d, J=2.9 Hz), 7.57 (1H, dd, J=6.3 Hz, J=7.8 Hz)

In the same manner, the following compounds were obtained.

4-Bromo-2,5-difluoro-3-difluoromethoxybenzoic acid

IR (KBr) cm$^{-1}$: $\nu_{C=O}$ 1718, 1698

NMR (CDCl$_3$—CD$_3$OD) δ value: 6.65 (1H, t, J=74 Hz), 7.66 (1H, dd, J=5.9 Hz, J=8.3 Hz)

4-Bromo-2,5-difluoro-3-fluoromethoxybenzoic acid

IR (KBr) cm$^{-1}$: $\nu_{C=O}$ 1703

NMR (CDCl$_3$) δ value: 5.72 (2H, d, J=53 Hz), 6.33 (1H, brs), 7.63 (1H, dd, J=5.8 Hz, J=8.3 Hz)

4-Bromo-2,5-difluoro-3-hydroxymethylbenzoic acid

IR (KBr) cm$^{-1}$: $\nu_{C=O}$ 1718

NMR (CD$_3$OD) δ value: 4.83 (2H, d, J=2.4 Hz), 7.68 (1H, dd, J=6.1 Hz, J=8.5 Hz)

Reference Example 5

In 8 ml of sulfuric acid was dissolved 2.0 g of 4-bromo-2,5-difluoro-3-methoxybenzoic acid, and 4 ml of nitric acid was dropwise added to the solution with ice-cooling, after which the resulting mixture was stirred at room temperature for one hour. The reaction mixture was added to a mixed solvent of 50 ml of diethyl ether and 50 ml of ice water, and the organic layer formed was separated, washed with a saturated saline solution and then dried over anhydrous magnesium sulfate. The solvent was then removed by distillation under reduced pressure. To the residue thus obtained was added n-hexane, and the resulting crystals were collected by filtration to obtain 1.9 g of pale yellow, crystalline 4-bromo-2,5-difluoro-3-methoxy-6-nitrobenzoic acid.

IR (KBr) cm$^{-1}$: $\nu_{C=O}$ 1718

NMR (CDCl$_3$) δ value: 4.16 (3H, d, J=2.9 Hz), 8.75 (1H, brs)

Reference Example 6

In 100 ml of anhydrous tetrahydrofuran was dissolved 10.0 g of 4-bromo-2,5-difluoro-3-methylbenzoic acid, and 9.69 g of N,N'-carbonyldiimidazole was added to the solution with ice-cooling, after which the resulting mixture was stirred at room temperature for one hour. Subsequently, 8.56 g of magnesium ethoxycarbonylacetate was added to the mixture and the resulting mixture was stirred at the same temperature for 20 hours. The reaction mixture was added to a mixed solvent of 200 ml of ethyl acetate and 300 ml of water and the pH was adjusted to 1 with 6N hydrochloric acid. Thereafter, the organic layer formed was separated, washed successively with a saturated aqueous sodium hydrogencarbonate solution, water and a saturated saline solution and then dried over anhydrous magnesium sulfate. The solvent was then removed by distillation under reduced pressure. The residue thus obtained was purified by a column chromatography (eluent: n-hexane:ethyl acetate= 10:1), to obtain 8.95 g of colorless, crystalline ethyl 4-bromo-2,5-di-fluoro-3-methylbenzoylacetate.

IR (KBr) cm$^{-1}$: $\nu_{C=O}$ 1644

NMR (CDCl$_3$) δ value: 1.00–1.70 (3H, m), 2.41 (3H, d, J=2.9 Hz), 3.70–4.70 (3.2H, m), 5.84 (0.4H, s), 7.30–7.75 (1H, m), 12.5 (0.4H, brs)

In the same manner, the following compounds were obtained.

Ethyl 4-bromo-2,5-difluoro-3-difluoromethoxybenzoylacetate

IR (KBr) cm$^{-1}$: $\nu_{C=O}$ 1670

NMR (CDCl$_3$) δ value: 0.70–1.40 (3H, m), 3.60–4.50 (3.2H, m), 5.85 (0.4H, s), 6.62 (1H, t, J=73 Hz), 7.30–7.70 (1H, m), 12.7 (0.4H, s)

Ethyl 4-bromo-2,5-difluoro-3-fluoromethoxybenzoylacetate

IR (KBr) cm$^{-1}$: $\nu_{C=O}$ 1654

NMR (CDCl$_3$) δ value: 1.00–1.50 (3H, m), 3.60–4.50 (3.2H, m), 5.69 (2H, d, J=53 Hz), 5.83 (0.4H, s), 7.20–7.70 (1H, m), 12.6 (0.4H, s)

Reference Example 7

In 18 ml of methylene chloride was suspended 1.80 g of 4-bromo-2,5-difluoro-3-hydroxymethylbenzoic acid and to the suspension were added 1.64 g of triethylamine and 0.84 g of acetic anhydride with ice-cooling, after which the suspension was stirred for one hour. The temperature of the suspension was then elevated to room temperature, at which the mixture was stirred for a further 12 hours. The reaction mixture was added to a mixed solvent of 20 ml of methylene chloride and 50 ml of water and the pH was adjusted to 1 with 6N hydrochloric acid. Thereafter, the organic layer formed was separated, washed with a saturated saline solution and then dried over anhydrous magnesium sulfate. The solvent was removed by distillation under reduced pressure. The residue obtained was purified by a column chromatography (eluent: chloroform:ethanol=9:1), to obtain a colorless, oily 3-acetoxymethyl-4-bromo-2,5-difluorobenzoic acid. The oily product obtained was dissolved in 42 ml of anhydrous tetrahydrofuran, and 1.64 g of N,N'-carbonyldiimidazole was added to the solution with ice-cooling. The resulting mixture was stirred at room temperature for one hour. Subsequently, 1.45 g of magnesium ethoxycarbonylacetate was added thereto and the resulting mixture was stirred at the same temperature for 20 hours. The reaction mixture was added to a mixed solvent of 80 ml of ethyl acetate and 100 ml of water, and the pH was adjusted to 1 with 6N hydrochloric acid. Thereafter, the organic layer formed was separated, washed with a saturated saline solution and then dried over anhydrous magnesium sulfate. Thereafter, the solvent was removed by distillation under reduced pressure. The residue thus obtained was purified by a column chromatography (eluent: n-hexane:ethyl acetate=20:1), to obtain 1.32 g of colorless, crystalline ethyl 3-acetoxymethyl-4-bromo-2,5-difluorobenzoylacetate.

IR (KBr) cm$^{-1}$: $\nu_{C=O}$ 1742, 1654

NMR (CDCl$_3$) δ value: 1.00–1.50 (3H, m), 2.08 (3H, s), 3.80–4.50 (3.2H, m), 5.32 (2H, d, J=2.4 Hz), 5.87 (0.4H, s), 7.40–7.90 (1H, m), 12.3 (0.4H, brs)

Reference Example 8

To 1.0 g of 4-bromo-2,5-difluoro-3-methoxy-6-nitrobenzoic acid was added 3 ml of thionyl chloride and 0.3 ml of N,N-dimethylformamide, and the resulting mixture was heated under reflux for one hour. The reaction mixture was concentrated under reduce pressure to obtain an acid chloride. Separately, 0.4 g of 60% sodium hydride was suspended in 30 ml of tetrahydrofuran, and 1.8 g of tert-butyl ethyl malonate was dropwise added to the suspension with ice-cooling, after which the suspension was stirred at the same temperature for two hours. To the reaction mixture obtained was dropwise added a solution of the above-obtained acid chloride in 10 ml of tetrahydrofuran at −20° C., and the resulting mixture was stirred with ice-cooling for 30 minutes and then at room temperature for one hour. The reaction mixture was added to a mixed solvent of 50 ml of ethyl acetate and 50 ml of water, and the pH was adjusted to 1 with 6N hydrochloric acid. The organic layer formed was separated, washed successively with water and a saturated saline solution, and then dried over anhydrous magnesium sulfate. The solvent was then removed by distillation under reduced pressure. To the residue thus obtained were added 10 ml of methylene chloride and 10 ml of trifluoroacetic acid, and the resulting mixture was stirred at room temperature for two hours. The reaction mixture was concentrated under reduced pressure, and the residue obtained was purified by a column chromatography (eluent: toluene), to obtain 0.9 g of colorless, crystalline ethyl 4-bromo-2,5-difluoro-3-methoxy-6-nitrobenzoylacetate.

IR (KBr) cm$^{-1}$: $\nu_{C=O}$ 1737, 1718

NMR (CDCl$_3$) δ value: 1.25 (3H, t, J=7.3 Hz), 3.60–4.40 (7H, m)

Reference Example 9

(1) In 150 ml of methylene chloride was dissolved 30.0 g of ethyl 4-bromo-2,5-difluoro-3-methylbenzoylacetate, and 19.1 g of acetic anhydride and 22.3 g of N,N-dimethylformamide dimethyl acetal were added to the solution, after which the resulting mixture was stirred at room temperature for one hour. Thereafter, the solvent was removed by distillation under reduced pressure. The residue obtained was dissolved in 90 ml of ethanol and 5.90 g of cyclopropylamine was added thereto, after which the resulting mixture was stirred at room temperature for 30 minutes. The solvent was then removed by distillation under reduced pressure. To the residue obtained was added n-hexane and the crystals formed were collected by filtration, to obtain 35.7 g of colorless, crystalline ethyl 2-(4-bromo-2,5-difluoro-3-methylbenzoyl)-3-cyclopropylaminoacrylate.

(2) In 175 ml of dimethyl sulfoxide was dissolved 35.0 g of ethyl 2-(4-bromo-2,5-difluoro-3-methylbenzoyl)-3-cyclopropylaminoacrylate, and 27.4 g of potassium carbonate was added to the solution, after which the resulting mixture was stirred at 100° C. for 30 minutes. The reaction mixture was cooled to room temperature, and 1,000 ml of water was then added thereto, after which the crystals formed were collected by filtration, to obtain 30.0 g of colorless, crystalline ethyl 7-bromo-1-cyclopropyl-6-fluoro-8-methyl-1,4-dihydro-4-oxoquinoline-3-carboxylate.

IR (KBr) cm$^{-1}$: $\nu_{C=O}$ 1731

NMR (CDCl$_3$) δ value: 0.70–1.70 (7H, m), 2.91 (3H, s), 3.70–4.10 (1H, m), 4.38 (2H, q, J=7.3 Hz), 8.01 (1H, d, J=8.3 Hz), 8.65 (1H, s)

In the same manner, the following compounds were obtained.

Ethyl 7-bromo-1-cyclopropyl-8-difluoromethoxy-6-fluoro-1,4-dihydro-4-oxoquinoline-3-carboxylate IR (KBr) cm$^{-1}$: $v_{C=O}$ 1723

NMR (CDCl$_3$) δ value: 0.90–1.60 (7H, m), 3.80–4.15 (1H, m), 4.39 (2H, q, J=7.3 Hz), 6.59 (1H, t, J=74 Hz), 8.16 (1H, d, J=8.3 Hz), 8.61 (1H, s)

Ethyl 7-bromo-1-cyclopropyl-6-fluoro-8-fluoromethoxy-1,4-dihydro-4-oxoquinoline-3-carboxylate IR (KBr) cm$^{-1}$: $v_{C=O}$ 1684, 1644

NMR (CDCl$_3$) δ value: 0.90–1.60 (7H, m), 3.80–4.60 (3H, m), 5.69 (2H, d, J=54 Hz), 8.11 (1H, d, J=8.3 Hz), 8.61 (1H, s)

Ethyl 8-acetoxymethyl-7-bromo-1-cyclopropyl-6-fluoro-1,4-dihydro-4-oxoquinoline-3-carboxylate IR (KBr) cm$^{-1}$: $v_{C=O}$ 1745, 1728, 1692

NMR (CDCl$_3$) δ value: 0.70–1.55 (7H, m), 2.07 (3H, s), 3.70–4.60 (3H, m), 5.88 (2H, s), 8.18 (1H, d, J=7.8 Hz), 8.64 (1H, s)

Reference Example 10

In 58 ml of ethanol was suspended 1.46 g of ethyl 8-acetoxymethyl-7-bromo-1-cyclopropyl-6-fluoro-1,4-dihydro-4-oxoquinoline-3-carboxylate, and 19 mg of sodium methoxide was added to the suspension, after which the resulting mixture was stirred at room temperature for seven hours. To the reaction mixture was added 60 ml of water and the pH was adjusted to 7 with 1N hydrochloric acid, after which the crystals formed were collected by filtration, to obtain 1.28 g of colorless, crystalline ethyl 7-bromo-1-cyclopropyl-6-fluoro-8-hydroxymethyl-1,4-dihydro-4-oxoquinoline-3-carboxylate.

IR (KBr) cm$^{-1}$: $v_{C=O}$ 1718

NMR (d$_1$-TFA) δ value: 1.05–1.90 (7H, m), 4.45–5.30 (3H, m), 5.99 (2H, s), 8.38 (1H, d, J=6.8 Hz), 9.52 (1H, s)

Reference Example 11

In 127 ml of methylene chloride was suspended 1.27 g of ethyl 7-bromo-1-cyclopropyl-6-fluoro-8-hydroxymethyl-1,4-dihydro-4-oxoquinoline-3-carboxylate, and 1.33 g of diethylaminosulfur trifluoride was dropwise added to the suspension at –40° C., after which the resulting mixture was stirred at –20° C. for one hour and then at 0° C. for three hours. The reaction mixture was added to 120 ml of ice water and the pH was adjusted to 8 with a saturated aqueous sodium hydrogencarbonate solution. Thereafter, the organic layer formed was separated, washed with a saturated saline solution and then dried over anhydrous magnesium sulfate. The solvent was then removed by distillation under reduced pressure. The residue thus obtained was purified by a column chromatography (eluent: chloroform:ethanol= 100:1), to obtain 1.05 g of colorless, crystalline ethyl 7-bromo-1-cyclopropyl-6-fluoro-8-fluoromethyl-1,4-dihydro-4-oxoquinoline-3-carboxylate.

IR (KBr) cm$^{-1}$: $v_{C=O}$ 1723, 1694

NMR (CDCl$_3$) δ value: 0.60–1.75 (7H, m), 3.65–4.65 (3H, m), 6.11 (2H, d, J=47 Hz), 8.21 (1H, dd, J=2.2 Hz, J=8.1 Hz), 8.64 (1H, s)

Reference Example 12

In 50 ml of toluene was suspended 5.00 g of ethyl 7-bromo-1-cyclopropyl-6-fluoro-8-methyl-1,4-dihydro-4-oxoquinoline-3-carboxylate, and 15.8 g of bis(tributyltin) and 95 mg of bis(triphenylphosphine)palladium (II) chloride were added to the suspension, after which the resulting mixture was heated under reflux for 24 hours. The reaction mixture was concentrated under reduced pressure, and the residue thus obtained was purified by a column chromatography (eluent: toluene:ethyl acetate=10:1), to obtain 5.10 g of colorless, crystalline ethyl 1-cyclopropyl-6-fluoro-8-methyl-7-tributylstannyl-1,4-dihydro-4-oxoquinoline-3-carboxylate IR (KBr) cm$^{-1}$: $v_{C=O}$ 1724

NMR (CDCl$_3$) δ value: 0.30–2.30 (34H, m), 2.79 (3H, s), 3.60–4.10 (1H, m), 4.38 (2H, q, J=6.8 Hz), 7.83 (1H, d, J=6.3 Hz), 8.63 (1H, s)

In the same manner, the following compounds were obtained.

Ethyl 1-cyclopropyl-6-fluoro-7-tributylstannyl-1,4-dihydro-4-oxoquinoline-3-carboxylate IR (KBr) cm$^{-1}$: $v_{C=O}$ 1725

NMR (CDCl$_3$) δ value: 0.50–1.80 (34H, m), 3.10–3.70 (1H, m), 4.40 (2H, q, J=6.8 Hz), 7.96 (1H, d, J=2.0 Hz), 8.03 (1H, d, J=6.3 Hz), 8.56 (1H, s)

Ethyl (S)-9-fluoro-3-methyl-7-oxo-10-tributylstannyl-2,3-dihydro-7H-pyrido[1,2,3-de][1,4]benzoxazine-6-carboxylate IR (KBr) cm$^{-1}$: $v_{C=O}$ 1718

NMR (CDCl$_3$) δ value: 0.30–2.30 (33H, m), 4.00–4.60 (5H, m), 7.60 (1H, d, J=6.8 Hz), 8.30 (1H, s)

Ethyl 1-cyclopropyl-6-fluoro-7-tributylstannyl-1,4-dihydro-4-oxo-1,8-naphthyridine-3-carboxylate IR (KBr) cm$^{-1}$: $v_{C=O}$ 1729

NMR (CDCl$_3$) δ value: 0.60–1.90 (34H, m), 3.40–3.95 (1H, m), 4.40 (2H, q, J=6.8 Hz), 8.16 (1H, d, J=5.9 Hz), 8.66 (1H, s)

Ethyl 8-chloro-1-cyclopropyl-6-fluoro-7-tributylstannyl-1,4-dihydro-4-oxoquinoline-3-carboxylate NMR (CDCl$_3$) δ value: 0.60–1.90 (34H, m), 3.90–4.60 (3H, m), 7.93 (1H, d, J=6.3 Hz), 8.63 (1H, s)

Ethyl 1-cyclopropyl-6-fluoro-8-methoxy-7-tributylstannyl-1,4-dihydro-4-oxoquinoline-3-carboxylate IR (KBr) cm$^{-1}$: $v_{C=O}$ 1731

NMR (CDCl$_3$) δ value: 0.40–2.0 (34H, m), 3.50–4.05 (4H, m), 4.27 (2H, q, J=7.0 Hz), 7.84 (1H, d, J=6.4 Hz), 8.57 (1H, s)

Reference Example 13

(1) In 380 ml of diethyl ether was dissolved 19.0 g of 1-bromo-3,4-di(hydroxymethyl)benzene, and 112 g of phosphorus tribromide was added to this solution with ice-cooling, after the resulting mixture was allowed to stand for three days. The reaction mixture was added to 1000 ml of ice water and the pH was adjusted to 7 with sodium hydrogencarbonate, after which the mixture was extracted with 1000 ml of ethyl acetate. The organic layer obtained was washed with a saturated saline solution and then dried over anhydrous magnesium sulfate. The solvent was then removed by distillation under reduced pressure, to obtain 28.5 g of colorless, crystalline 1-bromo-3,4-di (bromomethyl)benzene.

(2) In 70 ml of N,N-dimethylformamide was suspended 3.97 g of sodium hydride (purity: 60%), and 50 ml of an N,N-dimethylformamide solution containing 8.49 g of p-toluenesulfonamide was added thereto, after which the resulting mixture was stirred at 60° C. for 30 minutes. To the reaction mixture was added a solution of 17.0 g of 1-bromo-3,4-di(bromomethyl)benzene in 50 ml of N,N-dimethylformamide at 60° C., and the resulting mixture was stirred at 60° C. for one hour. The reaction mixture obtained was added to 500 ml of ice water and the precipitate was collected by filtration, and purified by a column chromatography (eluent: chloroform), to obtain 15.2 g of colorless, crystalline 5-bromo-2-(p-toluenesulfonyl)isoindoline.

IR (KBr) cm$^{-1}$: $\nu_{SO_2}$ 1347, 1164

NMR (CDCl$_3$) δ value: 2.39 (3H, s), 4.56 (4H, brs), 6.75–7.90 (7H, m)

In the same manner, the following compounds were obtained.

5-Bromo-1-methyl-2-(p-toluenesulfonyl)isoindoline

IR (neat) cm$^{-1}$: $\nu_{SO_2}$ 1347, 1164

NMR (CDCl$_3$) δ value: 1.60, 1.66 (3H, each, d, J=6.0 Hz), 2.34, 2.39 (3H, each, s), 4.50–5.15 (3H, m), 6.70–7.95 (7H, m)

5-Bromo-3-methyl-2-(p-toluenesulfonyl)isoindoline

IR (neat) cm$^{-1}$: $\nu_{SO_2}$ 1346, 1165

NMR (CDCl$_3$) δ value: 1.62 (3H, d, J=6.3 Hz), 2.38 (3H, s), 4.35–5.15 (3H, m), 6.65–7.90 (7H, m)

5-Bromo-4,7-difluoro-2-(p-toluenesulfonyl)isoindole

IR (KBr) cm$^{-1}$: $\nu_{SO_2}$ 1348, 1163

NMR (CDCl$_3$) δ value: 2.42 (3H, s), 4.66 (4H, s), 6.88 (1H, t, J=6.0 Hz), 7.33 (2H, d, J=8.0 Hz), 7.78 (2H, d, J=8.0 Hz)

Reference Example 14

(1) To a mixture of 850 mg of 1-(1-aminocyclopropyl)-4-bromo-2-hydroxymethylbenzene and 8.5 ml of methanol was added 1.24 g of ethyl trifluoroacetate, and the resulting mixture was stirred at room temperature for 24 hours. The solvent was removed by distillation under reduced pressure, and the residue obtained was purified by a column chromatography (eluent: chloroform:ethanol=30:1), to obtain 1.02 g of colorless, crystalline 4-bromo-2-hydroxymethyl-1-(1-trifluoroacetylaminocyclopropyl)benzene.

IR (KBr) cm$^{-1}$: $\nu_{C=O}$ 1717, 1702

NMR (CDCl$_3$) δ value: 1.05–1.60 (4H, m), 2.50 (1H, brs), 4.95 (2H, s), 7.15–7.70 (3H, m), 8.06 (1H, brs)

(2) In 20 ml of benzene was suspended 950 mg of 4-bromo-2-hydroxymethyl-1-(1-triflfuoroacetylaminocyclopropyl)benzene obtained (1), and 680 mg of tri-n-butylphosphine and 850 mg of 1,1'-azodicarbonyl-di(piperidine) were added in this order to the suspension with ice-cooling, after which the temperature of the resulting mixture was elevated to room temperature, at which the mixture was stirred for three hours. Insolubles were removed by filtration, and the solvent was then removed by distillation under reduced pressure. The residue obtained was purified by a column chromatography (eluent: n-hexane:ethyl acetate=15:1), to obtain 720 mg of colorless, crystalline 5-bromo-2-trifluoroacetyl-spiro[isoindoline-1,1'-cyclopropane].

IR (KBr) cm$^{-1}$: $\nu_{C=O}$ 1697

NMR (CDCl$_3$) δ value: 0.75–1.20 (2H, m), 2.30–2.75 (2H, m), 5.08 (2H, s), 6.56 (1H, d, J=9.0 Hz), 7.15–7.65 (2H, m)

Reference Example 15

In 25 ml of 47% hydrobromic acid was suspended 5.0 g of 2-(p-toluenesulfonyl)-5-bromoisoindoline, and 4.0 g of phenol and 15 ml of propionic acid were added to the suspension, after which the resulting mixture was heated under reflux for four hours. The reaction mixture was concentrated under reduced pressure, and ethanol was added to the residue obtained, after which the resulting crystals were collected by filtration, to obtain 3.5 g of 5-bromoisoindoline hydrobromide. The hydrobromide obtained was suspended in 50 ml of methylene chloride, and 2.8 g of triethylamine was added to the suspension, after which 2.4 g of carbobenzoxy chloride was dropwise added thereto with ice-cooling. Thereafter, the resulting mixture was stirred at room temperature for one hour. The reaction mixture was added 50 ml of water and the pH was adjusted to 1 with 6N hydrochloric acid. Thereafter, the organic layer formed was separated, washed with a saturated saline solution and then dried over anhydrous magnesium chloride. The solvent was then removed by distillation under reduced pressure. To the residue thus obtained was added n-hexane, and the resulting crystals were collected by filtration to obtain 3.8 g of colorless, crystalline 2-benzyloxycarbonyl-5-bromoisoindoline.

IR (KBr) cm$^{-1}$: $\nu_{C=O}$ 1705

NMR (CDCl$_3$) δ value: 4.69 (4H, s), 5.20 (2H, s), 6.70–7.40 (8H, m)

Reference Example 16

In 24 ml of toluene was suspended 1.20 g of 2-(p-toluenesulfonyl)-5-bromoisoindoline, and 3.95 g of hexabutyldistannane and 39.4 mg of tetrakis(triphenylphosphine) palladium (0) were added to the suspension, after which the resulting mixture was heated under reflux for 24 hours under a nitrogen atmosphere. The reaction mixture was concentrated under reduced pressure, and the residue obtained was purified by a column chromatography (eluent: hexane:ethyl acetate=10:1), to obtain 0.92 g of oily 2-(p-toluenesulfonyl)-5-tributylstannylisoindoline.

IR (neat) cm$^{-1}$: $\nu_{SO_2}$ 1349, 1166

NMR (CDCl$_3$) δ value: 0.20–2.00 (27H, m), 2.40 (3H, s), 4.61 (4H, brs), 6.50–8.00 (7H, m)

In the same manner, the following compounds were obtained.

1-Methyl-2-(p-toluenesulfonyl)-5-tributylstannylisoindoline

IR (neat) cm$^{-1}$: $v_{SO_2}$ 1349, 1165

NMR (CDCl$_3$) δ value: 0.70–1.80 (30H, m), 2.38 (3H, s), 4.55–5.15 (3H, m), 6.90–7.90 (7H, m)

3-Methyl-2-(p-toluenesulfonyl)-5-tributylstannylisoindoline

IR (neat) cm$^{-1}$: $v_{SO_2}$ 1349, 1165

NMR (CDCl$_3$) δ value: 0.60–1.90 (30H, m), 2.37 (3H, s), 4.30–5.20 (3H, m), 6.80–7.90 (7H, m)

5-Tributylstannyl-2-trifluoroacetyl-spiro[isoindoline-1,1'-cyclopropane]

IR (neat) cm$^{-1}$: $v_{C=O}$ 1694

NMR (CDCl$_3$) δ value: 0.70–2.10 (29H, m), 2.35–2.75 (2H, m), 5.16 (2H, s), 6.60–7.70 (3H, m)

2-Benzyloxycarbonyl-5-tributylstannylisoindoline

IR (neat) cm$^{-1}$: $v_{C=O}$ 1718, 1709

NMR (CDCl$_3$) δ value: 0.30–1.70 (27H, m), 4.73 (4H, s), 5.15 (2H, s), 6.80–7.40 (8H, m)

Reference Example 17

In 27 ml of toluene was dissolved 3.55 g of 2-(p-toluenensulfonyl)-5-tributylstannylisoindoline, and 1.35 g of ethyl 4-bromo-2,5-difluoro-3-methylbenzoylacetate and 0.29 g of bis(triphenylphosphine)palladium (II) chloride were added to the solution, after which the resulting mixture was heated under reflux for eight hours under a nitrogen atmosphere. The reaction mixture was concentrated under reduced pressure, the residue obtained was purified by a column chromatography (eluent: benzene:ethyl acetate=70:1), to obtain 1.25 g of colorless, crystalline ethyl 2,5-difluoro-3-methyl- 4-[2-(p-toluenesulfonyl)isoindolin-5-yl]benzoylacetate.

IR (KBr) cm$^{-1}$: $v_{C=O}$ 1746

NMR (CDCl$_3$) δ value: 1.10–1.70 (3H, m), 2.07 (3H, d, J=2.9 Hz), 2.41 (3H, s, m), 3.80–4.50 (3.4H, m), 4.67 (4H, s), 5.88 (0.3H, s), 6.80–8.00 (8H, m), 12.6 (0.3H, brs)

In the same manner, the following compounds were obtained.

Ethyl 2,5-difluoro-4-[2-(p-toluenesulfonyl)isoindolin-5-yl]benzoylacetate

IR (KBr) cm$^{-1}$: $v_{C=O}$ 1747

NMR (CDCl$_3$) δ value: 1.10–1.70 (3H, m), 2.40 (3H, s), 3.90–4.50 (3.2H, m), 4.66 (4H, s), 5.89 (0.4H, s), 7.00–8.00 (9H, m), 12.7 (0.4H, brs)

Ethyl 4-[2-(benzyloxycarbonyl)isoindolin-5-yl]-2,5-difluoro-3-methoxy-6-nitrobenzoylacetate IR (KBr) cm$^{-1}$: $v_{C=O}$ 1751, 1707

NMR (CDCl$_3$) δ value: 1.00–1.60 (3H, m), 3.60–4.50 (6.2H, m), 4.81 (4H, s), 5.22 (2H, s), 5.50 (0.4H, s), 7.10–7.40 (8H, m), 12.2 (0.4H, brs)

Reference Example 18

In 21 ml of xylene were suspended 700 mg of ethyl 7-bromo-1-cyclopropyl-6-fluoro-8-methoxy-1,4-dihydro-4-oxoquinoline-3-carboxylate, 889 mg of 1-cyano- 2-methyl-4-tributylstannylbenzene and 130 mg of bis(triphenylphosphine)palladium (II) chloride, and the resulting suspension was heated under reflux for two hours. The reaction mixture was cooled to room temperature, and the crystals precipitated were then collected by filtration. The crude crystals obtained were purified by a column chromatography (eluent: chloroform), to obtain 490 mg of colorless, crystalline ethyl 7-(4-cyano-3-methyl)phenyl-1-cyclopropyl-6-fluoro-8-methoxy-1,4-dihydro-4-oxoquinoline-3-carboxylate.

IR (KBr) cm$^{-1}$: $v_{C=O}$ 1726

NMR (CDCl$_3$) δ value: 0.90–1.70 (7H, m), 2.64 (3H, s), 3.37 (3H, s), 3.65–4.15 (1H, m), 4.40 (2H, q, J=7.0 Hz), 7.20–7.90 (3H, m), 8.03 (1H, d, J=9.5 Hz), 8.64 (1H, s)

EXAMPLE 1

In 25 ml of N,N-dimethylformamide was dissolved 2.30 g of 2-(p-toluenesulfonyl)-5-bromoisoindoline, and 1.51 g of silver (I) oxide and 0.75 g of tetrakis(triphenylphosphine) palladium (0) were added to the solution, after which the resulting mixture was stirred at 100° C. for five minutes under a nitrogen atmosphere. Subsequently, to this reaction mixture was added 1.54 g of ethyl 1-cyclopropyl-6-fluoro-8-methyl-7-tributylstannyl-1,4-dihydro-4-oxoquinoline-3-carboxylate dissolved in 5 ml of N,N-dimethylformamide, and resulting mixture was stirred at 100° C. for 15 minutes. The reaction mixture was added to a mixed solvent of 50 ml of ethyl acetate and 100 ml of water, and the pH was adjusted to 2 with 2N hydrochloric acid, after which insolubles were removed by filtration. The organic layer formed was separated, washed with a saturated saline solution and then dried over anhydrous magnesium sulfate. The solvent was then removed by distillation under reduced pressure. The residue obtained was purified by a column chromatography (eluent: toluene:ethyl acetate=3:1), and diethyl ether was thereafter added thereto, after which the crystals formed were collected by filtration, to obtain 0.55 g of colorless, crystalline ethyl 1-cyclopropyl-6-fluoro-8-methyl-7-[2-(p-toluenesulfonyl)isoindolin-5-yl]-1,4-dihydro-4-oxoquinoline-3-carboxylate.

IR (KBr) cm$^{-1}$: $v_{C=O}$ 1733, 1693

NMR (CDCl$_3$) δ value: 0.70–1.60 (7H, m,), 2.42 (3H, s), 2.50 (3H, s), 3.70–4.10 (1H, m), 4.40 (2H, q, J=7.3 Hz), 4.69 (4H, s), 6.90–8.20 (8H, m), 8.70 (1H, s)

In the same manner, the following compounds were obtained.

Ethyl 1-cyclopropyl-6-fluoro-7-[2-(p-toluenesulfonyl)isoindolin-5-yl]-1,4-dihydro-4-oxoquinoline-3-carboxylate IR (KBr) cm$^{-1}$: $v_{C=O}$ 1728, 1693

NMR (CDCl$_3$) δ value: 0.90–1.55 (7H, m), 2.41 (3H, s), 3.20–3.70 (1H, m), 4.40 (2H, q, J=6.8 Hz), 4.69 (4H, s), 7.00–8.25 (9H, m), 8.57 (1H, s)

Ethyl (S)-9-fluoro-3-methyl-7-oxo-10-[2-(p-toluenesulfonyl)isoindolin-5-yl]-2,3-dihydro-7H-pyrido[1,2,3-de]-[1,4]benzoxazine-6-carboxylate IR (KBr) cm$^{-1}$: $v_{C=O}$ 1721

NMR (CDCl$_3$) δ value: 1.00–1.55 (6H, m), 2.41 (3H, s), 4.00–4.80 (9H, m), 6.90–7.90 (8H, m), 8.32 (1H, s)

Ethyl 1-cyclopropyl-6-fluoro-7-[2-(p-toluenesulfonyl)-isoindolin-5-yl]-1,4-dihydro-4-oxo-1,8-naphthyridine-3-carboxylate IR (KBr) cm$^{-1}$: $v_{C=O}$ 1719, 1679, 1651

NMR (d$_1$-TFA) δ value: 1.10–1.90 (7H, m), 2.47 (3H, s), 4.10–5.10 (7H, m), 7.20–8.80 (8H, m), 9.45 (1H, s)

Ethyl 8-chloro-1-cyclopropyl-6-fluoro-7-[2-(p-toluenesulfonyl)isoindolin-5-yl]-1,4-dihydro-4-oxoquinoline-3-carboxylate IR (KBr) cm$^{-1}$: $v_{C=O}$ 1726

NMR (CDCl$_3$) δ value: 0.70–1.70 (7H, m), 2.41 (3H, s), 3.80–4.80 (7H, m), 6.90–8.25 (8H, m), 8.69 (1H, s)

Ethyl 1-cyclopropyl-7-[4,7-difluoro-2-(p-toluenesulfonyl)isoindolin-5-yl]-6-fluoro-1,4-dihydro-4-oxoquinoline-3-carboxylate IR (KBr) cm$^{-1}$: $v_{C=O}$ 1728, 1690

NMR (CDCl$_3$) δ value: 1.00–1.60 (7H, m), 2.42 (3H, s), 3.15–3.65 (1H, m), 4.39 (2H, q, J=6.8 Hz), 4.74 (4H, s), 6.90–8.00 (6H, m), 8.20 (1H, d, J=10.0 Hz), 8.57 (1H, s)

Ethyl 1-cyclopropyl-7-[4,7-difluoro-2-(p-toluenesulfonyl)isoindolin-5-yl]-6-fluoro-8-methoxy-1,4-dihydro-4-oxoquinoline-3-carboxylate IR (KBr) cm$^{-1}$: $v_{C=O}$ 1729, 1691

NMR (CDCl$_3$) δ value: 0.90–1.70 (7H, m), 2.44 (3H, s), 3.43 (3H, s), 3.70–4.95 (7H, m), 6.80–8.15 (6H, m), 8.57 (1H, s)

EXAMPLE 2

In 1 ml of toluene was suspended 47 mg of ethyl 7-bromo-1-cyclopropyl-6-fluoro-8-methyl-1,4-dihydro-4-oxoquinoline-3-carboxylate, and to this suspension were added 74 mg of 2-(p-toluenesulfonyl)-5-tributylstannylisoindoline and 1.5 mg of tetrakis(triphenylphosphine)palladium (0), after which the resulting mixture was heated under reflux for 18 hours under a nitrogen atmosphere. The reaction mixture was concentrated under reduced pressure, and the residue obtained was purified by a column chromatography (eluent: n-hexane:ethyl acetate=1:1), and diethyl ether was then added thereto, after which the crystals formed were collected by filtration, to obtain 27 mg of colorless, crystalline ethyl 1-cyclopropyl-6-fluoro-8-methyl-7-[2-(p-toluenesulfonyl)isoindolin-5-yl]-1,4-dihydro-4-oxoquinoline-3-carboxylate.

The physical properties of this compound were identical with those of the compound obtained in Example 1.

In the same manner, the following compounds were obtained.

Ethyl 1-cyclopropyl-6,8-difluoro-7-[2-(p-toluenesulfonyl)isoindolin-5-yl]-1,4-dihydro-4-oxoquinoline-3-carboxylate IR (KBr) cm$^{-1}$: $v_{C=O}$ 1731, 1696

NMR (CDCl$_3$) δ value: 0.90–1.80 (7H, m), 2.41 (3H, s), 3.60–4.10 (1H, m), 4.10–4.90 (6H, m), 6.80–8.30 (8H, m), 8.59 (1H, s)

Ethyl 1-(2,4-difluorophenyl)-6-fluoro-7-[2-(p-toluenesulfonyl)isoindolin-5-yl]-1,4-dihydro-4-oxo-1,8-naphthyridine-3-carboxylate IR (KBr) cm$^{-1}$: $v_{C=O}$ 1675, 1655

NMR (CDCl$_3$) δ value: 1.40 (3H, t, J=6.8 Hz), 2.39 (3H, s), 4.41 (2H, q, J=6.8 Hz), 4.63 (4H, s), 6.80–7.90 (10H, m), 8.48 (1H, d, J=10.0 Hz), 8.58 (1H, s)

Ethyl 7-[2-(benzyloxycarbonyl)isoindolin-5-yl]-1-cyclopropyl-6-fluoro-8-fluoromethyl-1,4-dihydro-4-oxoquinoline-3-carboxylate IR (KBr) cm$^{-1}$: $v_{C=O}$ 1732, 1718

NMR (CDCl$_3$) δ value: 0.85–1.75 (7H, m), 3.85–4.65 (3H, m), 4.81 (4H, s), 5.21 (2H, s), 5.61 (2H, d, J=48 Hz), 7.05–7.55 (8H, m), 8.23 (1H, dd, J=2.0 Hz, 8.8 Hz), 8.66 (1H, s)

EXAMPLE 3

In 5 ml of toluene was suspended 0.25 g of ethyl 7-bromo-1-cyclopropyl-6-fluoro-8-methoxy-1,4-dihydro-4-oxoquinoline-3-carboxylate, and to this suspension were added 0.55 g of 2-(p-toluenesulfonyl)-5-tributylstannylisoindoline and 0.09 g of bis(triphenylphosphine)palladium (II) chloride, after which the resulting mixture was heated under reflux for eight hours under an argon stream. The reaction mixture was concentrated under reduced pressure, and the residue obtained was purified by a column chromatography (eluent: chloroform), after which diethyl ether was added thereto. The crystals formed were collected by filtration to obtain 0.19 g of colorless, crystalline ethyl 1-cyclopropyl-6-fluoro-8-methoxy-7-[2-(p-toluenesulfonyl)isoindolin-5-yl]-1,4-dihydro-4-oxoquinoline-3-carboxylate.

IR (KBr) cm$^{-1}$: $v_{C=O}$ 1731

NMR (CDCl$_3$) δ value: 0.80–1.70 (7H, m), 2.41 (3H, s), 3.32 (3H, s), 3.60–4.20 (1H, m), 4.40 (2H, q, J=6.8 Hz), 4.68 (4H, s), 7.10–7.50 (5H, m), 7.60–8.15 (3H, m), 8.61 (1H, s)

In the same manner, the following compounds were obtained.

Ethyl 1-cyclopropyl-6-fluoro-8-methoxy-7-[1-methyl-2-(p-toluenesulfonyl)isoindolin-5-yl]-1,4-dihydro-4-oxoquinoline-3-carboxylate IR (KBr) cm$^{-1}$: $v_{C=O}$ 1732

NMR (CDCl$_3$) δ value: 0.80–2.00 (10H, m), 2.40 (3H, s), 3.30 (3H, s), 3.75–5.30 (6H, m), 7.10–8.15 (8H, m), 8.65 (1H, s)

Ethyl 1-cyclopropyl-6-fluoro-8-methoxy-7-[3-methyl-2-(p-toluenesulfonyl)isoindolin-5-yl]-1,4-dihydro-4-oxoquinoline-3-carboxylate IR (KBr) cm$^{-1}$: $v_{C=O}$ 1729

NMR (CDCl$_3$) δ value: 0.90–1.80 (10H, m), 2.39 (3H, s), 3.31 (3H, s), 3.75–5.10 (6H, m), 7.05–8.10 (8H, m), 8.61 (1H, s)

Ethyl 1-cyclopropyl-6-fluoro-8-methoxy-7-[2-trifluoroacetyl-spiro[isoindolin-1,1'-cyclopropan]-5-yl]-1,4-dihydro-4-oxoquinoline-3-carboxylate IR (KBr) cm$^{-1}$: $v_{C=O}$ 1731, 1697

NMR (CDCl$_3$) δ value: 0.70–1.90 (9H, m), 2.20–2.90 (2H, m), 3.38 (3H, s), 3.60–4.70 (3H, m), 5.21 (2H, s), 6.55–8.20 (4H, m), 8.59 (1H, s)

Ethyl 1-cyclopropyl-8-difluoromethoxy-6-fluoro-7-[2-(p-toluenesulfonyl)isoindolin-5-yl]-1,4-dihydro-4-oxoquinoline-3-carboxylate IR (KBr) cm$^{-1}$: $v_{C=O}$ 1730

NMR (CDCl$_3$) δ value: 0.90–1.70 (7H, m), 2.40 (3H, s), 3.70–4.85 (7H, m), 5.83 (1H, t, J=75 Hz), 7.00–8.30 (8H, m), 8.62 (1H, s)

Ethyl 1-cyclopropyl-8-difluoromethoxy-6-fluoro-7-[3-methyl-2-(p-toluenesulfonyl)isoindolin-5-yl]-1,4-dihydro-4-oxoquinoline-3-carboxylate IR (KBr) cm$^{-1}$: ν$_{C=O}$ 1732

NMR (CDCl$_3$) δ value: 0.70–1.80 (10H, m), 2.39 (3H, s), 3.60–5.30 (6H, m), 5.80 (1H, t, J=75 Hz), 6.80–8.30 (8H, m), 8.64 (1H, s)

Ethyl 1-cyclopropyl-8-difluoromethoxy-6-fluoro-7-[2-trifluoroacetyl-spiro[isoindolin-1,1'-cyclopropan]-5-yl]-1,4-dihydro-4-oxoquinoline-3-carboxylate IR (KBr) cm$^{-1}$: ν$_{C=O}$ 1729, 1701

NMR (CDCl$_3$) δ value: 0.80–1.65 (9H, m), 2.40–2.80 (2H, m), 3.80–4.70 (3H, m), 5.20 (2H, s), 5.88 (1H, t, J=74 Hz), 6.70–7.60 (3H, m), 8.15 (1H, d, J=9.0 Hz), 8.61 (1H, s)

Ethyl 1-cyclopropyl-6-fluoro-8-fluoromethoxy-7-[2-(p-toluenesulfonyl)isoindolin-5-yl]-1,4-dihydro-4-oxoquinoline-3-carboxylate IR (KBr) cm$^{-1}$: ν$_{C=O}$ 1727

NMR (CDCl$_3$) δ value: 0.90–1.60 (7H, m), 2.41 (3H, s), 3.75–4.80 (7H, m), 5.02 (2H, d, J=54 Hz), 7.00–7.85 (7H, m), 8.10 (1H, d, J=9.3 Hz), 8.62 (1H, s)

Ethyl 1-cyclopropyl-6-fluoro-7-[1-methyl-2-(p-toluenesulfonyl)isoindolin-5-yl]-1,4-dihydro-4-oxoquinoline-3-carboxylate IR (KBr) cm$^{-1}$: ν$_{C=O}$ 1727

NMR (CDCl$_3$) δ value: 1.00–1.90 (10H, m), 2.38 (3H, s), 3.20–3.70 (1H, m), 3.90–5.20 (5H, m), 7.00–8.25 (9H, m), 8.54 (1H, s)

Ethyl 1-cyclopropyl-6-fluoro-7-[3-methyl-2-(p-toluenesulfonyl)isoindolin-5-yl]-1,4-dihydro-4-oxoquinoline-3-carboxylate IR (KBr) cm$^{-1}$: ν$_{C=O}$ 1727, 1708, 1695

NMR (CDCl$_3$) δ value: 0.80–1.90 (10H, m), 2.39 (3H, s), 3.10–3.70 (1H, m), 3.90–5.20 (5H, m), 6.80–8.25 (9H, m), 8.55 (1H, s)

Ethyl 7-[2-(benzyloxycarbonyl)isoindolin-5-yl]-8-chloro-6-fluoro-1-[(1R,2S)-2-fluorocyclopropyl]-1,4-dihydro-4-oxoquinoline-3-carboxylate IR (KBr) cm$^{-1}$: ν$_{C=O}$ 1726, 1709

NMR (CDCl$_3$) δ value: 0.80–1.70 (5H, m), 3.80–4.90 (7.5H, m), 5.00–5.50 (2.5H, m), 6.90–7.90 (8H, m), 8.18 (1H, d, J=8.8 Hz), 8.59 (1H, d, J=2.4 Hz)

EXAMPLE 4

In 2 ml of methylene chloride was dissolved 200 mg of ethyl 2,5-difluoro-3-methyl-4-[2-(p-toluenesulfonyl)isoindolin-5-yl]benzoylacetate, and to this solution were added 76 mg of acetic anhydride and 90 mg of N,N-dimethylformamide dimethyl acetal, after which the resulting mixture was stirred at room temperature for two hours. Thereafter, the solvent was removed by distillation under reduced pressure. The residue obtained was dissolved in 1 ml of ethanol, and a solution of 58 mg of 2-fluoroethylamine hydrochloride and 27 mg of sodium methoxide in 1 ml of ethanol was added to the solution, after which the resulting mixture was stirred at room temperature for 20 minutes. The reaction mixture was concentrated under reduced pressure, and the residue obtained was dissolved in 2 ml of N,N-dimethylformamide, after which 65 mg of potassium carbonate was added to the solution. The resulting mixture was stirred at 100° C. for one hour. The reaction mixture was cooled to room temperature, and thereafter, water was added to the mixture. The resulting precipitate was collected by filtration, and the pale yellow solid obtained was purified by a column chromatography (eluent: n-hexane:ethyl acetate= 2:1). And diisopropyl ether was thereafter added thereto, after which the crystals formed were collected by filtration, to obtain 126 mg of colorless, crystalline ethyl 6-fluoro-1-(2-fluoroethyl)-8-methyl-7-[2-(p-toluenesulfonyl)isoindolin-5-yl]-1,4-dihydro-4-oxoquinoline-3-carboxylate.

IR (KBr) cm$^{-1}$: ν$_{C=O}$ 1724, 1696

NMR (CDCl$_3$) δ value: 1.40 (3H, t, J=7.3 Hz), 2.28 (3H, s), 2.41 (3H, s), 4.00–5.10 (10H, m), 6.90–7.90 (7H, m), 8.10 (1H, d, J=9.3 Hz), 8.48 (1H, s)

In the same manner, the following compounds were obtained.

Ethyl 1-ethyl-6-fluoro-8-methyl-7-[2-(p-toluenesulfonyl)isoindolin-5-yl]-1,4-dihydro-4-oxoquinoline-3-carboxylate IR (KBr) cm$^{-1}$: ν$_{C=O}$ 1725, 1686

NMR (CDCl$_3$) δ value: 1.10–1.80 (6H, m), 2.30 (3H, s), 2.39 (3H, s), 4.10–4.90 (8H, m), 7.00–8.00 (7H, m), 8.10 (1H, d, J=9.3 Hz), 8.46 (1H, s)

Ethyl 6-fluoro-1-[(1R,2S)-2-fluorocyclopropyl]-8-methyl-7-[2-(p-toluenesulfonyl)isoindolin-5-yl]-1,4-dihydro-4-oxoquinoline-3-carboxylate IR (KBr) cm$^{-1}$: ν$_{C=O}$ 1725, 1690

NMR (CDCl$_3$) δ value: 1.00–1.90 (5H, m), 2.42 (6H, s), 3.30–4.80 (7.5H, m), 5.10–5.50 (0.5H, m), 6.80–8.20 (8H, m), 8.57 (1H, d, J=2.9 Hz)

Ethyl 1-(2,4-difluorophenyl)-6-fluoro-8-methyl-7-[2-(p-toluenesulfonyl)isoindolin-5-yl]-1,4-dihydro-4-oxoquinoline-3-carboxylate IR (KBr) cm$^{-1}$: ν$_{C=O}$ 1734, 1700

Ethyl 1-(4-benzyloxyphenyl)-6-fluoro-8-methyl-7-[2-(p-toluenesulfonyl)isoindolin-5-yl]-1,4-dihydro-4-oxoquinoline-3-carboxylate IR (KBr) cm$^{-1}$: ν$_{C=O}$ 1728, 1694

NMR (CDCl$_3$) δ value: 1.10–1.80 (6H, m), 2.36 (3H, s), 4.35 (2H, q, J=7.3 Hz), 4.60 (4H, s), 5.08 (2H, s), 6.80–7.90 (16H, m), 8.11 (1H, d, J=9.3 Hz), 8.43 (1H, s)

Ethyl 6-fluoro-1-(2-fluoroethyl)-7-[2-(p-toluenesulfonyl)isoindolin-5-yl]-1,4-dihydro-4-oxoquinoline-3-carboxylate IR (KBr) cm$^{-1}$: ν$_{C=O}$ 1724

NMR (CDCl$_3$) δ value: 1.40 (3H, t, J=7.3 Hz), 2.41 (3H, s), 4.10–5.35 (10H, m), 7.00–7.90 (8H, m), 8.20 (1H, d, J=10.3 Hz), 8.46 (1H, s)

Ethyl 1-(2,4-difluorophenyl)-6-fluoro-7-[2-(p-toluenesulfonyl)isoindolin-5-yl]-1,4-dihydro-4-oxoquinoline-3-carboxylate IR (KBr) cm$^{-1}$: $v_{C=O}$ 1725

NMR (CDCl$_3$) δ value: 1.40 (3H, t, J=7.3 Hz), 2.39 (3H, s), 4.10–4.70 (6H, m), 6.90–7.90 (11H, m), 8.23 (1H, d, J=10.3 Hz), 8.38 (1H, s)

EXAMPLE 5

In 0.71 g of ethyl orthoformate and 0.49 g of acetic anhydride was dissolved 0.66 g of ethyl 4-[2-(benzyloxycarbonyl)isoindolin-5-yl]-2,5-difluoro-3-methoxy-6-nitrobenzoylacetate, and the solution was heated under reflux for 30 minutes. The reaction mixture was concentrated under reduced pressure, and the residue obtained was dissolved in 3.3 ml of ethanol and 2 ml of methylene chloride. To the solution was added 0.08 g of cyclopropylamine, and the resulting mixture was stirred at room temperature for 30 minutes. The reaction mixture was concentrated under reduced pressure, and the residue obtained was dissolved in 10 ml of tetrahydrofuran. To the solution was added 0.05 g of 60% sodium hydride, and the resulting mixture was stirred at room temperature for 30 minutes. To the reaction mixture was added 10 ml of 1N hydrochloric acid, and the crystals precipitated were collected by filtration, to obtain 0.33 g of colorless, crystalline ethyl 7-[2-(benzyloxycarbonyl)isoindolin-5-yl]-1-cyclopropyl-6-fluoro-8-methoxy-5-nitro-1,4-dihydro-4-oxoquinoline-3-carboxylate.

IR (KBr) cm$^{-1}$: $v_{C=O}$ 1728, 1709

NMR (CDCl$_3$) δ value: 0.90–1.60 (7H, m), 3.42 (3H, s), 3.70–4.10 (1H, m), 4.34 (2H, q, J=6.8 Hz), 4.84 (4H, s), 5.23 (2H, s), 7.05–7.55 (8H, m), 8.61 (1H, s)

EXAMPLE 6

(1) In 20 ml of carbon tetrachloride were suspended 470 mg of ethyl 7-(4-cyano-3-methyl)phenyl-1-cyclopropyl-6-fluoro-8-methoxy-1,4-dihydro-4-oxoquinoline-3-carboxylate, 230 mg of N-bromosuccinimide and 50 mg of perbenzoic acid, and the suspension was heated under refulx for two hours. To the reaction mixture were added 110 mg of N-bromosuccinimide and 20 mg of perbenzoic acid and the resulting mixture was heated under reflux for a further two hours. This operation was repeated once. The solvent was removed by distillation under reduced pressure and to the residue obtained were added 20 ml of chloroform and 10 ml of water to allow the mixture to separate into two layers. The organic layer formed was separated and dried over anhydrous magnesium sulfate. Thereafter, the solvent was removed by distillation under reduced pressure, to obtain 370 mg of crude crystals of ethyl 7-(3-bromomethyl-4-cyano)phenyl-1-cyclopropyl-6-fluoro-8-methoxy-1,4-dihydro-4-oxoquinoline-3-carboxylate.

(2) The compound obtained in (1) above, 76 mg of sodium azide and 13 mg of tetra-n-butylammonium bromide were dissolved in a mixed solvent of 2 ml of water and 2 ml of methylene chloride, and the solution was stirred at room temperature for 15 hours. The solvent was removed by distillation under reduced pressure and to the residue obtained were added 20 ml of ethyl acetate and 10 ml of water to allow the mixture to separate into two layers. The organic layer formed was separated, washed successively with water and a saturated saline solution and then dried over anhydrous magnesium sulfate. The solvent was then removed by distillation under reduced pressure, and diethyl ether was added to the residue obtained. The crystals formed were collected by filtration, to obtain 270 mg of colorless, crystalline ethyl 7-(3-azidomethyl-4-cyano)phenyl-1-cyclopropyl-6-fluoro-8-methoxy-1,4-dihydro-4-oxoquinoline-3-carboxylate.

IR (KBr) cm$^{-1}$: –N3 2103, $v_{C=O}$ 1728

NMR (CDCl$_3$) δ value: 0.80–1.70 (7H, m), 3.37 (3H, s), 3.70–4.10 (1H, m), 4.40 (2H, q, J=7.0 Hz), 4.70 (2H, s), 7.15–8.20 (4H, m), 8.64 (1H, s)

(3) To a suspension of 302 mg of stannous chloride in 2 ml of methanol were dropwise added 3 ml of a methanol solution of 210 mg of the compound obtained in (2) above at room temperature over about one hour, and the resulting mixture was stirred at the same temperature for 30 minutes. The solvent was removed by distillation under reduced pressure, and to the residue obtained were added 10 ml of chloroform and 10 ml of a saturated aqueous potassium carbonate solution, after which insolubles were removed by filtration through Celite. The filtrate obtained was allowed to separate into two layers, and the organic layer formed was washed successively with a saturated aqueous potassium carbonate solution and a saturated saline solution and then dried over anhydrous magnesium sulfate. The solvent was removed by distillation under reduced pressure, and the residue obtained was purified by a column chromatography [eluent: the organic layer of (chloroform:ethanol:conc.ammonia water=150:25:1)], to obtain 100 mg of a mixture of methyl ester and ethyl ester of 1-cyclopropyl-6-fluoro-7-(1-iminoisoindolin-5-yl)-8-methoxy-1,4-dihydro-4-oxoquinoline-3-carboxylic acid.

(4) To a suspension of 100 mg of the mixture obtained in (3) above in 2 ml of ethanol and 2 ml of dioxane was added 1 ml of 1N aqueous sodium hydroxide solution, and the resulting mixture was stirred at room temperature for two hours. The solvent was removed by distillation under reduced pressure, and to the residue obtained was added 2 ml of water, after which insolubles were removed by filtration. A carbon dioxide gas was blown into the filtrate obtained and the crystals precipitated were collected by filtration, to obtain 56 mg of colorless, crystalline 1-cyclopropyl-6-fluoro-7-(1-iminoisoindolin-5-yl)-8-methoxy-1,4-dihydro-4-oxoquinoline-3-carboxylic acid.

IR (KBr) cm$^{-1}$: $v_{C=O}$ 1617

NMR (d$_1$-TFA) δ value: 1.20–1.80 (4H, m), 3.61 (3H, s), 4.35–5.20 (3H, m), 7.70–8.50 (4H, m), 9.53 (1H, s)

EXAMPLE 7

In 3 ml of ethanol was suspended 0.30 g of ethyl 1-cyclopropyl-6-fluoro-8-methyl-7-[2-(p-toluenesulfonyl)isoindolin-5-yl]-1,4-dihydro-4-oxoquinoline-3-carboxylate, and 3 ml of 1N aqueous sodium hydroxide solution and 3 ml of dioxane were added to the suspension, after which the resulting mixture was stirred at room temperature for two hours. To the reaction mixture was added 3 ml of 1N hydrochloric acid, and the crystals thus formed were collected by filtration, to obtain 0.27 g of colorless, crystalline 1-cyclopropyl-6-fluoro-8-methyl-7-[2-(p-toluenesulfonyl)isoindolin-5-yl]-1,4-dihydro-4-oxoquinoline-3-carboxylic acid.

IR (KBr) cm$^{-1}$: $\nu_{C=O}$ 1726

NMR (d$_1$-TFA) δ value: 1.10–1.90 (4H, m), 2.48 (3H, s), 2.89 (3H, s), 4.50–5.00 (5H, m), 6.90–8.00 (7H, m), 8.30 (1H, d, J=7.8 Hz), 9.62 (1H, s)

In the same manner, the following compounds were obtained.

1-Cyclopropyl-6-fluoro-7-[2-(p-toluenesulfonyl)isoindolin-5-yl]-1,4-dihydro-4-oxoquinoline-3-carboxylic acid IR (KBr) cm$^{-1}$: $\nu_{C=O}$ 1724

NMR (d$_1$-TFA) δ value: 1.10–1.90 (4H, m), 2.47 (3H, s), 3.80–4.45 (1H, m), 4.87 (4H, s), 7.10–8.00 (7H, m), 8.44 (1H, d, J=9.3 Hz), 8.74 (1H, d, J=5.9 Hz), 9.46 (1H, s)

(S)-9-fluoro-3-methyl-7-oxo-10-[2-(p-toluenesulfonyl)isoindolin-5-yl]-2,3-dihydro-7H-pyrido[1,2,3-de][1,4]benzoxazine-6-carboxylic acid IR (KBr) cm$^{-1}$: $\nu_{C=O}$ 1723

NMR (d$_1$-TFA) δ value: 1.83 (3H, d, J=6.8 Hz), 2.47 (3H, s), 4.40–5.50 (7H, m), 7.00–8.30 (8H, m), 9.35 (1H, s)

1-Cyclopropyl-6-fluoro-7-[2-(p-toluenesulfonyl)isoindolin-5-yl]-1,4-dihydro-4-oxo-1,8-naphthyridine-3-carboxylic acid IR (KBr) cm$^{-1}$: $\nu_{C=O}$ 1718

NMR (d$_1$-TFA) δ value: 1.20–1.90 (4H, m), 2.47 (3H, s), 4.20–4.70 (1H, m), 4.89 (4H, s), 7.20–8.90 (8H, m), 9.53 (1H, s)

1-Cyclopropyl-6,8-difluoro-7-[2-(p-toluenesulfonyl)isoindolin-5-yl]-1,4-dihydro-4-oxoquinoline-3-carboxylic acid IR (KBr) cm$^{-1}$: $\nu_{C=O}$ 1729

NMR (CDCl$_3$) δ value: 0.90–1.80 (4H, m), 2.38 (3H, s), 3.60–4.30 (1H, m), 4.67 (4H, s), 7.00–8.30 (8H, m), 8.83 (1H, s), 14.0 (1H, brs)

8-Chloro-1-cyclopropyl-6-fluoro-7-[2-(p-toluenesulfonyl)isoindolin-5-yl]-1,4-dihydro-4-oxoquinoline-3-carboxylic acid IR (KBr) cm$^{-1}$: $\nu_{C=O}$ 1728

NMR (CDCl$_3$) δ value: 0.70–1.50 (4H, m), 2.39 (3H, s), 4.00–4.50 (1H, m), 4.67 (4H, s), 6.80–7.90 (7H, m), 8.13 (1H, d, J=8.8 Hz), 8.93 (1H, s), 14.0 (1H, brs)

1-Cyclopropyl-7-[4,7-difluoro-2-(p-toluenesulfonyl)isoindolin-5-yl]-6-fluoro-1,4-dihydro-4-oxoquinoline-3-carboxylic acid IR (KBr) cm$^{-1}$: $\nu_{C=O}$ 1734

NMR (d$_1$-TFA) δ value: 1.10–1.85 (4H, m), 2.49 (3H, s), 4.00–4.45 (1H, m), 4.92 (4H, s), 7.10–8.10 (5H, m), 8.47 (1H, d, J=8.5 Hz), 8.77 (1H, d, J=5.5 Hz), 9.49 (1H, s)

1-Cyclopropyl-7-[4,7-difluoro-2-(p-toluenesulfonyl)isoindolin-5-yl]-6-fluoro-8-methoxy-1,4-dihydro-4-oxoquinoline-3-carboxylic acid IR (KBr) cm$^{-1}$: $\nu_{C=O}$ 1730

NMR (CDCl$_3$) δ value: 0.90–1.70 (4H, m), 2.40 (3H, s), 3.47 (3H, s), 3.80–4.30 (1H, m), 4.81 (4H, s), 6.80–8.20 (6H, m), 8.85 (1H, s), 14.2 (1H, brs)

1-(2,4-Difluolophenyl)-6-fluoro-7-[2-(p-toluenesulfonyl)isoindolin-5-yl]-1,4-dihydro-4-oxo-1,8-naphthyridine-3-carboxylic acid IR (KBr) cm$^{-1}$: $\nu_{C=O}$ 1724

NMR (d$_1$-TFA) δ value: 2.46 (3H, s), 4.78 (4H, s), 7.05–8.15 (10H, m), 8.71 (1H, d, J=10.0 Hz), 9.50 (1H, s)

7-[2-(Benzyloxycarbonyl)isoindolin-5-yl]-1-cyclopropyl-6-fluoro-8-fluoromethyl-1,4-dihydro-4-oxoquinoline-3-carboxylic acid IR (KBr) cm$^{-1}$: $\nu_{C=O}$ 1713

NMR (CDCl$_3$) δ value: 0.75–1.60 (4H, m), 4.00–4.50 (1H, m), 4.85 (4H, s), 5.23 (2H, s), 5.70 (2H, d, J=47 Hz), 6.80–7.75 (8H, m), 8.28 (1H, d, J=7.5 Hz), 8.95 (1H, s), 14.1 (1H, brs)

1-Cyclopropyl-6-fluoro-8-methoxy-7-[2-(p-toluenesulfonyl)isoindolin-5-yl]-1,4-dihydro-4-oxoquinoline-3-carboxylic acid IR (KBr) cm$^{-1}$: $\nu_{C=O}$ 1727

NMR (CDCl$_3$) δ value: 1.00–1.50 (4H, m), 2.40 (3H, s), 3.34 (3H, s), 3.80–4.40 (1H, m), 4.69 (4H, brs), 6.90–8.20 (8H, m), 8.86 (1H, s), 14.3 (1H, brs)

1-Cyclopropyl-6-fluoro-8-methoxy-7-[1-methyl-2-(p-toluenesulfonyl)isoindolin-5-yl]-1,4-dihydro-4-oxoquinoline-3-carboxylic acid IR (KBr) cm$^{-1}$: $\nu_{C=O}$ 1734

NMR (d$_1$-TFA) δ value: 1.20–2.00 (7H, m), 2.45 (3H, s), 3.54 (3H, s), 4.35–5.45 (4H, m), 7.00–7.95 (7H, m), 8.20 (1H, d, J=8.5 Hz), 9.49 (1H, s)

1-Cyclopropyl-6-fluoro-8-methoxy-7-[3-methyl-2-(p-toluenesulfonyl)isoindolin-5-yl]-1,4-dihydro-4-oxoquinoline-3-carboxylic acid IR (KBr) cm$^{-1}$: $\nu_{C=O}$ 1728

NMR (CDCl$_3$—D$_2$O) δ value: 0.90–1.45 (4H, m), 1.68 (3H, d, J=6.5 Hz), 2.39 (3H, s), 3.34 (3H, s), 3.80–4.30 (1H, m), 4.55–5.25 (3H, m), 7.05–8.10 (8H, m), 8.85 (1H, s)

1-Cyclopropyl-8-difluoromethoxy-6-fluoro-7-[2-(p-toluenesulfonyl)isoindolin-5-yl]-1,4-dihydro-4-oxoquinoline-3-carboxylic acid IR (KBr) cm$^{-1}$: $\nu_{C=O}$ 1732

NMR (CDCl$_3$+CD$_3$OD) δ value: 0.90–1.50 (4H, m), 2.42 (3H, s), 3.90–4.35 (1H, m), 4.70 (4H, s), 5.91 (1H, t, J=75 Hz), 7.15–7.95 (7H, m), 8.18 (1H, d, J=9.0 Hz), 8.92 (1H, s)

1-Cyclopropyl-8-difluoromethoxy-6-fluoro-7-[3-methyl-2-(p-toluenesulfonyl)isoindolin-5-yl]-1,4-dihydro-4-oxoquinoline-3-carboxylic acid IR (KBr) cm$^{-1}$: $\nu_{C=O}$ 1732

NMR (CDCl₃) δ value: 0.80–1.95 (7H, m), 2.39 (3H, s), 3.85–4.35 (1H, m), 4.45–5.25 (3H, m), 5.82 (1H, t, J=74 Hz), 7.10–7.50 (5H, m), 7.55–7.90 (2H, m), 8.18 (1H, d, J=8.8 Hz), 8.91 (1H, s), 14.0 (1H, brs)

1-Cyclopropyl-6-fluoro-8-fluoromethoxy-7-[2-(p-toluenesulfonyl)isoindolin-5-yl]-1,4-dihydro-4-oxoquinoline-3-carboxylic acid IR (KBr) cm⁻¹: $v_{C=O}$ 1732

NMR (CDCl₃) δ value: 0.80–1.50 (4H, m), 2.42 (3H, s), 3.90–4.40 (1H, m), 4.69 (4H, s), 5.06 (2H, d, J=53 Hz), 7.00–7.80 (7H, m), 8.12 (1H, d, J=8.8 Hz), 8.91 (1H, s), 14.2 (1H, brs)

1-Cyclopropyl-6-fluoro-7-[1-methyl-2-(p-toluenesulfonyl)isoindolin-5-yl]-1,4-dihydro-4-oxoquinoline-3-carboxylic acid IR (KBr) cm⁻¹: $v_{C=O}$ 1751, 1734

NMR (d₁-TFA) δ value: 1.20–2.10 (7H, m), 2.45 (3H, s), 3.90–4.50 (1H, m), 4.60–5.50 (3H, m), 7.10–8.05 (7H, m), 8.42 (1H, d, J=9.5 Hz), 8.74 (1H, d, J=6.0 Hz), 9.46 (1H, s)

1-Cyclopropyl-6-fluoro-7-[3-methyl-2-(p-toluenesulfonyl)isoindolin-5-yl]-1,4-dihydro-4-oxoquinoline-3-carboxylic acid IR (KBr) cm⁻¹: $v_{C=O}$ 1754, 1736

NMR (d₁-TFA) δ value: 1.25–2.00 (7H, m), 2.46 (3H, s), 3.95–4.45 (1H, m), 4.65–5.50 (3H, m), 7.20–8.10 (7H, m), 8.44 (1H, d, J=9.5 Hz), 8.74 (1H, d, J=6.0 Hz), 9.46 (1H, s)

7-[2-(Benzyloxycarbonyl)isoindolin-5-yl]-8-chloro-6-fluoro-1-[(1R,2S)-2-fluorocyclopropyl]-1,4-dihydro-4-oxoquinoline-3-carboxylic acid IR (KBr) cm⁻¹: $v_{C=O}$ 1708

NMR (CDCl₃) δ value: 0.90–2.20 (2H, m), 3.80–5.00 (5.5H, m), 5.00–5.50 (2.5H, m), 6.90–7.50 (8H, m), 8.20 (1H, d, J=7.8 Hz), 8.88 (1H, brs), 13.7 (1H, brs)

6-Fluoro-1-(2-fluoroethyl)-8-methyl-7-[2-(p-toluenesulfonyl)isoindolin-5-yl]-1,4-dihydro-4-oxoquinoline-3-carboxylic acid IR (KBr) cm⁻¹: $v_{C=O}$ 1718

NMR (d₁-TFA) δ value: 2.47 (3H, s), 2.65 (3H, s), 3.70–6.00 (8H, m), 7.00–8.10 (7H, m), 8.36 (1H, d, J=8.0 Hz), 9.46 (1H, s)

1-Ethyl-6-fluoro-8-methyl-7-[2-(p-toluenesulfonyl)isoindolin-5-yl]-1,4-dihydro-4-oxoquinoline-3-carboxylic acid IR (KBr) cm⁻¹: $v_{C=O}$ 1720

NMR (CDCl₃) δ value: 1.46 (3H, t, J=7.3 Hz), 2.41 (6H, s), 4.15–4.90 (6H, m), 6.90–7.90 (7H, m), 8.14 (1H, d, J=9.3 Hz), 8.74 (1H, s), 14.4 (1H, brs)

6-Fluoro-1-[(1R,2S)-2-fluorocyclopropyl]-8-methyl-7-[2-(p-toluenesulfonyl)isoindolin-5-yl]-1,4-dihydro-4-oxoquinoline-3-carboxylic acid IR (KBr) cm⁻¹: $v_{C=O}$ 1726

NMR (CDCl₃) δ value: 0.80–2.30 (2H, m), 2.42 (3H, s), 2.51 (3H, s), 3.70–4.90 (5.5H, m), 5.10–5.60 (0.5H, m), 6.80–8.15 (8H, m), 8.83 (1H, d, J=2.9 Hz)

1-(2,4-Difluorophenyl)-6-fluoro-8-methyl-7-[2-(p-toluenesulfonyl)isoindolin-5-yl]-1,4-dihydro-4-oxoquinoline-3-carboxylic acid IR (KBr) cm⁻¹: $v_{C=O}$ 1734

1-(4-Benzyloxyphenyl)-6-fluoro-8-methyl-7-[2-(p-toluenesulfonyl)isoindolin-5-yl]-1,4-dihydro-4-oxoquinoline-3-carboxylic acid IR (KBr) cm⁻¹: $v_{C=O}$ 1728

NMR (d₁-TFA) δ value: 1.81 (3H, s), 2.46 (3H, s), 4.60–5.70 (6H, m), 6.90–8.20 (16H, m), 8.41 (1H, d, J=8.3 Hz), 9.32 (1H, s)

6-Fluoro-1-(2-fluoroethyl)-7-[2-(p-toluenesulfonyl)isoindolin-5-yl]-1,4-dihydro-4-oxoquinoline-3-carboxylic acid IR (KBr) cm⁻¹: $v_{C=O}$ 1719

NMR (d₁-TFA) δ value: 2.47 (3H, s), 4.40–5.60 (8H, m), 7.10–8.60 (9H, m), 9.45 (1H, s)

1-(2,4-Difluorophenyl)-6-fluoro-7-[2-(p-toluenesulfonyl)isoindolin-5-yl]-1,4-dihydro-4-oxoquinoline-3-carboxylic acid IR (KBr) cm⁻¹: $v_{C=O}$ 1719

7-[2-(benzyloxycarbonyl)isoindolin-5-yl]-1-cyclopropyl-6-fluoro-8-methoxy-5-nitro-1,4-dihydro-4-oxoquinoline-3-carboxylic acid IR (KBr) cm⁻¹: $v_{C=O}$ 1736, 1702

NMR (CDCl₃) δ value: 0.80–1.80 (4H, m), 3.45 (3H, s), 3.80–4.30 (1H, m), 4.86 (4H, s), 5.23 (2H, s), 7.10–7.50 (8H, m), 8.92 (1H, s), 13.3 (1H, brs)

EXAMPLE 8

In 5.3 ml of 47% hydrobromic acid was suspended 0.53 g of 1-cyclopropyl-6-fluoro-8-methyl-7-[2-(p-toluenesulfonyl)isoindolin-5-yl]-1,4-dihydro-4-oxoquinoline-3 carboxylic acid, and 0.28 g of phenol and 3.2 ml of propionic acid were added to the suspension, after which the resulting mixture was heated under reflux for one hour under a nitrogen stream. The reaction mixture was concentrated under reduced pressure, and ethanol was added to the residue obtained, after which the crystals formed were collected by filtration, to obtain 0.38 g of colorless, crystalline 1-cyclopropyl-6-fluoro-8-methyl-7-(isoindolin-5-yl)-1,4-dihydro-4-oxoquinoline-3-carboxylic acid hydrobromide. The hydrobromide obtained was suspended in 3.8 ml of ethanol and then dissolved in 7.6 ml of 0.5N aqueous sodium hydroxide solution, after which a carbon dioxide gas was blown into the solution. The crystals formed were collected by filtration, to obtain 0.27 g of colorless, crystalline 1-cyclopropyl-6-fluoro-8-methyl-7-(isoindolin-5-yl)-1,4-dihydro-4-oxoquinoline-3-carboxylic acid.

IR (KBr) cm⁻¹: $v_{C=O}$ 1643

NMR (d₁-TFA) δ value: 0.90–2.00 (4H, m), 2.94 (3H, s), 4.40–5.30 (5H, m), 7.10–7.85 (3H, m), 8.35 (1H, d, J=7.8 Hz), 9.63 (1H, s)

In the same manner, the following compounds were obtained.

1-Cyclopropyl-6-fluoro-7-(isoindolin-5-yl)-1,4-dihydro-4-oxoquinoline-3-carboxylic acid IR (KBr) cm$^{-1}$: $\nu_{C=O}$ 1615

NMR (d$_1$-TFA) δ value: 1.20–2.10 (4H, m), 4.00–4.60 (1H, m), 5.04 (4H, s), 7.40–8.10 (3H, m), 8.49 (1H, d, J=9.3 Hz), 8.74 (1H, d, J=5.9 Hz), 9.49 (1H, s)

(S)-9-Fluoro-3-methyl-10-(isoindolin-5-yl)-7-oxo-2,3-dihydro-7H-pyrido[1,2,3-de][1,4]benzoxazine-6-carboxylic acid IR (KBr) cm$^{-1}$: $\nu_{C=O}$ 1717

NMR (d$_1$-TFA) δ value: 1.85 (1H, d, J=6.8 Hz), 4.10–5.50 (7H, m), 7.64 (3H, s), 8.12 (1H, d, J=8.8 Hz), 9.37 (1H, s)

1-Cyclopropyl-6-fluoro-7-(isoindolin-5-yl)-1,4-dihydro-4-oxo-1,8-naphthyridine-3-carboxylic acid IR (KBr) cm$^{-1}$: $\nu_{C=O}$ 1617

NMR (d$_1$-TFA) δ value: 1.00–2.00 (4H, m), 4.10–4.70 (1H, m), 5.03 (4H, s), 7.30–9.00 (4H, m), 9.53 (1H, s)

1-Cyclopropyl-6,8-difluoro-7-(isoindolin-5-yl)-1,4-dihydro-4-oxoquinoline-3-carboxylic acid IR (KBr) cm$^{-1}$: $\nu_{C=O}$ 1616

NMR (d$_1$-TFA) δ value: 1.30–2.00 (4H, m), 4.30–5.30 (5H, m), 7.71 (3H, s), 8.37 (1H, d, J=7.8 Hz), 9.52 (1H, s)

8-Chloro-1-cyclopropyl-6-fluoro-7-(isoindolin-5-yl)-1,4-dihydro-4-oxoquinoline-3-carboxylic acid IR (KBr) cm$^{-1}$: $\nu_{C=O}$ 1636

NMR (d$_1$-TFA) δ value: 1.10–1.90 (4H, m), 4.60–5.20 (5H, m), 7.30–7.80 (3H, m), 8.43 (1H, d, J=6.8 Hz), 9.63 (1H, s)

1-Cyclopropyl-7-(4,7-difluoroisoindolin-5-yl)-6-fluoro-1,4-dihydro-4-oxoquinoline-3-carboxylic acid IR (KBr) cm$^{-1}$: $\nu_{C=O}$ 1720

NMR (d$_1$-TFA) δ value: 1.15–1.95 (4H, m), 3.95–4.60 (1H, m), 5.13 (4H, s), 7.15–7.65 (1H, m), 8.51 (1H, d, J=8.8 Hz), 8.84 (1H, d, J=5.4 Hz), 9.51 (1H, s)

1-Cyclopropyl-7-(4,7-difluoroisoindolin-5-yl)-6-fluoro-8-methoxy-1,4-dihydro-4-oxoquinoline-3-carboxylic acid IR (KBr) cm$^{-1}$: $\nu_{C=O}$ 1734

NMR (d$_1$-TFA) δ value: 1.20–1.80 (4H, m), 3.75 (3H, s), 4.45–4.95 (1H, m), 5.15 (4H, s), 7.20–7.55 (1H, m), 8.24 (1H, d, J=8.5 Hz), 9.50 (1H, s)

1-(2,4-Difluorophenyl)-6-fluoro-7-(isoindolin-5-yl)-1,4-dihydro-4-oxo-1,8-naphthyridine-3-carboxylic acid IR (KBr) cm$^{-1}$: $\nu_{C=O}$ 1654

NMR (d$_1$-TFA) δ value: 4.99 (4H, brs), 6.90–8.40 (6H, m), 8.78 (1H, d, J=9.5 Hz), 9.50 (1H, s)

1-Cyclopropyl-6-fluoro-7-(isoindolin-5-yl)-8-methoxy-1,4-dihydro-4-oxoquinoline-3-carboxylic acid IR (KBr) cm$^{-1}$: $\nu_{C=O}$ 1637

NMR (d$_1$-TFA) δ value: 1.20–1.80 (4H, m), 3.62 (3H, s), 4.40–5.20 (5H, m), 7.73 (3H, brs), 8.26 (1H, d, J=8.3 Hz), 9.50 (1H, s)

1-Cyclopropyl-6-fluoro-8-methoxy-7-(1-methylisoindolin-5-yl)-1,4-dihydro-4-oxoquinoline-3-carboxylic acid IR (KBr) cm$^{-1}$: $\nu_{C=O}$ 1726

NMR (d$_1$-TFA) δ value: 1.30–2.20 (7H, m), 3.60 (3H, s), 4.50–5.60 (4H, m), 7.30–8.00 (3H, m), 8.26 (1H, d, J=8.3 Hz), 9.51 (1H, s)

1-Cyclopropyl-6-fluoro-8-methoxy-7-(3-methylisoindolin-5-yl)-1,4-dihydro-4-oxoquinoline-3-carboxylic acid IR (KBr) cm$^{-1}$: $\nu_{C=O}$ 1629

NMR (d$_1$-TFA) δ value: 1.10–2.10 (7H, m), 3.62 (3H, s), 4.30–5.65 (4H, m), 7.20–7.80 (3H, m), 8.29 (1H, d, J=8.3 Hz), 9.50 (1H, s)

1-Cyclopropyl-8-difluoromethoxy-6-fluoro-7-(isoindolin-5-yl)-1,4-dihydro-4-oxoquinoline-3-carboxylic acid IR (KBr) cm$^{-1}$: $\nu_{C=O}$ 1636

NMR (d$_1$-TFA) δ value: 1.00–2.00 (4H, m), 4.30–5.20 (5H, m), 6.20 (1H, t, J=72 Hz), 7.72 (3H, brs), 8.46 (1H, d, J=8.3 Hz), 9.58 (1H, s)

1-Cyclopropyl-8-difluoromethoxy-6-fluoro-7-(3-methylisoindolin-5-yl)-1,4-dihydro-4-oxoquinoline-3-carboxylic acid IR (KBr) cm$^{-1}$: $\nu_{C=O}$ 1638

NMR (d$_1$-TFA) δ value: 1.15–2.15 (7H, m), 4.45–5.15 (3H, m), 5.15–5.70 (1H, m), 6.20 (1H, t, J=72 Hz), 7.30–7.95 (3H, m), 8.46 (1H, d, J=8.3 Hz), 9.59 (1H, s)

1-Cyclopropyl-6-fluoro-8-fluoromethoxy-7-(isoindolin-5-yl)-1,4-dihydro-4-oxoquinoline-3-carboxylic acid IR (KBr) cm$^{-1}$: $\nu_{C=O}$ 1732

NMR (d$_1$-TFA) δ value: 1.00–2.00 (4H, m), 4.50–5.25 (5H, m), 5.28 (2H, d, J=52 Hz), 7.20–7.90 (3H, m), 8.39 (1H, d, J=8.3 Hz), 9.56 (1H, s)

1-Cyclopropyl-6-fluoro-7-(1-methylisoindolin-5-yl)-1,4-dihydro-4-oxoquinoline-3-carboxylic acid IR (KBr) cm$^{-1}$: $\nu_{C=O}$ 1618

NMR (d$_1$-TFA) δ value: 1.30–2.20 (7H, m), 4.00–4.50 (1H, m), 4.80–5.70 (3H, m), 7.40–8.00 (3H, m), 8.49 (1H, d, J=9.0 Hz), 8.79 (1H, d, J=6.0 Hz), 9.49 (1H, s)

1-Cyclopropyl-6-fluoro-7-(3-methylisoindolin-5-yl)-1,4-dihydro-4-oxoquinoline-3-carboxylic acid IR (KBr) cm$^{-1}$: $\nu_{C=O}$ 1618

NMR (d$_1$-TFA) δ value: 1.20–2.15 (7H, m), 3.95–4.50 (1H, m), 4.70–5.70 (3H, m), 7.40–8.05 (3H, m), 8.15–9.00 (2H, m), 9.44 (1H, s)

6-Fluoro-1-(2-fluoroethyl)-7-(isoindolin-5-yl)-8-methyl-1,4-dihydro-4-oxoquinoline-3-carboxylic acid IR (KBr) cm$^{-1}$: $\nu_{C=O}$ 1628

NMR (d$_1$-TFA) δ value: 2.73 (3H, s), 4.00–6.00 (8H, m), 7.00–7.90 (3H, m), 8.44 (1H, d, J=7.3 Hz), 9.53 (1H, s)

1-Ethyl-6-fluoro-7-(isoindolin-5-yl)-8-methyl-1,4-dihydro- 4-oxoquinoline-3-carboxylic acid IR (KBr) cm$^{-1}$: ν$_{C=O}$ 1633

NMR (d$_1$-TFA) δ value: 1.76 (3H, t, J=7.3 Hz), 2.78 (3H, s), 4.80–5.50 (6H, m), 7.30–7.70 (3H, m), 8.41 (1H, d, J=7.8 Hz), 9.45 (1H, s)

6-Fluoro-1-[(1R,2S)-2-fluorocyclopropyl]-7-(isoindolin-5-yl)-8-methyl-1,4-dihydro-4-oxoquinoline-3-carboxylic acid IR (KBr) cm$^{-1}$: ν$_{C=O}$ 1634

NMR (d$_1$-TFA) δ value: 1.20–2.40 (2H, m), 2.88 (3H, s), 4.30–5.90 (6H, m), 7.10–7.90 (3H, m), 8.35 (1H, d, J=7.3 Hz), 9.53 (1H, s)

1-(2,4-Difluorophenyl)-6-fluoro-7-(isoindolin-5-yl)-8-methyl-1,4-dihydro-4-oxoquinoline-3-carboxylic acid IR (KBr) cm$^{-1}$: ν$_{C=O}$ 1636

NMR (d$_1$-TFA) δ value: 1.90 (3H, s), 4.50–5.20 (4H, m), 6.80–8.00 (6H, m), 8.45 (1H, d, J=7.8 Hz), 9.35 (1H, s)

6-Fluoro-1-(4-hydroxyphenyl)-7-(isoindolin-5-yl)-8-methyl-1,4-dihydro-4-oxoquinoline-3-carboxylic acid IR (KBr) cm$^{-1}$: ν$_{C=O}$ 1622

NMR (d$_1$-TFA) δ value: 1.95 (3H, s), 4.98 (4H, brs), 6.50–7.80 (7H, m), 8.48 (1H, d, J=7.7 Hz), 9.32 (1H, s)

6-Fluoro-1-(2-fluoroethyl)-7-(isoindolin-5-yl)-1,4-dihydro-4-oxoquinoline-3-carboxylic acid IR (KBr) cm$^{-1}$: ν$_{C=O}$ 1618

NMR (d$_1$-TFA) δ value: 4.40–5.80 (8H, m), 7.50–8.10 (3H, m), 8.20–8.80 (2H, m), 9.48 (1H, s)

1-(2,4-Difluorophenyl)-6-fluoro-7-(isoindolin-5-yl)-1,4-dihydro-4-oxoquinoline-3-carboxylic acid IR (KBr) cm$^{-1}$: ν$_{C=O}$ 1622

NMR (d$_1$-TFA) δ value: 4.96 (4H, brs), 7.00–8.00 (7H, m), 8.56 (1H, d, J=9.3 Hz), 9.38 (1H, s)

EXAMPLE 9

In 0.5 ml of 47% hydrobromic acid was suspended 50 mg of 1-cyclopropyl-6-fluoro-8-methoxy-7-[2-(p-toluenesulfonyl)isoindolin-5-yl]-1,4-dihydro-4-oxoquinoline-3-carboxylic acid, and to the suspension were added 26 mg of phenol and 0.3 ml of propionic acid, after which the resulting mixture was stirred at 130° C. for six hours. The reaction mixture was concentrated under reduced pressure, and to the residue obtained were added 0.3 ml of ethanol, 0.3 ml of 1N aqueous sodium hydroxide solution and 0.3 ml of water to dissolve the residue. Thereafter, a carbon dioxide gas was blown into the solution, and the crystals precipitated were collected by filtration, to obtain 12 mg of pale yellow, crystalline 1-cyclopropyl-6-fluoro-8-hydroxy-7-(isoindolin-5-yl)-1,4-dihydro-4-oxoquinoline-3-carboxylic acid.

IR (KBr) cm$^{-1}$: ν$_{C=O}$ 1613

NMR (d$_1$-TFA) δ value: 1.00–1.80 (4H, m), 4.50–5.20 (5H, m), 7.66 (3H, brs), 8.00 (1H, d, J=8.6 Hz), 9.44 (1H, s)

EXAMPLE 10

To a suspension of 210 mg of ethyl 1-cyclopropyl-6-fluoro-8-methoxy-7-[2-trifluoroacetyl-spiro[isoindolin-1,1'-cyclopropan]-5-yl]-1,4-dihydro-4-oxoquinoline-3-carboxylate in 4.2 ml of ethanol were added 2.1 ml of 1N aqueous sodium hydroxide solution and 4.2 ml of dioxane, after which the resulting mixture was heated with stirring at 40° C. for three hours. The reaction mixture was cooled to room temperature, and thereafter, insolubles were removed by filtration, after which a carbon dioxide gas was blown in the filtrate obtained. The crystals precipitated were collected by filtration, to obtain 140 mg of pale yellow, crystalline 1-cyclopropyl-6-fluoro-8-methoxy-7-[spiro[isoindolin-1,1'-cyclopropan]-5-yl]-1,4-dihydro-4-oxoquinoline-3-carboxylic acid.

IR (KBr) cm$^{-1}$: ν$_{C=O}$ 1618

NMR (d6-DMSO) δ value: 0.80–1.50 (6H, m), 2.40–2.80 (2H, m), 3.43 (3H, s), 4.00–4.40 (3H, m), 6.90–7.60 (3H, m), 7.90 (1H, d, J=9.0 Hz), 8.85 (1H, s)

In the same manner, the following compound was obtained.

1-Cyclopropyl-8-difluoromethoxy-6-fluoro-7-[spiro[isoindolin-1,1'-cyclopropan]-5-yl]-1,4-dihydro-4-oxoquinoline-3-carboxylic acid IR (KBr) cm$^{-1}$: ν$_{C=O}$ 1636

NMR (d6-DMSO) δ value: 0.90–1.40 (6H, m), 2.40–2.60 (2H, m), 3.50–4.40 (3H, m), 6.67 (1H, t, J=73 Hz), 6.80–7.50 (3H, m), 8.11 (1H, d, J=9.0 Hz), 8.88 (1H, s)

EXAMPLE 11

In 25 ml of acetic acid and 50 mg of 5% palladium carbon was suspended 150 mg of 7-[2-(benzyloxycarbonyl)-isoindolin-5-yl]-8-chloro-6-fluoro-1-[(1R,2S)-2-fluorocyclopropyl]-1,4-dihydro-4-oxoquinoline-3-carboxylic acid, and the suspension was stirred at room temperature for two hours under a hydrogen stream. The reaction mixture was filtered and thereafter 2 ml of 6N hydrochloric acid was added to the filtrate obtained, after which the mixture was concentrated under reduced pressure. To the residue obtained were added ethanol, and the crystals formed were collected by filtration. To the crystals obtained were added 0.7 ml of ethanol, 0.7 ml of 1N aqueous sodium hydroxide solution and 0.7 ml of water to dissolve the crystals, and thereafter, dilute acetic acid was added to the solution to adjust the pH to 7. The crystals precipitated were collected by filtration, to obtain 45 mg of colorless, crystalline 8-chloro-6-fluoro-1-[(1R,2S)-2-fluorocyclopropyl]-7-(isoindolin-5-yl)-1,4-dihydro-4-oxoquinoline-3-carboxylic acid.

IR (KBr) cm$^{-1}$: ν$_{C=O}$ 1641

NMR (d$_1$-TFA) δ value: 1.30–2.30 (2H, m), 4.30–5.90 (6H, m), 7.20–7.80 (3H, m), 8.46 (1H, d, J=7.3 Hz), 9.56 (1H, s)

EXAMPLE 12

In 10 ml of acetic acid and 60 mg of 5% palladium carbon was suspended 85 mg of 7-[2-(benzyloxycarbonyl)

isoindolin-5-yl]-1-cyclopropyl-6-fluoro-8-methoxy-5-nitro-1,4-dihydro-4-oxoquinoline-3-carboxylic acid, and the suspension was stirred at room temperature for two hours under a hydrogen stream. The reaction mixture was filtered, and thereafter, 2 ml of 6N hydrochloric acid was added to the filtrate obtained, after which the resulting mixture was concentrated under reduced pressure. To the residue obtained were added ethanol, and the crystals formed were collected by filtration. To the crystals obtained were added 0.5 ml of ethanol, 0.5 ml of 1N aqueous sodium hydroxide solution and 0.5 ml of water to dissolve the crystals. Thereafter, a carbon dioxide gas was blown into the solution, and the crystals precipitated were collected by filtration, to obtain 55 mg of pale yellow, crystalline 5-amino-1-cyclopropyl-6-fluoro-7-(isoindolin-5-yl)-8-methoxy-1,4-dihydro-4-oxoquinoline-3-carboxylic acid.

IR (KBr) cm$^{-1}$: $v_{C=O}$ 1716

NMR (d$_1$-TFA) δ value: 0.70–1.70 (4H, m), 3.58 (3H, s), 4.00–4.70 (1H, m), 5.02 (4H, brs), 7.70 (3H, brs), 9.29 (1H, s)

EXAMPLE 13

In 3.2 ml of 30% hydrogen bromide-acetic acid solution was suspended 0.16 g of 7-[2-(benzyloxycarbonyl)isoindolin-5-yl]-1-cyclopropyl-6-fluoro-8-fluoromethyl-1,4-dihydro-4-oxoquinoline-3-carboxylic acid, and the suspension was stirred at room temperature for 40 minutes. The reaction mixture was concentrated under reduced pressure and to the residue was added ethanol, and the crystals formed were collected by filtration. The crystals obtained were dissolved in dilute aqueous sodium hydroxide solution, and the pH was adjusted to 7 with dilute hydrochloric acid. The crystals precipitated were collected by filtration, to obtain 68 mg of colorless, crystalline 1-cyclopropyl-6-fluoro-8-fluoromethyl-7-(isoindolin-5-yl)-1,4-dihydro-4-oxoquinoline-3-carboxylic acid.

IR (KBr) cm$^{-1}$: $v_{C=O}$ 1638

NMR (d$_1$-TFA) δ value: 1.10–2.05 (4H, m), 4.65–5.25 (5H, m), 5.96 (2H, d, J=47 Hz), 7.25–7.85 (3H, m), 8.52 (1H, d, J=7.8 Hz), 9.65 (1H, s)

EXAMPLE 14

In 0.50 ml of formic acid was suspended 50 mg of 1-cyclopropyl-6-fluoro-7-(isoindolin-5-yl)-1,4-dihydro-4-oxoquinoline-3-carboxylic acid hydrobromide, and 27 mg of formalin was added to the suspension, after which the mixture was heated under reflux for two hours. The solvent was then removed by distillation under reduced pressure. To the residue obtained was added 5 ml of water and the pH was adjusted to 7 with a saturated aqueous sodium hydrogencarbonate solution, after which the resulting mixture was extracted with five 5 ml portions of chloroform. The resulting chloroform layer was dried over anhydrous magnesium sulfate and then the solvent was removed by distillation under reduced pressure. Ethanol was added to the residue obtained and the crystals formed were collected by filtration, to obtain 29 mg of pale yellow, crystalline 1-cyclopropyl-6-fluoro-7-(2-methylisoindolin-5-yl)-1,4-dihydro-4-oxoquinoline-3-carboxylic acid.

IR (KBr) cm$^{-1}$: $v_{C=O}$ 1730

NMR (d$_1$-TFA) δ value: 1.20–2.05 (4H, m), 3.39 (3H, s), 4.00–5.60 (5H, m), 7.45–8.05 (3H, m), 8.50 (1H, d, J=9.2 Hz), 8.80 (1H, d, J=5.9 Hz), 9.50 (1H, s)

In the same manner, the following compounds were obtained.

1-Cyclopropyl-6-fluoro-8-methyl-7-(2-methylisoindolin-5-yl)-1,4-dihydro-4-oxoquinoline-3-carboxylic acid IR (KBr) cm$^{-1}$: $v_{C=O}$ 1725

NMR (d$_1$-TFA) δ value: 1.05–2.00 (4H, m), 2.93 (3H, s), 3.38 (3H, s), 4.30–5.50 (5H, m), 7.20–7.80 (3H, m), 8.34 (1H, d, J=7.3 Hz), 9.63 (1H, s)

(S)-9-Fluoro-3-methyl-10-(2-methylisoindolin-5-yl)-7-oxo-2,3-dihydro-7H-pyrido[1,2,3-de][1,4]benzoxazine-6-carboxylic acid IR (KBr) cm$^{-1}$: $v_{C=O}$ 1716

NMR (d$_1$-TFA) δ value: 1.50–2.20 (3H, m), 3.35 (3H, brs), 4.10–5.80 (7H, m), 6.90–8.30 (4H, m), 9.35 (1H, brs)

1-Cyclopropyl-6-fluoro-7-(2-methylisoindolin-5-yl)-1,4-dihydro-4-oxo-1,8-naphthyridine-3-carboxylic acid IR (KBr) cm$^{-1}$: $v_{C=O}$ 1727

NMR (CDCl$_3$) δ value: 0.90–1.55 (4H, m), 2.63 (3H, s), 3.50–4.20 (5H, m), 7.36 (1H, d, J=8.3 Hz), 7.80–8.20 (2H, m), 8.44 (1H, d, J=10.7 Hz), 8.93 (1H, s)

1-Cyclopropyl-6,8-difluoro-7-(2-methylisoindolin-5-yl)-1,4-dihydro-4-oxoquinoline-3-carboxylic acid IR (KBr) cm$^{-1}$: $v_{C=O}$ 1648

NMR (CDCl$_3$) δ value: 0.90–1.50 (4H, m), 2.60 (3H, brs), 3.50–4.40 (5H, m), 7.25 (3H, s), 8.07 (1H, d, J=8.5 Hz), 8.87 (1H, s)

1-Cyclopropyl-6-fluoro-8-methoxy-7-(2-methylisoindolin-5-yl)-1,4-dihydro-4-oxoquinoline-3-carboxylic acid IR (KBr) cm$^{-1}$: $v_{C=O}$ 1732

NMR (d$_1$-TFA) δ value: 1.20–1.80 (4H, m), 3.39 (3H, s), 3.63 (3H, s), 4.30–5.60 (5H, m), 7.73 (3H, brs), 8.26 (1H, d, J=8.5 Hz), 9.52 (1H, s)

1-Cyclopropyl-8-difluoromethoxy-6-fluoro-7-(2-methylisoindolin-5-yl)-1,4-dihydro-4-oxoquinoline-3-carboxylic acid IR (KBr) cm$^{-1}$: $v_{C=O}$ 1723

NMR (d$_1$-TFA) δ value: 1.00–2.00 (4H, m), 3.34 (3H, s), 4.30–5.50 (5H, m), 6.23 (1H, t, J=72 Hz), 7.73 (3H, brs), 8.47 (1H, d, J=8.3 Hz), 9.60 (1H, s)

6-Fluoro-1-(2-fluoroethyl)-8-methyl-7-(2-methylisoindolin-5-yl)-1,4-dihydro-4-oxoquinoline-3-carboxylic acid IR (KBr) cm$^{-1}$: $v_{C=O}$ 1718

Industrial Applicability

The compounds of the present invention in which a carbon atom of an isoindolin ring is bonded to 7-position of a quinolone- or naphthylidone-carboxylic acid skeleton are useful as an antibacterial agent.

What is claimed is:

1. A quinolone- or naphthylidone-carboxylic acid compound represented by the following formula or its salt:

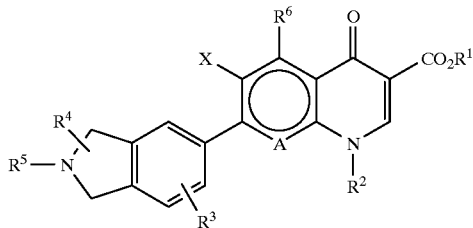

wherein $R^1$ represents a hydrogen atom or a carboxyl-protecting group; $R^2$ represents a substituted or unsubstituted alkyl, alkenyl, cycloalkyl, aryl or heterocyclic group; $R^3$ represents at least one member selected from the group consisting of a hydrogen atom, a halogen atom, a substituted or unsubstituted alkyl, alkenyl, cycloalkyl, aryl, alkoxy or alkylthio group, a nitro group, a cyano group, an acyl group, a protected or unprotected hydroxyl group, a protected or unprotected hydroxyalkyl group, a protected or unprotected amino group, a protected or unprotected alkylamino group, a dialkylamino group, a protected or unprotected aminoalkyl group, a protected or unprotected alkylaminoalkyl group and a dialkylaminoalkyl group; $R^4$ represents at least one member selected from the group consisting of a hydrogen atom, a halogen atom, a substituted or unsubstituted alkyl, alkenyl, cycloalkyl, aralkyl, aryl, alkoxy or alkylthio group, a protected or unprotected hydroxyl group, a protected or unprotected hydroxyalkyl group, a protected or unprotected amino group, a protected or unprotected alkylamino group, a dialkylamino group, a protected or unprotected aminoalkyl group, a protected or unprotected alkylaminoalkyl group, a dialkylaminoalkyl group, an alkylidene group, an oxo group, an imino group and a group forming a cycloalkane ring together with the carbon atom to which $R^4$ is bonded; $R^5$ represents a hydrogen atom, a substituted or unsubstituted alkyl, cycloalkyl, alkylsulfonyl, arylsulfonyl, acyl or aryl group, a protected or unprotected aminoalkyl group, a protected or unprotected alkylaminoalkyl group, a dialkylaminoalkyl group or a protected or unprotected hydroxyalkyl group; $R^6$ represents a hydrogen atom, a halogen atom, a substituted or unsubstituted alkyl, alkoxy or alkylthio group, a protected or unprotected hydroxyl group, a protected or unprotected amino group or a nitro group;

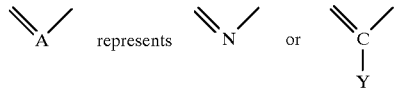

in which Y represents a hydrogen atom, a halogen atom, a substituted or unsubstituted alkyl, alkoxy or alkylthio group or a protected or unprotected hydroxyl group, or forms a group represented by the following formula together with $R^2$:

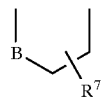

in which $R^7$ represents at least one member selected from the group consisting of a hydrogen atom, an alkyl group, a halogenoalkyl group, a protected or unprotected hydroxyalkyl group, an alkylidene group and a group forming a cycloalkane ring together with the carbon atom to which $R^7$ is bonded and B represents an oxygen atom, a sulfur atom or an imino group optionally substituted by an alkyl group; and X represents a hydrogen atom or a halogen atom.

2. The quinolone- or naphthylidone-carboxylic acid compound or its salt according to claim 1, wherein $R^2$ represents a substituted or unsubstituted lower alkyl, lower alkenyl, cycloalkyl, aryl or heterocyclic group; $R^3$ represents at least one member selected from the group consisting of a hydrogen atom, a halogen atom, a substituted or unsubstituted lower alkyl, lower alkenyl, cycloalkyl, aryl, lower alkoxy or lower alkylthio group, a nitro group, a cyano group, an acyl group, a protected or unprotected hydroxyl group, a protected or unprotected hydroxy-lower alkyl group, a protected or unprotected amino group, a protected or unprotected lower alkylamino group, a di-lower alkylamino group, a protected or unprotected amino-lower alkyl group, a protected or unprotected lower alkylamino-lower alkyl group and a di-lower alkylamino-lower alkyl group; $R^4$ represents at least one member selected from the group consisting of a hydrogen atom, a halogen atom, a substituted or unsubstituted lower alkyl, lower alkenyl, cycloalkyl, aralkyl, aryl, lower alkoxy or lower alkylthio group, a protected or unprotected hydroxyl group, a protected or unprotected hydroxy-lower alkyl group, a protected or unprotected amino group, a protected or unprotected lower alkylamino group, a di-lower alkylamino group, a protected or unprotected amino-lower alkyl group, a protected or unprotected lower alkylamino-lower alkyl group, a di-lower alkylamino-lower alkyl group, a lower alkylidene group, an oxo group, an imino group and a group forming a cycloalkane ring together with the carbon atom to which $R^4$ is bonded; $R^5$ represents a hydrogen atom, a substituted or unsubstituted lower alkyl, cycloalkyl, lower alkylsulfonyl, arylsulfonyl, acyl or aryl group, a protected or unprotected amino-lower alkyl group, a protected or unprotected lower alkylamino-lower alkyl group, a di-lower alkylamino-lower alkyl group or a protected or unprotected hydroxy-lower alkyl group; $R^6$ represents a hydrogen atom, a halogen atom, a substituted or unsubstituted lower alkyl, lower alkoxy or lower alkylthio group, a protected or unprotected hydroxyl group, a protected or unprotected amino group or a nitro group; and

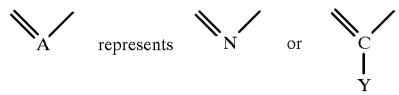

in which Y represents a hydrogen atom, a halogen atom, a substituted or unsubstituted lower alkyl, lower alkoxy or lower alkylthio group or a protected or unprotected hydroxyl group or forms a group represented by the following formula together with $R^2$:

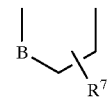

in which $R^7$ represents at least one member selected from the group consisting of a hydrogen atom, a lower alkyl group, a halogeno-lower alkyl group, a protected or unprotected hydroxy-lower alkyl group, a lower alkylidene group and a group forming a cycloalkane ring together with the carbon atom to which R⁷ is bonded and B represents an oxygen atom, a sulfur atom or an imino group optionally substituted by a lower alkyl group; and X represents a halogen atom.

3. The quinolone- or naphthylidone-carboxylic acid compound or its salt according to claim 1, wherein R³ represents at least one member selected from the group consisting of a hydrogen atom, a halogen atom, a substituted or unsubstituted lower alkyl, lower alkoxy or lower alkylthio group, a nitro group, a cyano group, a protected or unprotected hydroxyl group and a protected or unprotected amino group.

4. The quinolone- or naphthylidone-carboxylic acid compound or its salt according to claim 1, wherein R⁴ represents a hydrogen atom, a substituted or unsubstituted lower alkyl group, a lower alkylidene group and a group forming a cycloalkane ring together with the carbon atom to which R⁴ is bonded.

5. The quinolone- or naphthylidone-carboxylic acid compound or its salt according to claim 1, wherein R⁵ represents a hydrogen atom or a substituted or unsubstituted lower alkyl or cycloalkyl group.

6. The quinolone- or naphthylidone-carboxylic acid compound or its salt according to claim 1, wherein R⁶ represents a substituted or unsubstituted lower alkyl group or a protected or unprotected amino group.

7. The quinolone-carboxylic acid compound or its salt according to claim 1, wherein

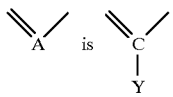

in which Y is as defined in claim 1.

8. The naphthylidone-carboxylic acid compound or its salt according to claim 1, wherein

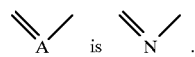

9. 1-Cyclopropyl-6-fluoro-7-(isoindolin-5-yl)-8-methyl-1,4-dihydro-4-oxoquinoline-3-carboxylic acid or its salt.

10. (S)-9-fluoro-3-methyl-10-(2-methylisoindolin-5-yl)-7-oxo-2,3-dihydro-7H-pyrido[1,2,3-de][1,4]benzoxazine-6-carboxylic acid or its salt.

11. 1-Cyclopropyl-6-fluoro-7-(isoindolin-5-yl)-8-methoxy-1,4-dihydro-4-oxoquinoline-3-carboxylic acid or its salt.

12. 1-Cyclopropyl-8-difluoromethoxy-6-fluoro-7-(isoindolin-5-yl)-1,4-dihydro-4-oxoquinoline-3-carboxylic acid or its salt.

13. 5-amino-1-cyclopropyl-6-fluoro-7-(isoindolin-5-yl)-8-methoxy-1,4-dihydro-4-oxoquinoline-3-carboxylic acid or its salt.

14. A method of inhibiting the growth of bacteria, comprising contacting bacteria with an effective amount of a quinolone- or naphthylidone-carboxylic acid compound or its salt according to claim 1.

15. A pharmaceutical composition comprising a pharmaceutically effective amount of a quinolone- or naphthylidone-carboxylic acid compound or a salt as claimed in claim 1 and a pharmaceutically acceptable preparation adjuvant.

* * * * *

UNITED STATES PATENT AND TRADEMARK OFFICE
CERTIFICATE OF CORRECTION

PATENT NO. : 5,935,952

DATED : August 10, 1999

INVENTOR(S): Yozo TODO, et al.

It is certified that an error appears in the above-identified patent and that said Letters Patent is hereby corrected as shown below:

On the title page, item [54], and on top of column 1, the title should read as follows:

--[54] QUINOLONE- OR NAPHTHYLIDONE-CARBOXYLIC ACID DERIVATIVES OR THEIR SALTS--

On the title page, item [75], the 3rd inventor's name should be:

--Masahiro Takahata--

Signed and Sealed this

Fifth Day of December, 2000

Attest:

Q. TODD DICKINSON

*Attesting Officer*  *Director of Patents and Trademarks*